United States Patent
Iwasawa et al.

(10) Patent No.: US 7,915,263 B2
(45) Date of Patent: Mar. 29, 2011

(54) AMINOPYRIDINE DERIVATIVES HAVING AURORA A SELECTIVE INHIBITORY ACTION

(75) Inventors: Yoshikazu Iwasawa, Tsukuba (JP); Tetsuya Kato, Tsukuba (JP); Nobuhiko Kawanishi, Moriya (JP); Kouta Masutani, Tsukuba (JP); Takashi Mita, Tsukuba (JP); Katsumasa Nonoshita, Tsukuba (JP); Mitsuru Ohkubo, Ushiku (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 799 days.

(21) Appl. No.: 11/897,272

(22) Filed: Aug. 29, 2007

(65) Prior Publication Data

US 2008/0058347 A1   Mar. 6, 2008

Related U.S. Application Data

(60) Provisional application No. 60/926,086, filed on Apr. 25, 2007.

(30) Foreign Application Priority Data

Aug. 31, 2006 (JP) .................... 2006-236472

(51) Int. Cl.
*C07D 401/12* (2006.01)
*A61K 31/4439* (2006.01)

(52) U.S. Cl. ............ 514/255.05; 514/340; 514/341; 514/342; 544/405; 546/268.4; 546/268.7; 546/269.1; 546/270.7; 546/275.4

(58) Field of Classification Search .......... None
See application file for complete search history.

(56) References Cited

U.S. PATENT DOCUMENTS

2006/0106029 A1   5/2006   Ohkubo et al.

FOREIGN PATENT DOCUMENTS

| WO | WO01/17995 | 3/2001 |
|---|---|---|
| WO | WO02/30358 | 4/2002 |
| WO | WO 02/45652 | 6/2002 |
| WO | WO 02/50065 | 6/2002 |
| WO | WO02/50066 | 6/2002 |
| WO | WO 02/059112 | 8/2002 |
| WO | WO 02/062789 | 8/2002 |
| WO | WO 02/066461 | 8/2002 |
| WO | WO 02/068415 | 9/2002 |
| WO | WO02/094264 | 11/2002 |
| WO | WO2006/053109 | 5/2006 |
| WO | WO2006/067466 | 6/2006 |
| WO | WO2006/074262 | 7/2006 |
| WO | WO2006/124874 | 11/2006 |

*Primary Examiner* — Zinna N Davis
(74) *Attorney, Agent, or Firm* — Matthew A. Leff; David A. Muthard

(57) ABSTRACT

The present invention relates to a compound of formula I:

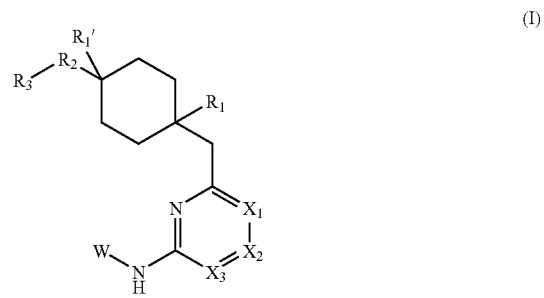

wherein: $R_1$ is a hydrogen atom, F, CN, etc.; $R_1'$ is a hydrogen atom or lower alkyl which may be substituted; $R_2$ is O, S, SO, $SO_2$, etc.; $R_3$ is a phenyl which may be substituted; $X_1$, $X_2$, and $X_3$ each independently CH, N, etc. provided, however, that among $X_1$, $X_2$ and $X_3$, the number of nitrogen is 0 or 1; W is the following residue:

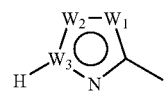

wherein: $W_1$, $W_2$, and $W_3$ each independently CH, N, etc., or a pharmaceutically acceptable salt or ester thereof.

20 Claims, No Drawings

SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Completely Synthetic Amino Acid Sequence
<220> FEATURE:
<221> NAME/KEY: AMIDATION
<222> LOCATION: (1)...(1)
<223> OTHER INFORMATION: Xaa = 5-FAM-gamma-aminobutyric acid
      5-FAM = 5-carboxyfluorescein

<400> SEQUENCE: 1

Xaa Ala Leu Arg Arg Ala Ser Leu Gly
 1               5

<210> SEQ ID NO 2
<211> LENGTH: 7
<212> TYPE: PRT
<213> ORGANISM: Artificial Sequence
<220> FEATURE:
<223> OTHER INFORMATION: Completely Synthetic Amino Acid Sequence

<400> SEQUENCE: 2

Leu Arg Arg Ala Ser Leu Gly
 1               5

AMINOPYRIDINE DERIVATIVES HAVING AURORA A SELECTIVE INHIBITORY ACTION

PRIORITY CLAIM

This application claims priority from U.S. Provisional Application No. 60/926,086 filed on Apr. 25, 2007, and Japanese Priority Application No. Japan 2006-236472, filed Aug. 31, 2006, now expired.

TECHNICAL FIELD

The present invention relates to novel aminopyridine derivatives which are useful in the pharmaceutical field, and more particularly, to those which inhibit the growth of tumor cells based on an Aurora A selective inhibitory action and exhibit an antitumor effect, and also to an Aurora A selective inhibitor and an antitumor agent containing them.

BACKGROUND ART

Aurora kinase is a serine/threonine kinase involved in cell division. With regard to the Aurora kinase, three subtypes of A, B and C are known at present, and they have very high homology to each other. Aurora A participates in the maturation and distribution of centrosome or in the formation of spindle body. On the other hand, it is believed that Aurora B participates in the aggregation and pairing of chromosome, a spindle checkpoint and cytoplasm division [*Nat. Rev. Mol. Cell Biol.*, No. 4, pp. 842-854]. Also, it is believed that Aurora C acts similarly as a result of interaction with Aurora B [*J. Biol. Chem.*, Epub ahead (2004)]. From the fact that high expression of Aurora A has been hitherto confirmed in many cancer cells; that high expression of Aurora A in normal cells leads to transformation of normal cell strains of rodent; and the like, Aurora A, being one of oncogenes, is recognized to be an adequate target for an antitumor agent [*EMBO J.*, No. 17, pp. 3052-3065 (1998)].

There is another report that cancer cells in which Aurora A is highly expressed have a resistance to paclitaxel [*Cancer Cell*, Vol. 3, pp. 51-62 (2003)]. Meanwhile, with regard to the Aurora kinase inhibitor, development of subtype-selective drugs has been thought to be difficult in view of high homology among subtypes, protein structure analysis and the like; and although there have been known reports on drugs such as ZM447439 which inhibit both Aurora A and Aurora B at the same time [*J. Cell Biol.*, No. 161, pp. 267-280 (2003); *J. Cell Biol.*, No. 161, pp. 281-294, (2003); *Nat. Med.*, No. 10, pp. 262-267, (2004)], no report concerning Aurora A selective drugs have been known. Thus, in those reports, disclosed is the antitumor effect only for the case where a drug which inhibits both Aurora A and Aurora B at the same time is solely administered. In addition, there has been also reported a result that in a drug which inhibits both Aurora A and Aurora B at the same time, the Aurora kinase inhibiting action attenuates the action of paclitaxel [*J. Cell Biol.*, No. 161, pp. 281-294, (2003)].

Now, patent applications concerning compounds having an Aurora kinase inhibiting action have been previously filed (WO 02/057259, U.S. Pat. No. 6,664,247, etc.), and patent applications concerning aminopyridine derivatives has been filed as well (U.S. Pat. No. 6,586,424, etc.). Under these circumstances, the present inventors filed a patent application directed to an aminopyridine derivative having an excellent Aurora A selective inhibitory action (WO2006/046734).

DISCLOSURE OF THE INVENTION

The problems that the present invention should solve are to create novel aminopyridine derivatives which show an excellent Aurora A selective inhibitory action and cell-growth inhibitory action based on the foregoing, as well as achieve a synergistic action by a combined use with other antitumor agent(s). Further, it is also the problems that the present invention should solve, to create, in the case of oral administration, novel aminopyridine derivatives which show an excellent Aurora A selective inhibitory action.

In order to solve the above problems, the present inventors have synthesized a variety of novel aminopyridine derivatives and found that the compound represented by the following Formula (I) shows an excellent Aurora A selective inhibitory action and cell-growth inhibitory action based on the foregoing, and also achieves a synergistic action by a combined use with other antitumor agents, thus completing the invention. With regard to those cancers which have been unable to be completely treated with known antitumor agents such as paclitaxel because it has been impossible to use a sufficient amount of the agents owing to side-effects or drug resistance thereof, the oral administration of the compound according to the invention or the combined administration of the compound according to the invention with other antitumor agent is expected to exhibit an excellent antitumor effect (including potentiation of action due to the other antitumor agent) and an effect of attenuating side-effects.

Thus, the invention relates to a compound of general formula I:

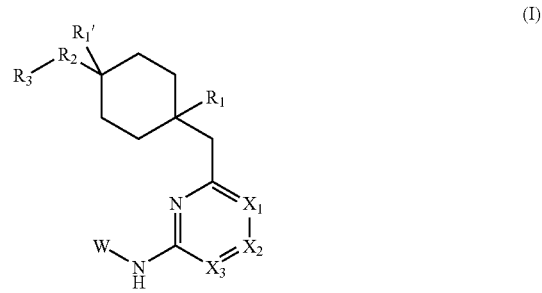

wherein:
R$_1$ is a hydrogen atom, F, CN, COOR$_{a1}$, CONR$_{a2}$R$_{a2}$', NR$_{a3}$COR$_{a3}$', CONR$_{a4}$OR$_{a4}$', NR$_{a5}$CONR$_{a5}$'R$_{a5}$", NR$_{a6}$COOR$_{a6}$', SO$_2$NR$_{a7}$R$_{a7}$', NR$_{a8}$SO$_2$R$_{a8}$', COR$_{a9}$, SO$_2$R$_{a10}$, NO$_2$, OR$_{a11}$, NR$_{a12}$R$_{a12}$', lower alkyl which may be substituted, or a heterocyclic group which may be substituted, wherein:
R$_{a1}$, R$_{a3}$, R$_{a4}$, R$_{a5}$, R$_{a6}$, and R$_{a8}$ are each independently a hydrogen atom or lower alkyl which may be substituted;

R$_{a2}$, R$_{a2}$', R$_{a5}$', R$_{a5}$", R$_{a7}$, R$_{a7}$', R$_{a12}$, and R$_{a12}$' are each independently a hydrogen atom or lower alkyl which may be substituted, provided, however, that R$_{a2}$ and R$_{a2}$'; R$_{a5}$' and R$_{a5}$"; R$_{a7}$ and R$_{a7}$'; R$_{a12}$ and R$_{a12}$' each independently, together with the nitrogen atom which they bind to, may form a heterocyclic group which may be substituted;

R$_{a3}$', R$_{a4}$', R$_{a6}$', R$_{a8}$', R$_{a9}$, R$_{a10}$ and R$_{a11}$ are each independently a hydrogen atom or lower alkyl which may be substituted;

$R_1'$ is a hydrogen atom or lower alkyl which may be substituted;

$R_2$ is O, S, SO, SO$_2$, NH, NR$_b$, or CR$_{c1}$R$_{c2}$ wherein R$_b$ is a lower alkyl which may be substituted, and R$_{c1}$ and R$_{c2}$, which may be the same or different, are a hydrogen atom or lower alkyl;

$R_3$ is a phenyl which may be substituted;

$X_1$ is CH, CX$_{1a}$, or N wherein X$_{1a}$ is a lower alkyl which may be substituted;

$X_2$ is CH, CX$_{2a}$, or N wherein:
  $X_{2a}$ is a lower alkyl; or
  $X_{2a}$ is a substituent selected from <substituent group A$_1$>, or lower alkyl which is substituted with one or more of the same or different substituents selected from <substituent group A$_1$>, wherein <substituent group A$_1$> is halogen atom; cyano; hydroxy; lower alkylamino; di-lower alkylamino; lower alkoxy which may be substituted with one or more hydroxy groups; lower alkylthio; and lower alkylsulfonyl; or
  $X_{2a}$ is COOR$_{x1}$, CONR$_{x2}$R$_{x3}$, NHCOR$_{x1}$, NHCONR$_{x2}$R$_{x3}$, NHSO$_2$NR$_{x2}$R$_{x3}$, NR$_{x4}$R$_{x5}$, or CH$_2$NR$_{x4}$R$_{x5}$, wherein:
    $R_{x1}$ is a hydrogen atom or lower alkyl which may be substituted;
    $R_{x2}$ and $R_{x3}$, which may be the same or different, are each a hydrogen atom, lower alkyl which may be substituted, or cycloalkyl which may be substituted; or alternatively $R_{x2}$ and $R_{x3}$, together with the nitrogen atom to which they bond, form a 5- or 6-membered aliphatic heterocyclic group which contains at least one atom selected from N, O and S and which may be substituted; and
    $R_{x4}$ and $R_{x5}$, which may be the same or different, are a hydrogen atom, lower alkyl that may be substituted, or cycloalkyl that may be substituted; or
  $X_{2a}$ is a 5- to 6-membered aliphatic heterocyclic group which contains at least one atom selected from N, O and S and which may be substituted, wherein two hydrogen atoms that are bonded to the same carbon atom of the aliphatic heterocyclic group may be substituted with oxo and neighboring two carbon atoms constituting the aliphatic heterocyclic ring may form a double-bond; or a lower alkyl which is substituted with the aliphatic heterocyclic group; or
  $X_{2a}$ is a 5- to 6-membered aromatic heterocyclic group which contains at least one atom selected from N, O and S and which may be substituted; or a lower alkyl which is substituted with the aromatic heterocyclic group;

$X_3$ is CH, CX$_{3a}$, or N wherein X$_{3a}$ is a lower alkyl which may be substituted;

provided, however, that among X$_1$, X$_2$ and X$_3$, the number of nitrogen is 0 or 1;

W is the following residue:

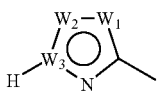

wherein:
  $W_1$ is CH, N, NH, O, or S;
  $W_2$ is CH, CW$_{2a}$, N, NW$_{2b}$, O or S, wherein W$_{2a}$ and W$_{2b}$ are each independently a hydrogen atom, halogen atom, cyano, lower alkyl having one to two carbon atoms, cycloalkyl having three to five carbon atoms, or lower alkyl having one to two carbon atoms which may be substituted with one or more halogen atoms;
  $W_3$ is C or N; and
  at least one of W$_1$, W$_2$, and W$_3$ is a carbon atom; however, two of W$_1$, W$_2$, and W$_3$ are not simultaneously O and S, or a pharmaceutically acceptable salt or ester thereof.

The invention also relates to a combined preparation for simultaneous, separate or sequential administration in the treatment of cancer, comprising two separate preparations which are:
  a preparation comprising, together with a pharmaceutically acceptable carrier or diluent, a compound represented by the above-described Formula (I) or a pharmaceutically acceptable salt or ester thereof; and
  a preparation comprising, together with a pharmaceutically acceptable carrier or diluent, one antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents as well as pharmaceutically acceptable salt(s) or ester(s) thereof, wherein:
    the antitumor alkylating agent is nitrogen mustard N-oxide, cyclophosphamide, ifosfamide, melphalan, busulfan, mitobronitol, carboquone, thiotepa, ranimustine, nimustine, temozolomide or carmustin;
    the antitumor antimetabolite is methotrexate, 6-mercaptopurine riboside, mercaptopurine, 5-fluorouracil, tegafur, doxyfluridine, carmofur, cytarabine, cytarabine ocfosfate, enocitabine, S-1, gemcitabine, fludarabine or pemetrexed disodium;
    the antitumor antibiotic is actinomrycin D, doxorubicin, daunorubicin, neocarzinostatin, bleomycin, peplomycine, mitomycin C, aclarubicin, pirarubicin, epirubicin, zinostatin stimalamer, idarubicin, sirolimus or valrubicin;
    the plant-derived antitumor agent is vincristine, vinblastine, vindesine, etoposide, sobuzoxane, docetaxel, paclitaxel or vinorelbine;
    the antitumor platinum coordination compound is cisplatin, carboplatin, nedaplatin or oxaliplatin;
    the antitumor camptothecin derivative is irinotecan, topotecan or camptothecin;
    the antitumor tyrosine kinase inhibitor is gefitinib, imatinib, sorafenib, sunitinib, dasatinib, or erlotinib;
    the monoclonal antibody is cetuximab, rituximab, bevacizumab, alemtuzumab or trastuzumab;
    the interferon is interferon α, interferon α-2a, interferon α-2b, interferon β, interferon γ-1a or interferon γ-n1;
    the biological response modifier is krestin, lentinan, sizofiran, picibanil or ubenimex; and
    the other antitumor agent is mitoxantrone, L-asparaginase, procarbazine, dacarbazine, hydroxycarbamide, pentostatin, tretinoin, alefacept, darbepoetin alfa, anastrozole, exemestane, bicalutamide, leuprolelin, flutamide, fulvestrant, pegaptanib octasodium, denileukin diftitox, aldesleukin, thyrotropin alfa, arsenic trioxide, bortezomib, capecitabine or goserelin.

The invention further relates to a pharmaceutical composition comprising, together with a pharmaceutically acceptable carrier or diluent, a compound represented by the above-described Formula (I) or a pharmaceutically acceptable salt or ester thereof, and an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, biological response modifiers and other antitumor agents (here, the definition of each antitumor agent is the same as that defined hereinabove) or a pharmaceutically acceptable salt or ester thereof.

The invention still further relates to a method for the treatment of cancer, comprising administering simultaneously, separately or sequentially a therapeutically effective amount of a compound represented by the above-described Formula (I) or a pharmaceutically acceptable salt or ester thereof in combination with a therapeutically effective amount of an antitumor agent selected from the group consisting of antitumor alkylating agents, antitumor antimetabolites, antitumor antibiotics, plant-derived antitumor agents, antitumor platinum coordination compounds, antitumor camptothecin derivates, antitumor tyrosine kinase inhibitors, monoclonal antibodies, interferons, biological response modifiers and other antitumor agents (here, definition of each antitumor agent is the same as that defined hereinabove) or a pharmaceutically acceptable salt or ester thereof.

Furthermore, the invention relates to the use of an Aurora selective A inhibitor for the manufacture of a medicament for the treatment of cancer; and the use of an Aurora selective A inhibitor in combination with an antitumor agent for the manufacture of a medicament for the treatment of cancer; and also relates to a method of treating cancer to a mammal (particularly a human) which comprises administering to said mammal a therapeutically effective amount of an Aurora selective A inhibitor; and a method of treating cancer in a mammal (particularly a human) which comprises administering to said mammal a therapeutically effective amount of an Aurora selective A inhibitor in combination with a therapeutically effective amount of an antitumor agent.

The invention relates to a pharmaceutical composition comprising as active ingredient an Aurora selective A inhibitor; and a pharmaceutical composition comprising as active ingredient an Aurora selective A inhibitor, together with an antitumor agent.

Next, symbols and terms used in the present specification will be explained.

The term "lower alkyl" in the above Formula (I) denotes a linear or branched alkyl group having 1 to 6 carbon atoms, and examples thereof include, for example, methyl, ethyl, propyl, isopropyl, butyl, isobutyl, sec-butyl, tert-butyl, pentyl and hexyl, among these methyl being preferred.

The term "cycloalkyl" in the above Formula (I) denotes a 3- to 8-membered aliphatic cyclic group such as, for example, cyclopropyl, cyclobutyl, cyclopentyl, cyclohexyl, cycloheptyl and cyclooctyl.

The "heterocyclic group" in the Formula (I) refers to an "aromatic heterocyclic group" or "aliphatic heterocyclic group". Here, the "aromatic heterocyclic group" refers to an aromatic heterocyclic group containing, in addition to a carbon atom(s), at least one heteroatom such as a nitrogen atom, an oxygen atom or the like, and examples thereof include a 5- to 7-membered monocyclic heterocyclic group, a fused-ring heterocyclic group formed by fusion of a 3- to 8-membered ring to the monocyclic heterocyclic group, and the like. Specifically, a thienyl group, a pyrrolyl group, a thiazolyl group, an imidazolyl group, a pyrazolyl group, an oxazolyl group, a pyridyl group, a pyrazinyl group, a pyrimidinyl group, a pyridazinyl group, an isoxazolyl group, an isoquinolyl group, an isoindolyl group, an indazolyl group, an indolyl group, a quinoxalinyl group, a quinolyl group, a benzoimidazolyl group, a benzofuranyl group and the like may be mentioned. On the other hand, the "aliphatic heterocyclic group" refers to a saturated or unsaturated aliphatic heterocyclic group containing, in addition to a carbon atom(s), at least one atom selected from a nitrogen atom, an oxygen atom and a sulfur atom in addition to carbon atoms, and having a monocyclic ring or a bicyclic or tricyclic fused ring. Examples thereof include an azetidyl group, a pyrrolidinyl group, a piperidinyl group, a piperazinyl group, a morpholino group, a tetrahydrofuranyl group, an imidazolidinyl group, a thiomorpholino group, a tetrahydroquinolyl group, a tetrahydroisoquinolyl group and the like.

The term "5- or 6-membered aliphatic heterocyclic group" in the above Formula (I) denotes a 5- or 6-membered aliphatic cyclic group containing at least one atom selected from nitrogen atom, oxygen atom and sulfur atom in addition to carbon atoms, and examples thereof include pyrrolidinyl, piperidinyl, piperazinyl, morpholino, tetrahydrofuranyl, imidazolidinyl and thiomorpholino. Further, for the aliphatic heterocyclic group, two hydrogen atoms which are bonded to the same carbon atom may be substituted with an oxo group, and also, adjacent carbon atoms constituting the ring of the aliphatic heterocyclic group may be double-bonded.

The term "5- or 6-membered aromatic heterocyclic group" in the above Formula (I) denotes a 5- or 6-membered aromatic cyclic group containing at least one atom selected from nitrogen atom, oxygen atom and sulfur atom in addition to carbon atoms, and examples thereof include thienyl, pyrrolyl, furyl, thiazolyl, imidazolyl and oxazolyl.

The term "halogen atom" in the above Formula (I) is, for example, fluorine atom, chlorine atom, bromine atom or iodine atom. Among them, for example, fluorine atom, chlorine atom or bromine atom is preferred.

The term "lower alkylamino" in the above Formula (I) denotes a group in which amino is N-substituted with the above-described "lower alkyl", and examples thereof include N-methylamino, N-ethylamino, N-propylamino, N-isopropylamino, N-butylamino, N-isobutylamino, N-tert-butylamino, N-pentylamino and N-hexylamino.

The term "di-lower alkylamino" in the above Formula (I) denotes a group in which amino is N,N-disubstituted with the above-described "lower alkyl", and examples thereof include N,N-dimethylamino, N,N-diethylamino, N,N-dipropylamino, N,N-diisopropylamino, N,N-dibutylamino, N,N-diisobutylamino, N,N-di-tert-butylamino, N,N-dipentylamino, N,N-dihexylamino, N-ethyl-N-methylamino and N-methyl-N-propylamino.

The term "lower alkylsulfonyl" in the above Formula (I) denotes a group in which the above-described "lower alkyl" is bonded to sulfonyl, and examples thereof include methylsulfonyl, ethylsulfonyl and butylsulfonyl.

The term "lower alkylsulfonylamino" in the above Formula (I) denotes a group in which the above-described "lower alkylsulfonyl" is bonded to amino, and examples thereof include methylsulfonylamino, ethylsulfonylamino and butylsulfonylamino.

The term "lower alkoxy" in the above Formula (I) denotes a group in which "lower alkyl" is bonded to oxygen atom, and examples thereof include methoxy, ethoxy, propoxy, isopropoxy, butoxy, isobutoxy, sec-butoxy, tert-butoxy, pentyloxy, neopentyloxy, hexyloxy and isohexyloxy.

The term "lower alkoxycarbonyl" in the above Formula (I) denotes a group in which "lower alkoxy" is bonded to carbonyl, and examples thereof include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, neopentyloxycarbonyl, hexyloxycarbonyl and isohexyloxycarbonyl.

The term "lower alkoxycarbonylamino" in the above Formula (I) denotes a group in which "lower alkoxycarbonyl" is bonded to amino, and examples thereof include methoxycarbonylamino, ethoxycarbonylamino, propoxycarbonylamino, isopropoxycarbonylamino, butoxycarbonylamino, isobutoxycarbonylamino, sec-butoxycarbonylamino, tert-butoxycarbonylamino, pentyloxycarbonylamino, neopentyloxycarbonylamino, hexyloxycarbonylamino and isohexyloxycarbonylamino.

The term "lower alkanoyl" in the above Formula (I) denotes a group in which the above-described "lower alkyl" is bonded to carbonyl, and examples thereof include acetyl, propionyl, butyryl, isobutyryl, valeryl, isovaleryl, pivaloyl and pentanoyl.

The term "lower alkanoyloxy" in the above Formula (I) denotes a group in which the above-described "lower alkanoyl" is bonded to an oxygen atom, and examples thereof include acetyloxy, propionyloxy, butyryloxy, isobutyryloxy, valeryloxy, isovaleryloxy, pivaloyloxy and pentanoyloxy.

The term "lower alkylthio" in the above Formula (I) denotes a substituent in which the above-described "lower alkyl" is bonded to sulfur atom, and examples thereof include methylthio, ethylthio and butylthio.

The term "selective inhibitor of Aurora A" used in the present specification is a compound or a drug which selectively inhibits Aurora A as compared with Aurora B. The "selective inhibitor of Aurora A" is preferably a compound or a drug of which inhibitory activities against Aurora A are at least ten times the activities against Aurora B; and more preferably a compound or a drug of which inhibitory activities against Aurora A are at least hundred times the activities against Aurora B.

Explanation for the term "pharmaceutically acceptable salt of ester thereof" or the term "pharmaceutically acceptable carrier or diluent" used in the specification still will be given later.

The term "treatment of cancer" as used in the specification means inhibition of cancer cell growth by administering an antitumor agent to a cancer patient. Preferably, this treatment enables retrogression of cancer growth, that is, reduction in the measurable cancer size. More preferably, such treatment completely eliminates cancer.

The term "cancer" as used in the specification refers to solid cancer and hematopoietic cancer. Here, examples of solid cancer include cerebral tumor, head and neck cancer, esophageal cancer, thyroid cancer, small cell lung cancer, non-small cell lung cancer, breast cancer, stomach cancer, gallbladder and bile duct cancer, liver cancer, pancreas cancer, colon cancer, rectal cancer, ovarian cancer, chorioepithelioma, uterine cancer, cervical cancer, renal pelvic and ureteral cancer, bladder cancer, prostate cancer, penile cancer, testicular cancer, embryonal cancer, wilms tumor, skin cancer, malignant melanoma, neuroblastoma, osteosarcoma, Ewing's tumor and soft tissue sarcoma. On the other hand, examples of hematopoietic cancer include acute leukemia, chronic lymphatic leukemia, chronic myelocytic leukemia, polycythemia vera, malignant lymphoma, multiple myeloma and non-Hodgkins' lymphoma.

The term "preparation" as used in the specification includes oral preparations and parenteral preparations. Examples of oral preparations include tablets, capsules, powders and granules, while examples of parenteral preparations include sterilized liquid preparations such as solutions or suspensions, specifically injections or drip infusions. Preferably, they are intravenous injections or intravenous drip infusions, and more preferably intravenous drip infusions.

The term "combined preparation" as used in the specification refers to those comprising two or more preparations for simultaneous, separate or sequential administration in the treatment, and such preparation may be a so-called kit type preparation or pharmaceutical composition. The term "combined preparation" also includes those having one or more preparations further combined with the combined preparation comprising two separate preparations used in the treatment of cancer.

The two separate preparations described above can be further combined with, in combination with a pharmaceutically acceptable carrier or diluent, at least one preparation comprising at least one antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined above), or a pharmaceutically acceptable salt or ester thereof. In this case, the above-mentioned at least one preparation that has been further combined can be administered simultaneously, separately or sequentially with respect to the two separate preparations. For example, a combined preparation comprising three preparations may include that is comprised of a preparation including a preparation containing the compound represented by the above Formula (I), a preparation containing 5-fluorouracil and a preparation containing leucovonin.

Here, in the above-mentioned combined preparation, either or both of the two separate preparations may be an oral preparation; and also one may be an oral preparation, while another may be a parental preparation (injections or drip infusions).

The term "preparation" according to the invention may usually comprise a therapeutically effective amount of a compound according to the invention, together with a pharmaceutically acceptable carrier or diluent. This technique of formulation is considered to be a technical common knowledge to those having ordinary skill in the pertinent art and is well known. Preferably, oral preparations, intravenous drip infusions or injections can be prepared in combination with a pharmaceutically acceptable carrier or diluent, by various methods that are well known in the art.

In the case of using the combined preparation according to the invention, the term "administration" as used in the present specification refers to parenteral administration and/or oral administration, and preferably oral administration. Thus, when a combined preparation is administered, both administrations may be parenteral; one administration may be parenteral while the other may be oral; or both administrations may be oral. Preferably, both preparations in the combined preparation are administered orally. Here, the term "parenteral administration" is, for example, intravenous administration, subcutaneous administration or intramuscular administration, and preferably it is intravenous administration. Even when three or more preparations are combined and administered, every preparation may be orally administered.

In the embodiment of the present invention, a compound represented by the above Formula (I) may be administered simultaneously with other antitumor agent(s). Further, it is possible to administer the compound represented by the above Formula (I) first and then another antitumor agent consecutively, or alternatively it is possible to administer another antitumor agent first and then the compound represented by the above Formula (I) consecutively. It is also possible to administer the compound represented by the above Formula (I) first and then separately administer another antitumor agent after a while, or alternatively it is possible to administer another antitumor agent first and then separately administer the compound represented by the above Formula (I) after a while. The order and the time interval for the administration may be appropriately selected by a person skilled in the art in accordance with, for example, a preparation containing the compound represented by the above Formula (I) used and a preparation containing an antitumor agent that is used in combination therewith, the type of the cancer cells to be treated and the condition of the patient. For example, in the case of administering the compound represented by the above Formula (I) and paclitaxel or docetaxel, preferably paclitaxel or docetaxel is administered first, and then the compound represented by the above Formula (I) is administered sequentially or separately after a while.

The term "simultaneously" as used in the specification refers to the use of preparations for the treatment substantially at the same time, whereas the term "separately" refers to the separate use of preparations for the treatment at different times such that, for example, one agent is used on the first day and another agent is used on the second day for the treatment. The term "sequentially" refers to the use of preparations in such an order that, for example, one agent is first used and another agent is used after a predetermined period of time for the treatment.

The term "antitumor alkylating agent" as used in the present specification refers to an alkylating agent having antitumor activity, and the term "alkylating agent" herein generally refers to an agent giving an alkyl group in the alkylation reaction in which a hydrogen atom of an organic compound is substituted with an alkyl group. The term "antitumor alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "antitumor antimetabolite" as used in the specification refers to an antimetabolite having antitumor activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "antitumor antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are 5-fluorouracil, S-1, gemcitabine and the like.

The term "antitumor antibiotic" as used in the specification refers to an antibiotic having antitumor activity, and the "antibiotic" herein includes substances that are produced by microorganisms or by organic synthesis and inhibit cell growth and other functions of microorganisms and of other living organisms. The term "antitumor antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin.

The term "plant-derived antitumor agent" as used in the specification includes compounds having antitumor activities which originate from plants, or compounds prepared by applying chemical modification to the foregoing compounds. The term "plant-derived antitumor agent" may be exemplified by vincristine, vinblastine, vindesine, etoposide, sobuzoxane, docetaxel, paclitaxel and vinorelbine, and preferred and docetaxel and paclitaxel.

The term "antitumor camptothecin derivative" as used in the specification refers to compounds that are structurally related to camptothecin and inhibit cancer cell growth, including camptothecin per se. The term "antitumor camptothecin derivative" is not particularly limited to, but may be exemplified by, camptothecin, 10-hydroxycamptothecin, topotecan, irinotecan or 9-aminocamptothecin, with camptothecin, topotecan and irinotecan being preferred. Further, irinotecan is metabolized in vivo and exhibits antitumor effect as SN-38. The action mechanism and the activity of the camptothecin derivatives are believed to be virtually the same as those of camptothecin (e.g., Nitta, et al., *Gan to Kagaku Ryoho,* 14, 850-857 (1987)).

The term "antitumor platinum coordination (platinum-complex) compound" as used in the specification refers to a platinum coordination compound having antitumor activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato) platinum (II) (carboplatin); spiroplatin; iproplatin; diammine(2-ethylmalonato)platinum (II); ethylenediaminemalonatoplatinum (II); aqua(1,2-diaminodicyclohexane) sulfatoplatinum (II); aqua(1,2-diaminodicyclohexane)malonatoplatinum (II); (1,2-diaminocyclohexane) malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is carboplatin or oxaliplatin. Further, other antitumor platinum coordination compounds mentioned in the specification are known and are commercially available and/or producible by a person having ordinary skill in the art by conventional techniques.

The term "antitumor tyrosine kinase inhibitor" as used in the specification refers to a tyrosine kinase inhibitor having antitumor activity, and the term "tyrosine kinase inhibitor" herein refers to a chemical substance inhibiting "tyrosine kinase" which transfers γ-phosphate group of ATP to a hydroxy group of a specific tyrosine in protein. The term "antitumor tyrosine kinase inhibitor" may be exemplified by gefitinib, imatinib, sorafenib, sunitinib, dasatinib, or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having antitumor activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon α, interferon α-2a, interferon α-2b, interferon β, interferon γ-1a and interferon γ-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofiran, picibanil and ubenimex.

The term "other antitumor agent" as used in the specification refers to an antitumor agent which does not belong to any of the above-described agents having antitumor activities. Examples of the "other antitumor agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "antitumor alkylating agent", "antitumor antimetabolite", "antitumor antibiotic", "plant-derived antitumor agent", "antitumor platinum coordination compound", "antitumor camptothecin derivative", "antitumor tyrosine kinase inhibitor", "monoclonal antibody", "interferon", "biological response modifier" and "other antitumor agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. No. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned antitumor alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from GlaxoSmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned antitumor antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned antitumor antibiotics are commercially available, as exemplified by the following: actinomycin D from Banyu Pharmaceutical Co., Ltd. as Cosmegen (tradename); doxorubicin from Kyowa Hakko Kogyo Co., Ltd. as adriacin (tradenaine); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived antitumor agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., ltd. as Lastet (tradename); sobuzoxane from Zenyaku Kogyo Co., Ltd. as Perazolin (tradename); docetaxel from Aventis Corp. as Taxotere (tradename); paclitaxel from Bristol-Myers Squibb Co. as Taxol (tradename); and vinorelbine from Kyowa Hakko Kogyo Co., Ltd. as Navelbine (tradename).

The above-mentioned antitumor platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned antitumor camptothecin derivatives are commercially available, as exemplified by the following: irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned antitumor tyrosine kinase inhibitors are commercially available, as exemplified by the following: gefitinib from AstraZeneca Corp. as Iressa (tradename); imatinib from Novartis AG as Gleevec (tradename); sorafenib from Bayer as Nexavar (tradename); sunitinib from Pfizer as Sutent (tradename); dasatinib from Bristol Myers Squibb as Sprycel (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon a from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon β from Mochida Pharmaceutical Co., Ltd. as IFNβ (tradename); interferon γ-1a from Shionogi & Co., Ltd. as Imunomax-γ (tradename); and interferon γ-n1 from Otsuka Pharmaceutical Co., Ltd. as Ogamma (tradename).

The above-mentioned biological response modifiers are commercially available, as exemplified by the following: krestin from Sankyo Co., Ltd. as krestin (tradename); lentinan from Aventis Corp. as Lentinan (tradename); sizofiran from Kaken Seiyaku Co., Ltd. as Sonifiran (tradename); picibanil from Chugai Pharmaceutical Co., Ltd. as Picibanil (tradename); and ubenimex from Nippon Kayaku Co., Ltd. as Bestatin (tradename).

The above-mentioned other antitumor agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

The term "antitumor agent" as used in the specification includes the above-described "antitumor alkylating agent", "antitumor antimetabolite", "antitumor antibiotic", "plant-derived antitumor agent", "antitumor platinum coordination compound", "antitumor camptothecin derivative", "antitumor tyrosine kinase inhibitor", "monoclonal antibody", "interferon", "biological response modifier" and "other antitumor agent".

The term "aminopyridine derivative" as used in the specification includes, but is not limited to, any compound having a pyridyl group or a pyridine analogue group, any of which is substituted with an amino group. It is exemplified by a compound of the above General Formula (I), and preferably any one compound of the below-mentioned (a) to (l): a compound which is:

(a) trans-4-(3-chloro-2-fluorophenoxy)-1-((6-(1,3-thiazol-2-ylamino)pyridin-2-yl)methyl)cyclohexanecarboxylic acid (Example 1 and 2);
(b) trans-4-(2-fluoro-3-(trifluoromethyl)phenoxy)-1-((6-(1,3-thiazol-2-ylamino)pyridin-2-yl)methyl)cyclohexanecarboxylic acid (Example 4);
(c) trans-4-(2,3-dichlorophenoxy)-1-((6-(1,3-thiazol-2-ylamino)pyridin-2-yl)methyl)cyclohexanecarboxylic acid (Example 6);
(d) trans-4-(2-fluoro-3-(trifluoromethyl)phenoxy)-1-((6-(1H-pyrazol-3-ylamino)pyridin-2-yl)methyl)cyclohexanecarboxylic acid (Example 9);
(e) trans-4-(3-chloro-2-fluorophenoxy)-1-((6-(1H-pyrazol-3-ylamino)pyrazin-2-yl)methyl)cyclohexanecarboxamide (Example 15);
(f) 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazol-2(3H)-one (Example 20);
(g) 5-(trans-4-(3-chloro-2-fluorophenoxy)-1-((6-(1H-pyrazol-3-ylamino)pyridin-2-yl)methyl)cyclohexyl)-1,3,4-oxadiazol-2(3H)-one (Example 23);
(h) 5-(trans-4-(3-chloro-2-fluorophenoxy)-1-((6-(1H-pyrazol-3-ylamino)pyrazin-2-yl)methyl)cyclohexyl)-1,3,4-oxadiazol-2(3H)-one (Example 29);
(i) 5-(trans-4-((2,3-dichlorophenyl)sulfonyl)-1-((6-(1H-pyrazol-3-ylamino)pyridin-2-yl)methyl)cyclohexyl)-1,3,4-oxadiazol-2(3H)-one (Example 36),
(j) trans-1-((4-bromo-6-(1,3-thiazol-2-ylamino)pyridin-2-yl)methyl)-4-(3-chloro-2-fluorophenoxy)cyclohexanecarboxylic acid (Example 40),
(k) 5-(trans-4-(3-chloro-2-fluorophenoxy)-1-((4-methyl-6-(1H-pyrazol-3-ylamino)pyrimidin-2-yl)methyl)cyclohexyl)-1,3,4-oxadiazol-2(3H)-one (Example 41), or
(l) 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazole-2(3H)-thione (Example 42),
or a pharmaceutically acceptable salt or ester thereof.

Embodiments of the compound represented by the above General Formula (I) will be illustrated in more detail.

$R_1$ is a hydrogen atom, F, CN, $COOR_{a1}$, $CONR_{a2}R_{a2}'$, $NR_{a3}COR_{a3}'$, $CONR_{a4}OR_{a4}'$, $NR_{a5}CONR_{a5}'R_{a5}''$, $NR_{a6}COOR_{a6}'$, $SO_2NR_{a7}R_{a7}'$, $NR_{a8}SO_2R_{a8}'$, $COR_{a9}$, $SO_2R_{a10}$, $NO_2$, $OR_{a11}$, $NR_{a12}R_{a12}'$, lower alkyl which may be substituted, or a heterocyclic group which may be substituted, wherein:

$R_{a1}$, $R_{a3}$, $R_{a4}$, $R_{a5}$, $R_{a6}$, and $R_{a8}$ are each independently a hydrogen atom or lower alkyl which may be substituted;

$R_{a2}$, $R_{a2}'$, $R_{a5}'$, $R_{a5}''$, $R_{a7}$, $R_{a7}'$, $R_{a12}$, and $R_{a12}'$ are each independently a hydrogen atom or lower alkyl which may be substituted, provided, however, that $R_{a2}$ and $R_{a2}'$; $R_{a5}'$ and $R_{a5}''$; $R_{a7}$ and $R_{a7}'$; $R_{a12}$ and $R_{a12}'$ each independently, together with the nitrogen atom which they bind to, may form a heterocyclic group which may be substituted;

$R_{a3}'$, $R_{a4}'$, $R_{a6}'$, $R_{a8}'$, $R_{a9}$, $R_{10}$ and $R_{a11}$ are each independently a hydrogen atom or lower alkyl which may be substituted;

Preferably, $R_1$ is a hydrogen atom, F, CN, $COOR_{a1}$, $CONR_{a2}R_{a2}'$, $NR_{a3}COR_{a3}'$, $CONR_{a4}OR_{a4}'$, $NR_{a5}CONR_{a5}'R_{a5}''$, $NR_{a6}COOR_{a6}'$, $SO_2NR_{a7}R_{a7}'$, $NR_{a8}SO_2R_{a8}'$, $COR_{a9}$, $SO_2R_{a10}$, $NO_2$, $OR_{a11}$, or $NR_{a12}R_{a12}'$, wherein:

$R_{a1}$, $R_{a3}$, $R_{a4}$, $R_{a5}$, $R_{a6}$, and $R_{a8}$ are each independently a hydrogen atom or lower alkyl;

$R_{a2}$, $R_{a2}'$, $R_{a5}'$, $R_{a5}''$, $R_{a7}$, $R_{a7}'$, $R_{a12}$, and $R_{a12}'$ are each independently a hydrogen atom or lower alkyl which may be substituted with one or more of the same or different substituents selected from <substituent group $L_1$>, wherein <substituent group $L_1$> is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; provided, however, that $R_{a2}$ and $R_{a2}'$; $R_{a5}'$ and $R_{a5}''$; $R_{a7}$ and $R_{a7}'$; $R_{a12}$ and $R_{a12}'$ each independently, together with the nitrogen atom which they bind to, may form a 5-membered or 6-membered aromatic or aliphatic heterocyclic group which may be substituted with one or more of the same or different substituents selected from <substituent group $L_2$>, wherein <substituent group $L_2$> is a halogen atom, hydroxy, amino, and hydroxymethyl;

$R_{a3}'$, $R_{a4}'$, $R_{a6}'$, $R_{a8}'$, $R_{a9}$, $R_{10}$ and $R_{a11}$ are each independently a hydrogen atom or lower alkyl which may be substituted with one or more of the same or different substituents selected from <substituent group $L_1$>; or $R_1$ is a lower alkyl which may be substituted with one or more of the same or different substituents selected from <substituent group M>, wherein <substituent group M> is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; or $R_1$ is a heterocyclic group selected from the following, wherein $Y_1$ and $Y_2$ are the same and different, and each a hydrogen atom or lower alkyl which may be substituted:

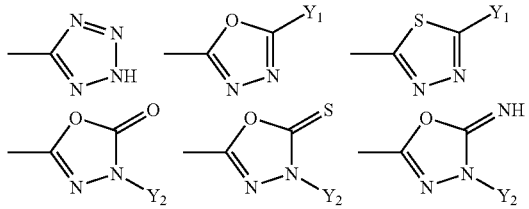

More preferably, $R_1$ is OH, COOH, or $CONR_{a2}R_{a2}'$ wherein $R_{a2}$ and $R_{a2}'$ are the same or different, and each a hydrogen atom or lower alkyl having one to three carbon atoms; or $R_1$ is selected from the following:

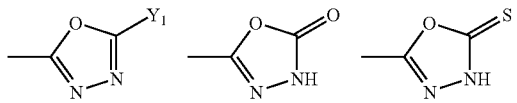

<substituent group $L_1$> is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; preferably, a hydrogen atom, hydroxy, amino, carbamoyl, lower alkylamino, di-lower alkylamino, and lower alkoxy.

<substituent group $L_2$> is a halogen atom, hydroxy, amino, and hydroxymethyl; preferably hydroxy and hydroxymethyl.

<substituent group M> is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; preferably, a hydroxy, carbamoyl, aminosulfonyl, lower alkylsulfonylamino, and carboxyl.

$R_1'$ is a hydrogen atom or lower alkyl which may be substituted; preferably, a hydrogen atom.

$R_2$ is O, S, SO, $SO_2$, NH, $NR_b$, or $CR_{c1}R_{c2}$ wherein $R_b$ is a lower alkyl which may be substituted, and $R_{c1}$ and $R_{c2}$, which may be the same or different, are a hydrogen atom or lower alkyl which may be substituted.

Preferably, $R_2$ is O, S, SO, or $SO_2$; more preferably, O.

$R_3$ is a phenyl which may be substituted; preferably, $R_3$ is a phenyl which is substituted; more preferably, $R_3$ is phenyl of which $2^{nd}$ and $3^{rd}$ positions are substituted with the same or different two substituents selected from F, Cl, $CF_3$, and CN.

$X_1$ is CH, $CX_{1a}$, or N wherein $X_{1a}$ is a lower alkyl which may be substituted.

Preferably, $X_1$ is CH or N; more preferably, CH.

$X_2$ is CH, $CX_{2a}$, or N wherein:

$X_{2a}$ is a lower alkyl; or $X_{2a}$ is a substituent selected from <substituent group $A_1$>, or lower alkyl which is substituted with one or more of the same or different substituents selected from <substituent group $A_1$>, wherein <substituent group $A_1$> is halogen atom; cyano; hydroxy; lower alkylamino; di-lower alkylamino; lower alkoxy which may be substituted with one or more hydroxy groups; lower alkylthio; and lower alkylsulfonyl; or $X_{2a}$ is $COOR_{x1}$, $CONR_{x2}R_{x3}$, $NHCOR_{x1}$, $NHCONR_{x2}R_{x3}$, $NHSO_2NR_{x2}R_{x3}$, $NR_{x4}R_{x5}$, or $CH_2NR_{x4}R_{x5}$, wherein:

$R_{x1}$ is a hydrogen atom or lower alkyl which may be substituted;

$R_{x2}$ and $R_{x3}$, which may be the same or different, are each a hydrogen atom, lower alkyl which may be substituted, or cycloalkyl which may be substituted; or alternatively $R_{x2}$ and $R_{x3}$, together with the nitrogen atom to which they bond, form a 5- or 6-membered aliphatic heterocyclic group which contains at least one atom selected from N, O and S and which may be substituted; and $R_{x4}$ and $R_{x5}$, which may be the same or different, are a hydrogen atom, lower alkyl that may be substituted, or cycloalkyl that may be substituted; or $X_{2a}$ is a 5- to 6-membered aliphatic heterocyclic group which contains at least one atom selected from N, O and S and which may be substituted, wherein two hydrogen atoms that are bonded to the same carbon atom of the aliphatic heterocyclic group may be substituted with oxo and neighboring two carbon atoms constituting the aliphatic heterocyclic ring may form a double-bond; or lower alkyl which is substituted with the aliphatic heterocyclic group; or $X_{2a}$ is a 5- to 6-membered aromatic heterocyclic group which contains at least one atom selected from N, O and S and which may be substituted; or lower alkyl which is substituted with the aromatic heterocyclic group.

Preferably, $X_2$ is CH, $CX_{2a}$, or N wherein $X_{2a}$ is a lower alkyl or a halogen atom.

More preferably, $X_2$ is CH or N $X_3$ is CH, $CX_{3a}$, or N wherein $X_{3a}$ is a lower alkyl which may be substituted.

Preferably, $X_3$ is CH.

However, among $X_1$, $X_2$ and $X_3$, the number of nitrogen is 0 or 1;

With regard to the combinations between $X_1$ and $X_2$, preferably, both $X_1$ and $X_2$ are CH; or $X_1$ is CH and $X_2$ is N; or $X_1$ is N and $X_2$ is CH or $CX_{2a}$ wherein $X_{2a}$ is a lower alkyl.

With regard to the combinations between $X_1$ and $X_2$, more preferably, both $X_1$ and $X_2$ are CH; or $X_1$ is CH and $X_2$ is N.

<substituent group $A_1$> is halogen atom; cyano; hydroxy; lower alkylamino; di-lower alkylamino; lower alkoxy which may be substituted with one or more hydroxy groups; lower alkylthio; and lower alkylsulfonyl; preferably, halogen atom, hydroxy, di-lower alkylamino and lower alkylsulfonyl.

W is the following residue:

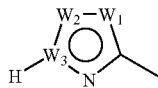

wherein:
$W_1$ is CH, N, NH, O, or S;
$W_2$ is CH, $CW_{2a}$, N, $NW_{2b}$, O or S, wherein $W_{2a}$ and $W_{2b}$ are each independently a hydrogen atom, halogen atom, cyano, lower alkyl having one to two carbon atoms, cycloalkyl having three to five carbon atoms, or lower alkyl having one to two carbon atoms which may be substituted with one or more halogen atoms;
$W_3$ is C or N; and
at least one of $W_1$, $W_2$, and $W_3$ is a carbon atom; however two of $W_1$, $W_2$, and $W_3$ are not simultaneously O and S.

W is preferably selected from:

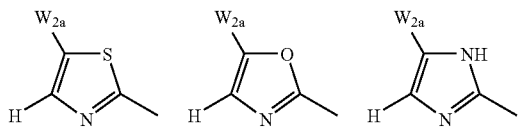

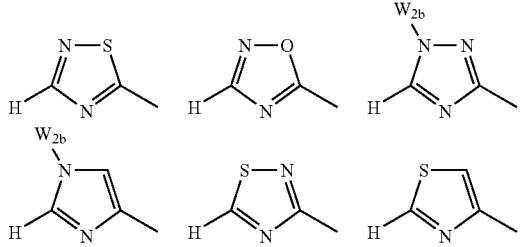

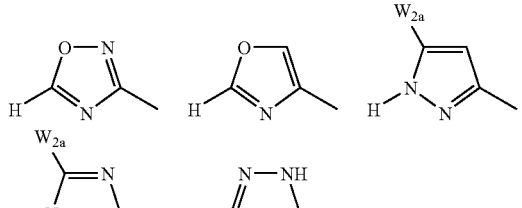

W is more preferably selected from:

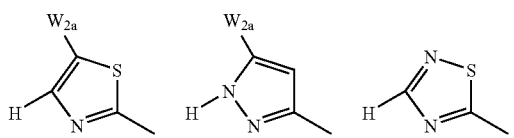

wherein $W_{2a}$ is a hydrogen atom, halogen atom, cyano, or methyl which may be substituted with one to three fluorine atoms.

W is particularly preferably selected from:

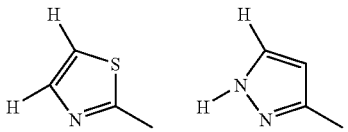

W is still more preferably selected from:

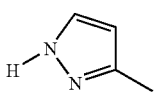

A preferred embodiment of the compound represented by the above General Formula (I) can be also expressed as follows:

(1) The compound of the above Formula (I) or a pharmaceutically acceptable salt or ester thereof, wherein $R_1'$ is a hydrogen atom, and $X_3$ is CH.

(2) The compound as described in above (1), or a pharmaceutically acceptable salt or ester thereof, wherein:

$R_1$ is a hydrogen atom, F, CN, $COOR_{a1}$, $CONR_{a2}R_{a2}'$, $NR_{a3}COR_{a3}'$, $CONR_{a4}OR_{a4}'$, $NR_{a5}CONR_{a5}'R_{a5}''$, $NR_{a6}COOR_{a6}'$, $SO_2NR_{a7}R_{a7}'$, $NR_{a8}SO_2R_{a8}'$, $COR_{a9}$, $SO_2R_{a10}$, $NO_2$, $OR_{a11}$, or $NR_{a12}R_{a12}'$, wherein:
$R_{a1}$, $R_{a3}$, $R_{a4}$, $R_{a5}$, $R_{a6}$, and $R_{a8}$ are each independently a hydrogen atom or lower alkyl;
$R_{a2}$, $R_{a2}'$, $R_{a5}'$, $R_{a5}''$, $R_{a7}$, $R_{a7}'$, $R_{a12}$, and $R_{a12}'$ are each independently a hydrogen atom or lower alkyl which may be substituted with one or more of the same or different substituents selected from <substituent group $L_1$>, wherein <substituent group $L_1$> is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; provided, however, that $R_{a2}$ and $R_{a2}'$; $R_{a5}'$ and $R_{a5}''$; $R_{a7}$ and $R_{a7}'$; $R_{a12}$ and $R_{a12}'$ each independently, together with the nitrogen atom which they bind to, may form a 5-membered or 6-membered aromatic or aliphatic heterocyclic group which may be substituted with one or more of the same or different substituents selected from <substituent group $L_2$>, wherein <substituent group $L_2$> is a halogen atom, hydroxy, amino, and hydroxymethyl;
$R_{a3}'$, $R_{a4}'$, $R_{a6}'$, $R_{a8}'$, $R_{a9}$, $R_{10}$ and $R_{a11}$ are each independently a hydrogen atom or lower alkyl which may be substituted with one or more of the same or different substituents selected from <substituent group $L_1$>; or $R_1$ is a lower alkyl which may be substituted with one or more of the same or different substituents selected from <substituent group M>, wherein <substituent group M> is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; or R₁ is a heterocyclic group selected from the following, wherein Y₁ and Y₂ are the same and different, and each a hydrogen atom or lower alkyl which may be substituted:

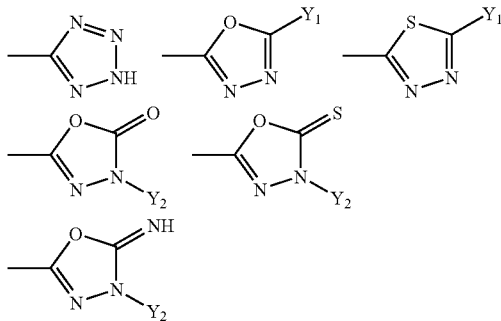

(3) The compound as described in above (2), or a pharmaceutically acceptable salt or ester thereof, wherein W is selected from:

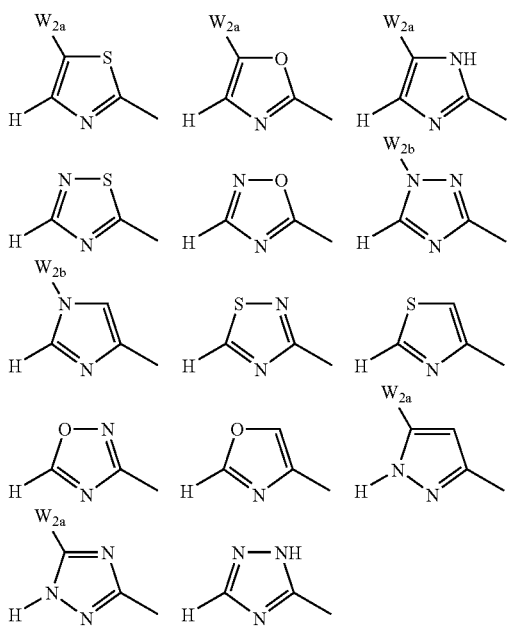

(4) The compound as described in above (3), or a pharmaceutically acceptable salt or ester thereof, wherein R₃ is a phenyl of which $2^{nd}$ and $3^{rd}$ positions are substituted with the same or different two substituents selected from F, Cl, CF₃, and CN.

(5) The compound as described in above (4), or a pharmaceutically acceptable salt or ester thereof, wherein <substituent group L₁> is a halogen atom, hydroxy, amino, carbamoyl, lower alkylamino, di-lower alkylamino, and lower alkoxy; and <substituent group M> is a hydroxy, carbamoyl, aminosulfonyl, lower alkylsulfonylamino, and carboxyl.

(6) The compound as described in above (5), or a pharmaceutically acceptable salt or ester thereof, wherein both X₁ and X₂ are CH; or X₁ is CH and X₂ is N; or
X₁ is N and X₂ is CH or CX$_{2a}$ wherein X$_{2a}$ is a lower alkyl or a halogen atom.

(7) The compound as described in above (6), or a pharmaceutically acceptable salt or ester thereof, wherein R₁ is OH, COOH, or CONR$_{a2}$R$_{a2}$' wherein R$_{a2}$ and R$_{a2}$' are the same or different, and each a hydrogen atom or lower alkyl having one to three carbon atoms; or R₁ is selected from the following:

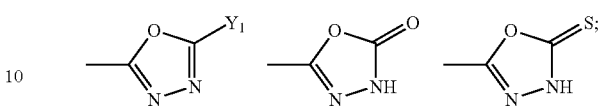

and R₂ is O, S, SO, or SO₂.

(8) The compound as described in above (7), or a pharmaceutically acceptable salt or ester thereof, wherein:
W is selected from:

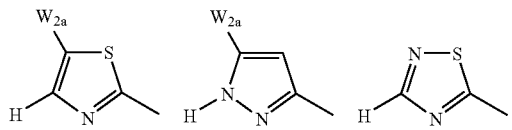

wherein W$_{2a}$ is a hydrogen atom, halogen atom, cyano, or methyl which may be substituted with one to three fluorine atoms.

(9) The compound as described in above (8), or a pharmaceutically acceptable salt or ester thereof, wherein both of X₁ and X₂ are CH; or X₁ is CH and X₂ is N; and W is any one of the following:

(10) A compound which is:
(a) trans-4-(3-chloro-2-fluorophenoxy)-1-((6-(1,3-thiazol-2-ylamino)pyridin-2-yl)methyl)cyclohexanecarboxylic acid;
(b) trans-4-(2-fluoro-3-(trifluoromethyl)phenoxy)-1-((6-(1,3-thiazol-2-ylamino)pyridin-2-yl)methyl)cyclohexanecarboxylic acid;
(c) trans-4-(2,3-dichlorophenoxy)-1-((6-(1,3-thiazol-2-ylamino)pyridin-2-yl)methyl)cyclohexanecarboxylic acid;
(d) trans-4-(2-fluoro-3-(trifluoromethyl)phenoxy)-1-((6-(1H-pyrazol-3-ylamino)pyridin-2-yl)methyl)cyclohexanecarboxylic acid;
(e) trans-4-(3-chloro-2-fluorophenoxy)-1-((6-(1H-pyrazol-3-ylamino)pyrazin-2-yl)methyl)cyclohexanecarboxamide;
(f) 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazol-2(3H)-one;
(g) 5-(trans-4-(3-chloro-2-fluorophenoxy)-1-((6-(1H-pyrazol-3-ylamino)pyridin-2-yl)methyl)cyclohexyl)-1,3,4-oxadiazol-2(3H)-one;
(h) 5-(trans-4-(3-chloro-2-fluorophenoxy)-1-((6-(1H-pyrazol-3-ylamino)pyrazin-2-yl)methyl)cyclohexyl)-1,3,4-oxadiazol-2(3H)-one;
(i) 5-(trans-4-((2,3-dichlorophenyl)sulfonyl)-1-((6-(1H-pyrazol-3-ylamino)pyridin-2-yl)methyl)cyclohexyl)-1,3,4-oxadiazol-2(3H)-one, (j) trans-1-((4-bromo-6-(1,3-thiazol-2-ylamino)pyridin-2-yl)methyl)-4-(3-chloro-2-fluorophenoxy)cyclohexanecarboxylic acid,
(k) 5-(trans-4-(3-chloro-2-fluorophenoxy)-1-((4-methyl-6-(1H-pyrazol-3-ylamino)pyrimidin-2-yl)methyl)cyclohexyl)-1,3,4-oxadiazol-2(3H)-one, or
(l) 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazole-2(3H)-thione, or a pharmaceutically acceptable salt or ester thereof.

Also, in another embodiment, the invention relates to a compound of general formula ($I_0$):

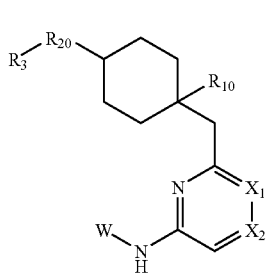

wherein:
$R_{10}$ is a hydrogen atom, F, CN, OH, $CH_2OH$, COOH, or $CONR_{a10}R_{a20}$ wherein $R_{10}$ and $R_{a20}$, which may be the same or different, are a hydrogen atom or lower alkyl;
$R_{20}$ is O, S, NH, $NR_b$, or $CR_{c1}R_{c2}$ wherein $R_b$ is a lower alkyl, and $R_{c1}$ and $R_{c2}$, which may be the same or different, are a hydrogen atom or lower alkyl;
$R_3$ is phenyl which may be substituted;
$X_1$ is CH, $CX_{1a}$, or N wherein $X_{1a}$ is a lower alkyl which may be substituted;
$X_2$ is CH, $CX_{2a}$, or N wherein:
  $X_{2a}$ is a lower alkyl; or
  $X_{2a}$ is a substituent selected from <substituent group $A_1$>, or lower alkyl which is substituted with one or more of the same or different substituents selected from <substituent group $A_1$>, wherein <substituent group $A_1$> is halogen atom; cyano; hydroxy; lower alkylamino; di-lower alkylamino; lower alkoxy which may be substituted with one or more hydroxy groups; lower alkylthio; and lower alkylsulfonyl; or
  $X_{2a}$ is $COOR_{x1}$, $CONR_{x2}R_{x3}$, $NHCOR_{x1}$, $NHCONR_{x2}R_{x3}$, $NHSO_2NR_{x2}R_{x3}$, $NR_{x4}R_{x5}$, or $CH_2NR_{x4}R_{x5}$, wherein:
    $R_{x1}$ is a hydrogen atom or lower alkyl which may be substituted;
    $R_{x2}$ and $R_{x3}$, which may be the same or different, are each a hydrogen atom, lower alkyl which may be substituted, or cycloalkyl which may be substituted; or alternatively $R_{x2}$ and $R_{x3}$, together with the nitrogen atom to which they bond, form a 5- or 6-membered aliphatic heterocyclic group which contains at least one atom selected from N, O and S and which may be substituted; and
    $R_{x4}$ and $R_{x5}$, which may be the same or different, are a hydrogen atom, lower alkyl that may be substituted, or cycloalkyl that may be substituted; or
  $X_{2a}$ is a 5- to 6-membered aliphatic heterocyclic group which contains at least one atom selected from N, O and S and which may be substituted, wherein two hydrogen atoms that are bonded to the same carbon atom of the aliphatic heterocyclic group may be substituted with oxo and neighboring two carbon atoms constituting the aliphatic heterocyclic ring may form a double-bond; or lower alkyl which is substituted with the aliphatic heterocyclic group; or
  $X_{2a}$ is a 5- to 6-membered aromatic heterocyclic group which contains at least one atom selected from N, O and S and which may be substituted; or a lower alkyl which is substituted with the aromatic heterocyclic group;

provided, however, that among $X_1$ and $X_2$, the number of nitrogen is 0 or 1;
W is the following residue:

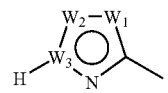

wherein:
  $W_1$ is CH, N, NH, O, or S;
  $W_2$ is CH, $CW_{2a}$, N, $NW_{2b}$, O or S, wherein $W_{2a}$ and $W_{2b}$ are each independently a hydrogen atom, halogen atom, cyano, lower alkyl having one to two carbon atoms, cycloalkyl having three to five carbon atoms, or lower alkyl having one to two carbon atoms which may be substituted with one or more halogen atoms;
  $W_3$ is C or N; and
  at least one of $W_1$, $W_2$, and $W_3$ is a carbon atom; however two of $W_1$, $W_2$, and $W_3$ are not simultaneously O and S, or a pharmaceutically acceptable salt or ester thereof.

Further, in the combined preparation comprising two separate preparations according to the invention, preferably either or both of the two separate preparations are an oral preparation.

The combined preparation comprising two separate preparations according to the invention is preferably such that one of the preparations is a preparation containing, together with a pharmaceutically acceptable carrier or diluent, the following:
(a) trans-4-(3-chloro-2-fluorophenoxy)-1-((6-(1,3-thiazol-2-ylamino)pyridin-2-yl)methyl)cyclohexanecarboxylic acid;
(b) trans-4-(2-fluoro-3-(trifluoromethyl)phenoxy)-1-((6-(1,3-thiazol-2-ylamino)pyridin-2-yl)methyl)cyclohexanecarboxylic acid;
(c) trans-4-(2,3-dichlorophenoxy)-1-((6-(1,3-thiazol-2-ylamino)pyridin-2-yl)methyl)cyclohexanecarboxylic acid;
(d) trans-4-(2-fluoro-3-(trifluoromethyl)phenoxy)-1-((6-(1H-pyrazol-3-ylamino)pyridin-2-yl)methyl)cyclohexanecarboxylic acid;
(e) trans-4-(3-chloro-2-fluorophenoxy)-1-((6-(1H-pyrazol-3-ylamino)pyrazin-2-yl)methyl)cyclohexanecarboxamide;
(f) 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazol-2(3H)-one;
(g) 5-(trans-4-(3-chloro-2-fluorophenoxy)-1-((6-(1H-pyrazol-3-ylamino)pyridin-2-yl)methyl)cyclohexyl)-1,3,4-oxadiazol-2(3H)-one;
(h) 5-(trans-4-(3-chloro-2-fluorophenoxy)-1-((6-(1H-pyrazol-3-ylamino)pyrazin-2-yl)methyl)cyclohexyl)-1,3,4-oxadiazol-2(3H)-one;

(i) 5-(trans-4-((2,3-dichlorophenyl)sulfonyl)-1-((6-(1H-pyrazol-3-ylamino)pyridin-2-yl)methyl)cyclohexyl)-1,3,4-oxadiazol-2(3H)-one,
(j) trans-1-((4-bromo-6-(1,3-thiazol-2-ylamino)pyridin-2-yl)methyl)-4-(3-chloro-2-fluorophenoxy)cyclohexanecarboxylic acid,
(k) 5-(trans-4-(3-chloro-2-fluorophenoxy)-1-((4-methyl-6-(1H-pyrazol-3-ylamino)pyrimidin-2-yl)methyl)cyclohexyl)-1,3,4-oxadiazol-2(3H)-one, or
(l) 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazole-2(3H)-thione, or a pharmaceutically acceptable salt or ester thereof; and the other preparation is a preparation containing paclitaxel or docetaxel, or a pharmaceutically acceptable salt or ester thereof, together with a pharmaceutically acceptable carrier or diluent.

Moreover, the combined preparation comprising, together with a pharmaceutically acceptable carrier or diluent, two separate preparations according to the invention may be further combined with at least one preparation containing an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined above), or a pharmaceutically acceptable salt or ester thereof.

Also, the pharmaceutical composition according to the invention preferably contains, together with a pharmaceutically acceptable carrier or diluent, the following:
(a) trans-4-(3-chloro-2-fluorophenoxy)-1-((6-(1,3-thiazol-2-ylamino)pyridin-2-yl)methyl)cyclohexanecarboxylic acid;
(b) trans-4-(2-fluoro-3-(trifluoromethyl)phenoxy)-1-((6-(1,3-thiazol-2-ylamino)pyridin-2-yl)methyl)cyclohexanecarboxylic acid;
(c) trans-4-(2,3-dichlorophenoxy)-1-((6-(1,3-thiazol-2-ylamino)pyridin-2-yl)methyl)cyclohexanecarboxylic acid;
(d) trans-4-(2-fluoro-3-(trifluoromethyl)phenoxy)-1-((6-(1H-pyrazol-3-ylamino)pyridin-2-yl)methyl)cyclohexanecarboxylic acid;
(e) trans-4-(3-chloro-2-fluorophenoxy)-1-((6-(1H-pyrazol-3-ylamino)pyrazin-2-yl)methyl)cyclohexanecarboxamide;
(f) 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazol-2(3H)-one;
(g) 5-(trans-4-(3-chloro-2-fluorophenoxy)-1-((6-(1H-pyrazol-3-ylamino)pyridin-2-yl)methyl)cyclohexyl)-1,3,4-oxadiazol-2(3H)-one;
(h) 5-(trans-4-(3-chloro-2-fluorophenoxy)-1-((6-(1H-pyrazol-3-ylamino)pyrazin-2-yl)methyl)cyclohexyl)-1,3,4-oxadiazol-2(3H)-one;
(i) 5-(trans-4-((2,3-dichlorophenyl)sulfonyl)-1-((6-(1H-pyrazol-3-ylamino)pyridin-2-yl)methyl)cyclohexyl)-1,3,4-oxadiazol-2(3H)-one,
(j) trans-1-((4-bromo-6-(1,3-thiazol-2-ylamino)pyridin-2-yl)methyl)-4-(3-chloro-2-fluorophenoxy)cyclohexanecarboxylic acid,
(k) 5-(trans-4-(3-chloro-2-fluorophenoxy)-1-((4-methyl-6-(1H-pyrazol-3-ylamino)pyrimidin-2-yl)methyl)cyclohexyl)-1,3,4-oxadiazol-2(3H)-one, or
(l) 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazole-2(3H)-thione, or a pharmaceutically acceptable salt or ester thereof; and paclitaxel or docetaxel, or a pharmaceutically acceptable salt or ester thereof, together with a pharmaceutically acceptable carrier or diluent.

Description of the process for preparation of compound of General Formula (I)

Among the compounds represented by the General Formula (I):

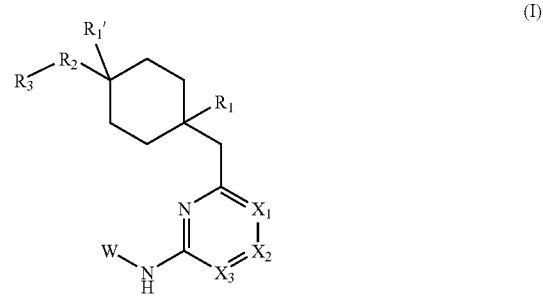

(wherein $R_1$, $R_1'$, $R_2$, $R_3$, $X_1$, $X_2$, $X_3$, and W have the same meaning as the symbols for the above Formula (I)) according to the invention, the compound of Formula (I-1):

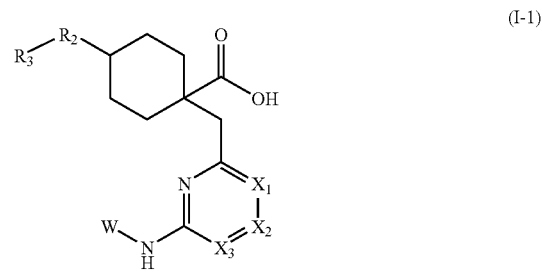

(wherein $R_1$ is COOH; $R_1'$ is a hydrogen atom; $R_2$ is O or S; $R_3$, $X_1$, $X_2$, $X_3$, and W have the same meaning as the symbols for the above Formula (I)) can be prepared by, for example, the following method. Hereinafter, the phrase "symbols for the above Formula (I)" as used herein means "the respective symbols as described for General Formula (I) initially described in the present specification."

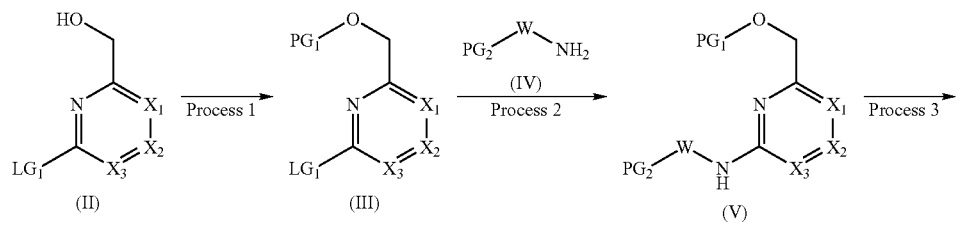

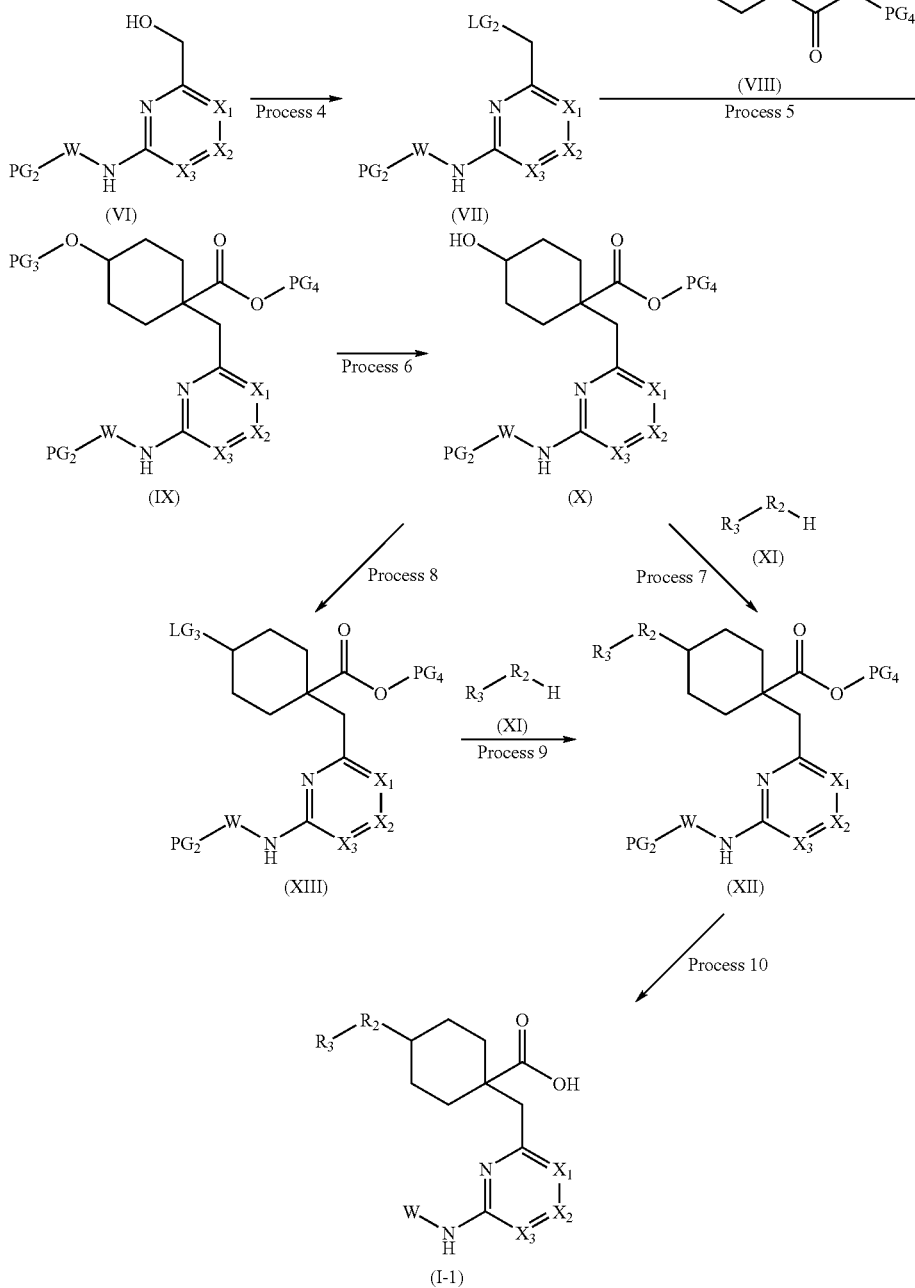

(Process 1) The present process is a method of introducing a protective group $PG_1$ such as a tert-butyldimethylsilyl group to Compound (II) (wherein $LG_1$ represents a leaving group such as halogen, and $X_1$, $X_2$, and $X_3$ have the same meaning as the symbols for the above Formula (I)), thereby to produce Compound (III) (wherein $LG_1$ and $PG_1$ have the same meaning as defined above, and $X_1$, $X_2$, and $X_3$ have the same meaning as the symbols for the above Formula (I)).

The Compound (II) used in this process may be exemplified by (6-bromopyridin-2-yl)methanol, (4-chloropyridin-2-yl)methanol, and the like. The Compound (II) is commercially available or can be prepared by a known method.

As to the protective group $PG_1$, a method of protection may vary depending on the type of the protective group, but methods described in the literature [See T. W. Greene, *Protective Groups in Organic Synthesis*, John Wiley & Sons (1981)] or methods equivalent thereto can be utilized. For example, the Compound (II) can be protected by using tert-butyldimethylsilyl chloride in a solvent such as N,N-dimethylformamide in the presence of a base such as imidazole. When tert-butyldimethylsilyl chloride is used for a protection reaction, tert-butyldimethylsilyl chloride is used in an amount of from 1 to 10 mol, preferably from 1 to 3 mol, and the base is used in an amount of from 1 to 20 mol, preferably from 1 to 5 mol, relative to 1 mol of Compound (II). In this case, the reaction temperature may be appropriately selected by a person skilled in the art in accordance with the starting compound or reaction solvent used, but it is typically from 0° C. to the boiling point of the solvent. Also, the reaction is typically completed between 1 hour to 24 hours, but the reaction time can be appropriately extended or reduced.

The resulting Compound (III) is subjected to isolation and purification by known separation and purification means such as, for example, concentration, concentration under reduced pressure, crystallization, solvent extraction, reprecipitation or chromatography, or may be subjected to the next process without isolation and purification.

(Process 2) The present process is a method of subjecting the Compound (III) (wherein $LG_1$ and $PG_1$ have the same meaning as defined above, and $X_1$, $X_2$, and $X_3$ have the same meaning as the symbols for the above Formula (I)), obtained in the above-described Process 1, and Compound (IV) (wherein $PG_2$ may be absent, or if present, it is a protective group such as 4-methoxybenzyl, 2,4-dimethoxybenzyl, benzyl, methoxymethyl, (2-(trimethylsilyl)ethoxy)methyl or tert-butyl, preferably (2-(trimethylsilyl)ethoxy)methyl, methoxymethyl or tert-butyl, and W has the same meaning as the symbol for the above Formula (I)), to an amination reaction, thereby to produce Compound (V) (wherein $PG_1$ and $PG_2$ have the same meaning as defined above, and $X_1$, $X_2$, $X_3$, and W have the same meaning as the symbols for the above Formula (I)).

The Compound (IV) used in this process may be exemplified by 2-aminothiazol-5-carbonitrile, 2-aminothiazole, 2-amino-5-methylthiazole, 5-amino-1,2,4-thiadiazole, 5-methyl-1-((2-(trimethylsilyl)ethoxy)methyl)-1H-pyrazol-3-amine, 1-((2-(trimethylsilyl)ethoxy)methyl)-1H-pyrazol-3-amine, 1-tert-butyl-3-methyl-1H-pyrazol-5-amine, and the like. The Compound (IV) is commercially available or can be prepared by a known method (e.g., *Phosphorus, Sulfur and Silicon and the Related Elements*, Vol. 177, No. 11, pages 2651-2659 (2002), and *Journal of Chemical Research, Synopses*, Vol.6, page 198 (1979)).

The amination reaction used in this process employs a method well known to those skilled in the art. The amination reaction, for example, can be carried out in accordance with a method described in Organic Letter (2002), Vol. 4, 3484. In the amination reaction used in the process, specifically, for example, synthesis can be conducted by reacting the Compound (III) and Compound (IV) in a solvent such as 1,4-dioxane, 1,2-dimethoxyethane, tetrahydrofuran, methylene chloride, chloroform or toluene, using a palladium catalyst such as trisdibenzylideneacetone dipalladium (0) or palladium acetate; a ligand such as 2,2'-bisdiphenylphosphino-1,1'-binaphthyl or 4,5-bis(diphenylphosphino)-9,9-dimethylxanthene; and a base such as cesium carbonate or sodium t-butoxide. In the reaction, 0.5 to 3 mol, preferably 1 mol, of Compound (IV) is used; 0.001 to 1 mol, preferably 0.05 to 0.5 mol, of the palladium catalyst is used; 0.002 to 2 mol, preferably 0.1 to 1.0 mol, of the ligand is used; and 1 to 10 mol, preferably 1 to 3 mol, of the base is used, relative to 1 mol of compound (III). The reaction temperature is appropriately selected by a person skilled in the art in accordance with the starting compound or reaction solvent used, but it is typically from 50° C. to the boiling point of the solvent used in the reaction. Also, the reaction is typically completed between 1 hour to 24 hours, but the reaction time can be appropriately extended or reduced.

The resulting Compound (V) is subjected to isolation and purification by known separation and purification means such as, for example, concentration, concentration under reduced pressure, crystallization, solvent extraction, reprecipitation or chromatography, or maybe subjected to the next process without isolation and purification.

(Process 3) The present process is a method of deprotecting a protecting group $PG_1$ of Compound (V) (wherein $PG_1$ and $PG_2$ have the same meaning as defined above, and $X_1$, $X_2$, $X_3$, and W have the same meaning as the symbols for the above Formula (I)), obtained in the above-described Process 2, thereby to produce Compound (VI) (wherein $PG_2$ has the same meaning as defined above, and $X_1$, $X_2$, $X_3$, and W have the same meaning as the symbols for the above Formula (I)).

For removal of the protective group $PG_1$ used in this process, the method of removal may vary depending on the type of the protective group and stability of the compound, but methods described in the literature [See T. W. Greene, *Protective Groups in Organic Synthesis*, John Wiley & Sons (1981)] or methods equivalent thereto can be carried out. For example, the Compound (V) in which $PG_1$ is tert-butyldimethylsilyl can be deprotected in a solvent such as tetrahydrofuran using tetrabutylammonium fluoride, or the like. When tetrabutylammonium fluoride is used for the deprotection reaction, tetrabutylammonium fluoride is used in an amount of from 1 to 10 mol, preferably from 1 to 3 mol, relative to 1 mol of Compound (V). The reaction temperature can be appropriately selected by a person having ordinary skill in the art in accordance with the starting compound or reaction solvent used, but it is typically from 0° C. to the boiling point of the solvent. Also, the reaction is typically completed between 1 hour to 24 hours, but the reaction time can be appropriately extended or reduced.

The resulting Compound (VI) is subjected to isolation and purification by known separation and purification means such as, for example, concentration, concentration under reduced pressure, crystallization, solvent extraction, reprecipitation or chromatography, or may be subjected to the next process without isolation and purification.

(Process 4) The present process is a method of converting a hydroxy group of Compound (VI) obtained in the above-described Process 3 (wherein $PG_2$ has the same meaning as defined above, and $X_1$, $X_2$, $X_3$, and W have the same meaning as the symbols for the above Formula (I)) to a leaving group such as methylsulfonyloxy, chloro, or bromo, thereby to produce Compound (VII) (wherein $LG_2$ represents a leaving group such as methylsulfonyloxy or halogen atom, $PG_2$ has the same meaning as defined above, and $X_1$, $X_2$, $X_3$, and W have the same meaning as the symbols for the above Formula (I)).

The reaction used in this process employs methods well known to those skilled in the art. In the reaction used in this process, specifically, for example, Compound (VII) in which $LG_2$ is methylsulfonyloxy can be obtained by reacting the Compound (VI) with methanesulfonyl chloride in a solvent such as chloroform, methylene chloride, tetrahydrofuran, N,N-dimethylformamide, diethyl ether or ethyl acetate, in the presence of a base such as triethylamine or diisopropylethylamine. In this case, methanesulfonyl chloride is used in an amount of from 1 to 10 mol, preferably from 1 to 3 mol; and the base is used in an amount of from 1 to 20 mol, preferably from 1 to 6 mol, relative to 1 mol of Compound (VI). The reaction temperature can be appropriately selected by a person having ordinary skill in the art in accordance with the starting compound or reaction solvent used, but it is typically from 0° C. to room temperature. Also, the reaction is typically completed between 10 minutes to 2 hours, but the reaction time can be appropriately extended or reduced.

Also, the Compound (VII) in which $LG_2$ is bromo can be obtained by reacting the Compound (VII) in which $LG_2$ is methylsulfonyloxy, with lithium bromide in a solvent such as N,N-dimethylformamide, N-methyl-2-pyrrolidinone, or the like. In this case, lithium bromide is used in an amount of from 1 to 100 mol, preferably from 1 to 10 mol, relative to 1 mol of Compound (VII) in which $LG_2$ is methylsulfonyloxy. The reaction temperature can be appropriately selected by a person having ordinary skill in the art in accordance with the starting compound or reaction solvent used, but it is typically from 0° C. to the boiling temperature of the solvent. Also, the reaction is typically completed between 1 hour to 24 hours, but the reaction time can be appropriately extended or reduced.

The resulting Compound (VII) is subjected to isolation and purification by known separation and purification means such as, for example, concentration, concentration under reduced pressure, crystallization, solvent extraction, reprecipitation or chromatography, or may be subjected to the next process without isolation and purification.

(Process 5) The present process is a method of subjecting the Compound (VII) (wherein $LG_2$ and $PG_2$ have the same meaning as defined above, and $X_1$, $X_2$, $X_3$, and W have the same meaning as the symbols for the above Formula (I)), obtained in the above-described Process 4, and Compound (VIII) (wherein $PG_3$ is a protecting group such as tert-butyl (dimethyl)silyl or tert-butyl(diphenyl)silyl, and $PG_4$ is a protecting group such as methyl, ethyl, or tert-butyl), to an alkylation reaction, thereby to produce Compound (IX) (wherein $PG_2$, $PG_3$ and $PG_4$ have the same meaning as defined above, and $X_1$, $X_2$, $X_3$, and W have the same meaning as the symbols for the above Formula (I)).

The Compound (VIII) used in this process may be exemplified by tert-butyl 4-((tert-butyl(diphenyl)silyl)oxy)cyclohexanecarboxylate, ethyl 4-((tert-butyl(dimethyl)silyl)oxy) cyclohexanecarboxylate, and the like. The Compound (VIII) can be prepared using ethyl 4-hydroxycyclohexanecarboxylate in accordance with a known protecting or deprotecting method [Protective Groups in Organic Synthesis, T. W. Greene, John Wiley & Sons (1981)].

The alkylation reaction used in this process employs methods well known to those skilled in the art. In the amination reaction used in this process, specifically, for example, the Compound (IX) can be synthesized by reacting the Compound (VIII) in a solvent such as tetrahydrofuran with a base such as lithium diisopropylamide or lithium hexamethyldisilazide to produce an enolate form of the Compound (IX), followed by adding thereto the Compound (VII) and if necessary an additive such as hexamethylphosphoric triamide or 1,3-dimethyl-2-imidazolidinone, and the like, thereby to produce the Compound (IX). In this reaction, Compound (VIII) is used in an amount of from 1 to 10 mol. preferably from 1 to 3 mol; and the base is used in an amount of from 1 to 10 mol. preferably from 1 to 3 mol; and the additive is used in an amount of from 1 to 100 mol, preferably from 1 to 10 mol, relative to 1 mol of Compound (VII). The reaction temperature can be appropriately selected by a person having ordinary skill in the art in accordance with the starting compound or reaction solvent used, but it is typically from −78° C. to room temperature. Also, the reaction is typically completed within 1 hour to 48 hours, but the reaction time can be appropriately extended or reduced.

The resulting Compound (IX) is subjected to isolation and purification by known separation and purification means such as, for example, concentration, concentration under reduced pressure, crystallization, solvent extraction, reprecipitation or chromatography, or may be subjected to the next process without isolation and purification.

(Process 6) The present process is a method of deprotecting a protective group $PG_3$ of the Compound (IX) (wherein $PG_2$, $PG_3$ and $PG_4$ have the same meaning as defined above, and $X_1$, $X_2$, $X_3$, and W have the same meaning as the symbols for the above Formula (I)), obtained in the above-described Process 5, thereby to produce Compound (X) (wherein $PG_2$ and $PG_4$ have the same meaning as defined above, and $X_1$, $X_2$, $X_3$, and W have the same meaning as the symbols for the above Formula (I)).

For the deprotection reaction of $PG_3$, the method may vary depending on the type of the protective group or stability of the compound, but methods described in the literature [See T. W. Greene, *Protective Groups in Organic Synthesis*, John Wiley & Sons (1981)] or methods equivalent thereto can be carried out. For example, the Compound (IX) in which $PG_3$ is tert-butyl(diphenyl)silyl can be deprotected using tetrabutylammonium fluoride in a solvent such as tetrahydrofuran, or the like. When tetrabutylammonium fluoride is used for the deprotection reaction, tetrabutylammonium fluoride is used in an amount of from 1 to 10 mol, preferably from 1 to 5 mol, relative to 1 mol of Compound (IX). The reaction temperature can be appropriately selected by a person having ordinary skill in the art in accordance with the starting compound or reaction solvent used, but it is typically from 0° C. to the boiling point of the solvent. Also, the reaction is typically completed between 1 hour to 24 hours, but the reaction time can be appropriately extended or reduced.

The resulting Compound (X) is subjected to isolation and purification by known separation and purification means such as, for example, concentration, concentration under reduced pressure, crystallization, solvent extraction, reprecipitation or chromatography, or may be subjected to the next process without isolation and purification.

(Process 7) The present process is a method of reacting the Compound (X) (wherein $PG_2$ and $PG_4$ have the same meaning as defined above, and $X_1$, $X_2$, $X_3$, and W have the same meaning as the symbols for the above Formula (I)), obtained in the above-described Process 6, with Compound (XI) (wherein $R_2$ is O or S; and $R_3$ has the same meaning as the symbols for the above Formula (J)), thereby to produce Compound (XII) (wherein $R_2$ is O or S; $PG_2$ and $PG_4$ have the same meaning as defined above, and $R_3$, $X_1$, $X_2$, $X_3$, and W have the same meaning as the symbols for the above Formula (I)).

The Compound (XI) used in this process is, for example, 3-chloro-2-fluorophenol, 2-fluoro-3-(trifluoromethyl)phenol, 2,3-difluorophenol, 2,3-dichlorothiophenol, and the like. The Compound (XI) is commercially available.

The reaction used in this process employs methods well known to those skilled in the art, for example, the Mitsunobu reaction [Synthesis (1981), 1]. In the Mitsunobu reaction used in this process, specifically, for example, the Compound (XII) can be synthesized by reacting the Compound (X) and the Compound (XI) in a solvent such as tetrahydrofuran, toluene, chloroform or ethyl acetate, with a phosphine compound such as, for example, triphenylphosphine, tributylphosphine, or trifurylphosphine and also with an azo compound such as, for example, diethyl azodicarboxylate, diisopropyl azodicarboxylate, di-tert-butyl azodicarboxylate. In this case, Compound (XI) is used in an amount of from 1 to 10 mol, preferably from 1 to 3 mol; and the phosphine compound is used in an amount of from 1 to 10 mol, preferably from 1 to 3 mol; and the azo compound is used in an amount of from 1 to 10 mol, preferably from 1 to 3 mol, relative to 1 mol of Compound (X). The reaction temperature can be appropriately selected by a person having ordinary skill in the art in accordance with the starting compound or reaction solvent used, but it is typically from 0° C. to the boiling temperature of the solvent. Also, the reaction is typically completed between 1 hour to 24 hours, but the reaction time can be appropriately extended or reduced.

The resulting Compound (XII) is subjected to isolation and purification by known separation and purification means such as, for example, concentration, concentration under reduced pressure, crystallization, solvent extraction, reprecipitation or chromatography, or may be subjected to the next process without isolation and purification.

(Process 8) The present process is a method of converting a hydroxy group of the Compound (X) (wherein $PG_2$ and $PG_4$ have the same meaning as defined above, and $X_1$, $X_2$, $X_3$, and W have the same meaning as the symbols for the above Formula (I)), obtained in the above-described Process 6, into a leaving group such as methylsulfonyloxy, chloro, or bromo, thereby to produce Compound (XIII) (wherein $LG_3$ is a leaving group such as, for example, methylsulfonyloxy, or halogen atom, $PG_2$ and $PG_4$ have the same meaning as defined above, and $X_1$, $X_2$, $X_3$, and W have the same meaning as the symbols for the above Formula (I).

The reaction used in this process employs methods well known to those skilled in the art. The reaction used in this process, specifically, for example, the Compound (XIII) (wherein $LG_3$ is methylsulfonyloxy) can be obtained by reacting the Compound (X) with methanesulfonyl chloride in a solvent such as chloroform, methylene chloride, tetrahydrofuran, N,N-dimethylformamide, diethyl ether, ethyl acetate, in the presence of a base such as triethylamine, or diisopropylethylamine. In this case, methanesulfonyl chloride is used in an amount of from 1 to 10 mol, preferably from 1 to 3 mol; and the base is used in an amount of from 1 to 20 mol, preferably from 1 to 6 mol, relative to 1 mol of Compound (X). The reaction temperature can be appropriately selected by a person having ordinary skill in the art in accordance with the starting compound or reaction solvent used, but it is typically from 0° C. to room temperature. Also, the reaction is typically completed between 10 minutes to 2 hours, but the reaction time can be appropriately extended or reduced.

The resulting Compound (XIII) is subjected to isolation and purification by known separation and purification means such as, for example, concentration, concentration under reduced pressure, crystallization, solvent extraction, reprecipitation or chromatography, or may be subjected to the next process without isolation and purification.

(Process 9) The present process is a method of reacting the Compound (XIII) (wherein $LG_3$, $PG_2$ and $PG_4$ have the same meaning as defined above, and $X_1$, $X_2$, $X_3$, and W have the same meaning as the symbols for the above Formula (I)), obtained in the above-described Process 8, with Compound (XI) (wherein $R_2$ is O or S; and $R_3$ has the same meaning as the symbols for the above Formula (I)), thereby to produce Compound (XII) (wherein $PG_2$ and $PG_4$ have the same meaning as defined above, $R_2$ is O or S, and $X_1$, $X_2$, $X_3$, and W have the same meaning as the symbols for the above Formula (I)).

The Compound (XI) used in this process can be exemplified by 3-chloro-2-fluorophenol, 2-fluoro-3-(trifluoromethyl)phenol, 2,3-difluorophenol, 2,3-dichlorothiophenol. As described before, the Compound (XI) is commercially available.

The reaction used in this process employs a method well known to those skilled in the art. In the reaction used in this process, specifically, for example, synthesis can be conducted by reacting the Compound (XIII) and the Compound (XI) with a base such as potassium carbonate or cesium carbonate, in a solvent such as, for example, N,N-dimethylformamide or N-methyl-2-pyrrolidinone. In this case, Compound (XI) is used in an amount of from 1 to 10 mol, preferably from 1 to 3 mol; and the base is used in an amount of from 1 to 20 mol, preferably from 1 to 5 mol, relative to 1 mol of Compound (XIII). The reaction temperature can be appropriately selected by a person having ordinary skill in the art in accordance with the starting compound or reaction solvent used, but it is typically from room temperature to the boiling temperature of the solvent. Also, the reaction is typically completed between 1 hour to 24 hours, but the reaction time can be appropriately extended or reduced.

The resulting Compound (XII) is subjected to isolation and purification by known separation and purification means such as, for example, concentration, concentration under reduced pressure, crystallization, solvent extraction, reprecipitation or chromatography, or may be subjected to the next process without isolation and purification.

(Process 10) The present process is a method of deprotecting the protective groups $PG_2$ and $PG_4$ of the Compound (XII) (wherein $PG_2$ and $PG_4$ have the same meaning as defined above, $R_2$ is O or S, and $R_3$, $X_1$, $X_2$, $X_3$, and W have the same meaning as the symbols for the above Formula (I)), obtained in the above-described Processes 7 or 9, thereby to produce Compound (I-1) (wherein $R_2$ is O or S, and $R_3$, $X_1$, $X_2$, $X_3$, and W have the same meaning as the symbols for the above Formula (I)).

For the deprotection reaction of $PG_2$ and $PG_4$, the method may vary depending on the type of the protective group or stability of the compound, but methods described in the literature [See T. W. Greene, *Protective Groups in Organic Synthesis*, John Wiley & Sons (1981)] or methods equivalent thereto can be carried out. For example, the Compound (XII) (wherein $PG_2$ is methoxymethyl, and $PG_4$ is tert-butyl) can be deprotected using a hydrogen chloride solution in 1,4-dioxane. When the hydrogen chloride solution in 1,4-dioxane is used for the deprotection reaction, hydrogen chloride is used in an amount of from 1 to 1000 mol, preferably from 10 to 100 mol, relative to 1 mol of Compound (XII). The reaction temperature can be appropriately selected by a person having ordinary skill in the art in accordance with the starting compound or reaction solvent used, but it is typically from room temperature to the boiling point of the solvent. Also, the reaction is typically completed between 1 hour to 24 hours, but the reaction time can be appropriately extended or reduced.

The resulting Compound (I-1) is subjected to isolation and purification by known separation and purification means such as, for example, concentration, concentration under reduced pressure, crystallization, solvent extraction, reprecipitation or chromatography.

The Compound (XII) (wherein $PG_2$ and $PG_4$ have the same meaning as defined above, $R_2$ is O or S, and $R_3$, $X_1$, $X_2$, $X_3$, and W have the same meaning as the symbols for the above Formula (I)) can be produced, for example, by the following method:

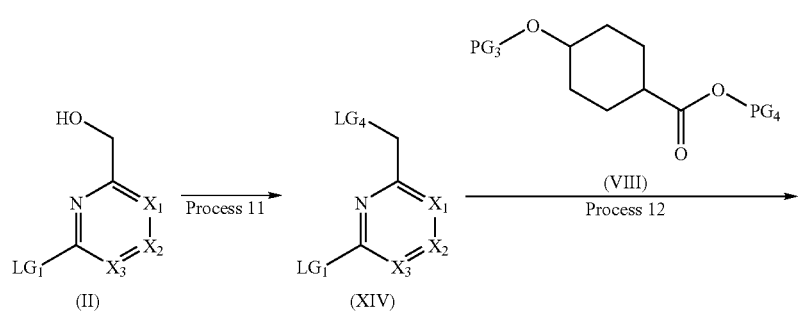

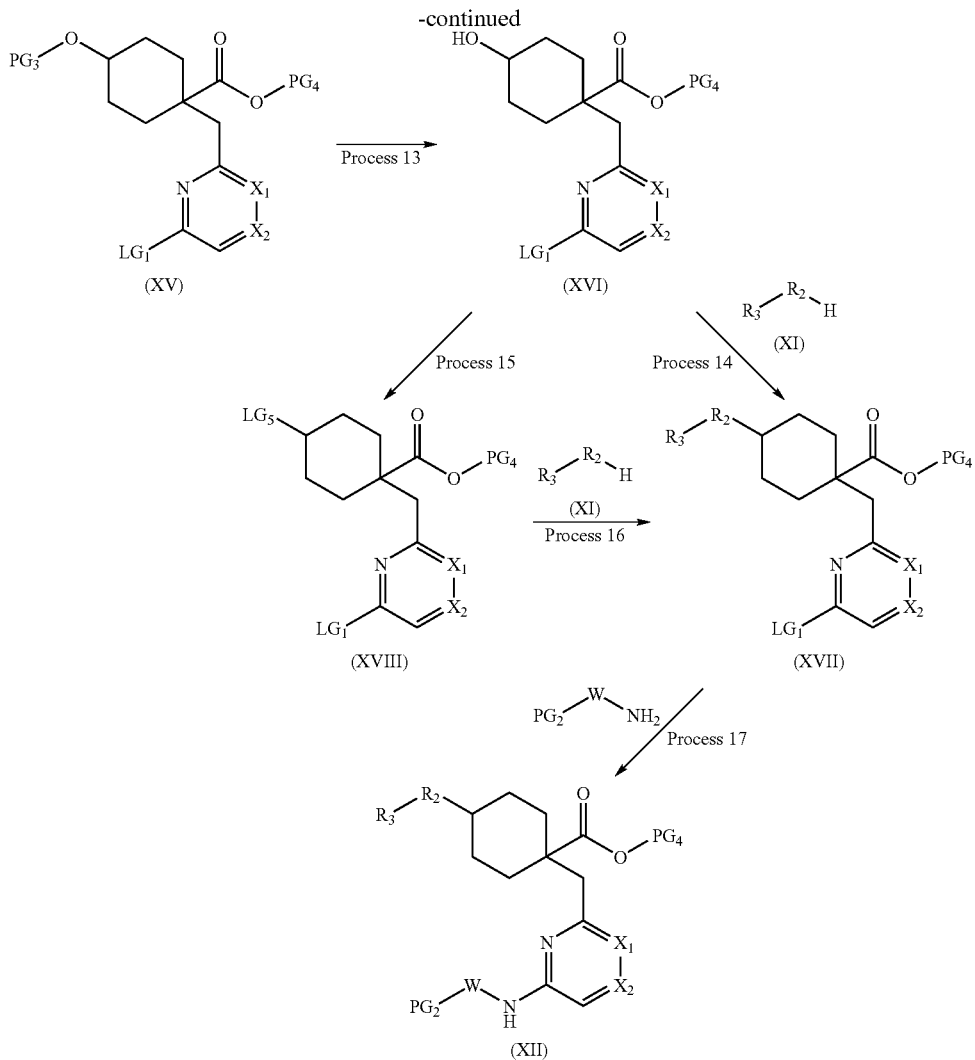

(Process 11) The present process is a method of converting a hydroxy group of the Compound (II) (wherein $LG_1$ is a leaving group such as halogen atom, and $X_1$, $X_2$, and $X_3$ have the same meaning as the symbols for the above Formula (I)), into a leaving group such as, for example, methylsulfonyloxy, chloro, or bromo, thereby to produce Compound (XIV) (wherein $LG_4$ is a leaving group such as, for example, methylsulfonyloxy or halogen atom; $LG_1$ have the same meaning as defined above; and $X_1$, $X_2$, and $X_3$ has the same meaning as the symbols for the above Formula (I)).

The Compound (II) used in this process can be exemplified by (6-bromopyridin-2-yl)methanol, (4-chloropyrazin-2-yl) methanol. The Compound (II) is commercially available or can be produced by a known method.

The present process can be carried out by the same method as used in Process 4, or a method equivalent thereto, or a combination of the same with a commonly used method.

The resulting Compound (XIV) is subjected to isolation and purification by known separation and purification means such as, for example, concentration, concentration under reduced pressure, crystallization, solvent extraction, reprecipitation or chromatography, or may be subjected to the next process without isolation and purification.

(Process 12) The present process is a method of subjecting the Compound (XIV) (wherein $LG_4$ is a leaving group such as methylsulfonyloxy, halogen atom, and the like, $LG_1$ has the same meaning as defined above, and $X_1$, $X_2$, and $X_3$ have the same meaning as the symbols for the above Formula (I)), obtained in the above-described Process 11, and Compound (VIII) (wherein $PG_3$ is a protecting group such as tert-butyl (dimethyl)silyl or tert-butyl(diphenyl)silyl, and $PG_4$ is a protecting group such as methyl, ethyl, tert-butyl, and the like), to an alkylation reaction, thereby to produce Compound (XV) (wherein $LG_1$, $PG_3$ and $PG_4$ have the same meaning as defined above, and $X_1$, $X_2$, and $X_3$ have the same meaning as the symbols for the above Formula (I)).

The Compound (VIII) used in this process may be exemplified by tert-butyl 4-((tert-butyl(diphenyl)silyl)oxy)cyclohexanecarboxylate, ethyl 4-((tert-butyl(dimethyl)silyl)oxy) cyclohexanecarboxylate. The Compound (VIII) can be prepared using ethyl 4-hydroxycyclohexanecarboxylate in accordance with a known protecting or deprotecting method [Protective Groups in Organic Synthesis, T. W. Greene, John Wiley & Sons (1981)].

The present process can be carried out by the same method as used in Process 5, or a method equivalent thereto, or a combination of the same with a commonly used method.

The resulting Compound (XV) is subjected to isolation and purification by known separation and purification means such as, for example, concentration, concentration under reduced pressure, crystallization, solvent extraction, reprecipitation or chromatography, or may be subjected to the next process without isolation and purification.

(Process 13) The present process is a method of deprotecting the protective group $PG_3$ of the Compound (XV) (wherein $LG_1$, $PG_3$ and $PG_4$ have the same meaning as defined above, and $X_1$, $X_2$, and $X_3$ have the same meaning as the symbols for the above Formula (I)), obtained in the above-described Process 12, thereby to produce Compound (XVI) (wherein $LG_1$ and $PG_4$ have the same meaning as defined above, and $X_1$, $X_2$, and $X_3$ have the same meaning as the symbols for the above Formula (I)).

The present process can be carried out by the same method as used in Process 6, or a method equivalent thereto, or a combination of the same with a commonly used method.

The Compound (XVI) is subjected to isolation and purification by known separation and purification means such as, for example, concentration, concentration under reduced pressure, crystallization, solvent extraction, reprecipitation or chromatography, or may be subjected to the next process without isolation and purification.

(Process 14) The present process is a method of reacting Compound (XVI) (wherein $LG_1$ and $PG_4$ have the same meaning as defined above, and $X_1$, $X_2$, and $X_3$ have the same meaning as the symbols for the above Formula (I)), obtained in the above-described Process 13, with Compound (XI) (wherein $R_2$ is O or S; and $R_3$ has the same meaning as the symbols for the above Formula (I)), thereby to produce Compound (XVII) (wherein $LG_1$ and $PG_4$ have the same meaning as defined above; $R_2$ is O or S; and $R_3$, $X_1$, $X_2$, and $X_3$ have the same meaning as the symbols for the above Formula (I)).

The Compound (XI) used in this process is, for example, 3-chloro-2-fluorophenol, 2-fluoro-3-(trifluoromethyl)phenol, 2,3-difluorophenol, 2,3-dichlorothiophenol, and the like. As mentioned above, the Compound (XI) is commercially available.

The present process can be carried out by the same method as used in Process 7, or a method equivalent thereto, or a combination of the same with a commonly used method.

The resulting Compound (XVII) is subjected to isolation and purification by known separation and purification means such as, for example, concentration, concentration under reduced pressure, crystallization, solvent extraction, reprecipitation or chromatography, or may be subjected to the next process without isolation and purification.

(Process 15) The present process is a method of converting a hydroxy group of the Compound (XVI) (wherein $LG_1$ and $PG_4$ have the same meaning as defined above, and $X_1$, $X_2$, and $X_3$ have the same meaning as the symbols for the above Formula (I)) obtained in the above-described Process 13, into a leaving group such as, for example, methylsulfonyloxy, chloro, or bromo, thereby to produce Compound (XVIII) (wherein $LG_5$ is a leaving group such as, for example, methylsulfonyloxy or halogen atom; $LG_1$ and $PG_4$ have the same meaning as defined above; and $X_1$, $X_2$, and $X_3$ have the same meaning as the symbols for the above Formula (I)).

The present process can be carried out by the same method as used in Process 8, or a method equivalent thereto, or a combination of the same with a commonly used method.

The resulting Compound (XVIII) is subjected to isolation and purification by known separation and purification means such as, for example, concentration, concentration under reduced pressure, crystallization, solvent extraction, reprecipitation or chromatography, or may be subjected to the next process without isolation and purification.

(Process 16) The present process is a method of reacting the Compound (XVIII) (wherein $LG_5$ is a leaving group such as, for example, methylsulfonyloxy or halogen atom; $LG_1$ and $PG_4$ have the same meaning as defined above; and $X_1$, $X_2$, and $X_3$ have the same meaning as the symbols for the above Formula (I)), obtained in the above-described Process 15, with Compound (XI) (wherein $R_2$ is O or S; and $R_3$ has the same meaning as the symbols for the above Formula (I)), thereby to produce Compound (XVII) (wherein $LG_1$ and $PG_4$ have the same meaning as defined above, $R_2$ is O or S, and $R_3$, $X_1$, $X_2$, and $X_3$ have the same meaning as the symbols for the above Formula (I)).

The Compound (XI) used in this process can be exemplified by 3-chloro-2-fluorophenol, 2-fluoro-3-(trifluoromethyl)phenol, 2,3-difluorophenol, 2,3-dichlorothiophenol. As described before, the Compound (XI) is commercially available.

The present process can be carried out by the same method as used in Process 9, or a method equivalent thereto, or a combination of the same with a commonly used method.

The resulting Compound (XVII) is subjected to isolation and purification by known separation and purification means such as, for example, concentration, concentration under reduced pressure, crystallization, solvent extraction, reprecipitation or chromatography, or may be subjected to the next process without isolation and purification.

(Process 17) The present process is a method of subjecting Compound (XVII) (wherein $LG_1$ and $PG_4$ have the same meaning as defined above, $R_2$ is O or S; and $R_3$, $X_1$, $X_2$, and $X_3$ have the same meaning as the symbols for the above Formula (I)), obtained by the above-described Processes 14 or 16, and Compound (IV) (wherein $PG_2$ may be absent, or if present, it is a protective group such as 4-methoxybenzyl, 2,4-dimethoxybenzyl, benzyl, methoxymethyl, (2-(trimethylsilyl)ethoxy)methyl or tert-butyl, preferably (2-(trimethylsilyl)ethoxy)methyl, methoxymethyl or tert-butyl, and W has the same meaning as the symbol for the above Formula (I)), to an amination reaction, thereby to produce Compound (XII) (wherein $PG_2$ and $PG_4$ have the same meaning as defined above; $R_2$ is O or S; and $R_3$, and $X_1$, $X_2$, $X_3$, and W have the same meaning as the symbols for the above Formula (I)).

The Compound (IV) used in this process may be exemplified by 2-aminothiazol-5-carbonitrile, 2-aminothiazole, 2-amino-5-methylthiazole, 5-amino-1,2,4-thiadiazole, 5-methyl-1-((2-(trimethylsilyl)ethoxy)methyl)-1H-pyrazol-3-amine, 1-((2-(trimethylsilyl)ethoxy)methyl)-1H-pyrazol-3-amine, 1-tert-butyl-3-methyl-1H-pyrazol-5-amine, and the like. The Compound (IV) is commercially available or can be prepared by a known method (e.g., *Phosphorus, Sulfur and Silicon and the Related Elements*, Vol. 177, No. 11, pages 2651-2659 (2002), and *Journal of Chemical Research, Synopses*, Vol. 6, page 198 (1979)).

The present process can be carried out by the same method as used in Process 2, or a method equivalent thereto, or a combination of the same with a commonly used method.

The resulting Compound (XII) is subjected to isolation and purification by known separation and purification means such as, for example, concentration, concentration under reduced pressure, crystallization, solvent extraction, reprecipitation or chromatography, or may be subjected to the next process without isolation and purification.

The Compound (VI) (wherein $PG_2$ has the same meaning as defined above, and $X_1$, $X_2$, $X_3$, and W have the same meaning as the symbols for the above Formula (I)) can be prepared, for example, by the following method:

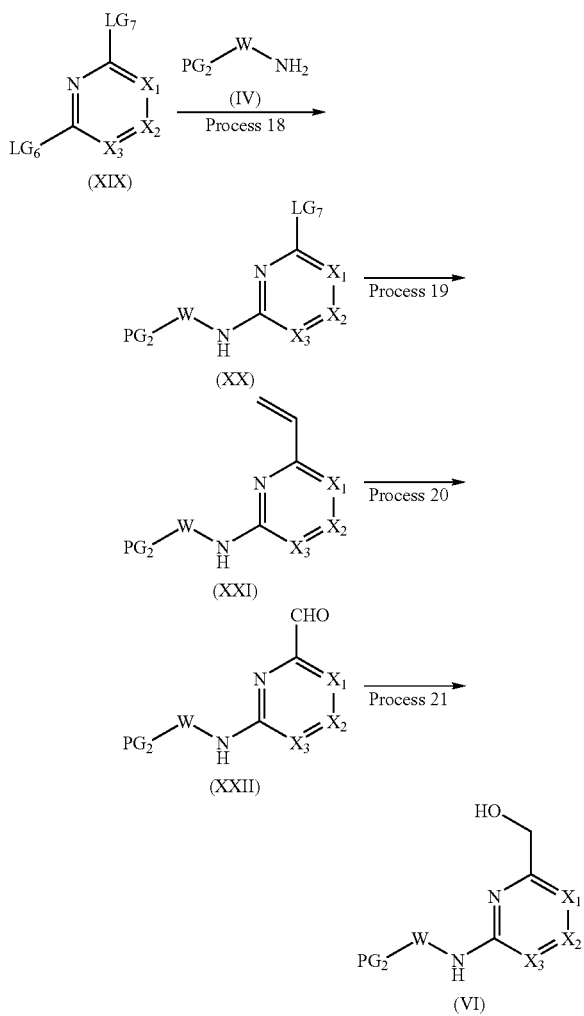

(Process 18) The present process is a method of subjecting Compound (XIX) (wherein LG$_6$ and LG$_7$ is a leaving group such as halogen atom, and X$_1$, X$_2$, and X$_3$ have the same meaning as the symbols for the above Formula (I)) and Compound (IV) (wherein PG$_2$ may be absent, or if present, it is a protective group such as 4-methoxybenzyl, 2,4-dimethoxybenzyl, benzyl, methoxymethyl, (2-(trimethylsilyl)ethoxy)methyl or tert-butyl, preferably (2-(trimethylsilyl)ethoxy)methyl, methoxymethyl or tert-butyl, and W has the same meaning as the symbol for the above Formula (I)) to an amination reaction, thereby to produce Compound (XX) (wherein PG$_2$ and PG$_7$ have the same meaning as defined above, and X$_1$, X$_2$, and X$_3$ have the same meaning as the symbols for the above Formula (I)).

The Compound (IV) used in this process may be exemplified by 2-aminothiazol-5-carbonitrile, 2-aminothiazole, 2-amino-5-methylthiazole, 5-amino-1,2,4-thiadiazole, 5-methyl-1-((2-(trimethylsilyl)ethoxy)methyl)-1H-pyrazol-3-amine, 1-((2-(trimethylsilyl)ethoxy)methyl)-1H-pyrazol-3-amine, 1-tert-butyl-3-methyl-1H-pyrazol-5-amine, and the like. The Compound (IV) is commercially available or can be prepared by known methods (e.g., *Phosphorus, Sulfur and Silicon and the Related Elements*, Vol. 177, No. 11, pages 2651-2659 (2002), and *Journal of Chemical Research, Synopses*, Vol. 6, page 198 (1979)).

The present process can be carried out by the same method as used in Process 2, or a method equivalent thereto, or a combination of the same with a commonly used method.

The resulting Compound (XX) is subjected to isolation and purification by known separation and purification means such as, for example, concentration, concentration under reduced pressure, crystallization, solvent extraction, reprecipitation or chromatography, or may be subjected to the next process without isolation and purification.

(Process 19) The present process is a method of subjecting Compound (XX) (wherein PG$_2$ and LG$_7$ have the same meaning as defined above, and X$_1$, X$_2$, X$_3$, and W have the same meaning as the symbols for the above Formula (I)), obtained in the above Process 18, to a vinylation reaction, thereby to produce Compound (XXI) (wherein PG$_2$ has the same meaning as defined above, and X$_1$, X$_2$, X$_3$, and W have the same meaning as the symbols for the above Formula (I)).

The vinylation reaction used in this process employs a method well known to a person skilled in the art. The reaction can be carried out in accordance with a method disclosed in literature; for example, Organic Letters, (2002), Vol. 4, Page 107. In the vinylation reaction used in this process, specifically, for example, the Compound (XXI) can be synthesized by reacting the Compound (XX) with potassium vinyltrifluoroborate in a solvent such as 1-propanol in the presence of a palladium catalyst such as, for example, 1,1'-bis(diphenylphosphino)ferrocenedichloropalladium (II) methylene chloride complex, and also with a base such as, for example, triethylamine. In this case, the palladium catalyst is used in an amount of from 0.001 to 1 mol, preferably from 0.01 to 0.5 mol; the base is used in an amount of from 1 to 10 mol, preferably from 1 to 5 mol; and the vinylating agent is used in an amount of from 1 to 10 mol, preferably from 1 to 3 mol, relative to 1 mol of Compound (XX). The reaction temperature can be appropriately selected by a person having ordinary skill in the art in accordance with the starting compound or reaction solvent used, but it is typically from room temperature to the boiling point of the solvent. Also, the reaction is typically completed between 1 hour to 24 hours, but the reaction time can be appropriately extended or reduced.

The resulting Compound (XXI) is subjected to isolation and purification by known separation and purification means such as, for example, concentration, concentration under reduced pressure, crystallization, solvent extraction, reprecipitation or chromatography, or may be subjected to the next process without isolation and purification.

(Process 20) The present process is a method of subjecting the Compound (XXI) (wherein PG$_2$ has the same meaning as defined above, and X$_1$, X$_2$, X$_3$, and W have the same meaning as the symbols for the above Formula (I)), obtained in the above Process 19, to an oxidative cleavage reaction, thereby to produce Compound (XXII) (wherein PG$_2$ has the same meaning as defined above, and X$_1$, X$_2$, X$_3$, and W have the same meaning as the symbols for the above Formula (I)).

The oxidative cleavage reaction used in this process employs a method well known to a person skilled in the art. The reaction can be carried out in accordance with a method disclosed in literature; for example, Chemical Reviews (2002), Vol. 87, Page 187; and Tetrahedron Letters (1983) Vol. 24, Page 1377). In the oxidative cleavage reaction used in this process, specifically, for example, first, the Compound (XXI) is reacted with an aqueous solution of osmium tetraoxide and a co-oxidant such as N-methylmorphorine N-oxide, in a solvent such as acetonitrile, to obtain the 1,2-diol form; and then the resulting 1,2-diol form is reacted with an oxidant such as sodium peridodate in a mixed solvent of acetonitrile and water, thereby to produce the Compound (XXII). Here, in the former reaction, osmium tetraoxide is used in an amount of from 0.01 to 1 mol, preferably from 0.1 to 0.5 mol; the co-oxidant is used in an amount of from 1 to 10 mol, preferably from 1 to 3 mol. On the other hand, in the latter reaction, with regard to 1 mol of the 1,2-diol form, the oxidant is used in an amount of from 1 to 10 mol, preferably from 1 to 3 mol, relative to 1 mol of Compound (XXI). The reaction temperature can be appropriately selected by a person having ordinary skill in the art in accordance with the starting compound or reaction solvent used, but it is typically from 0° C. to the boiling point of the solvent. Also, the reaction is typically completed between 1 hour to 24 hours, but the reaction time can be appropriately extended or reduced.

The resulting Compound (XXII) is subjected to isolation and purification by known separation and purification means such as, for example, concentration, concentration under reduced pressure, crystallization, solvent extraction, reprecipitation or chromatography, or may be subjected to the next process without isolation and purification.

(Process 21) The present process is a method of subjecting Compound (XXII) (wherein $PG_2$ has the same meaning as defined above, and $X_1$, $X_2$, $X_3$, and W have the same meaning as the symbols for the above Formula (I)), obtained in the above Process 20, to a reduction reaction, thereby to produce Compound (VI) (wherein $PG_2$ has the same meaning as defined above, and $X_1$, $X_2$, $X_3$, and W have the same meaning as the symbols for the above Formula (I)).

The reduction reaction used in this process employs a method well known to a person skilled in the art. In the reduction reaction used in this process, specifically, for example, the Compound (VI) can be synthesized by reacting the Compound (XXII) with a reducing agent such as sodium borohydride, in a solvent such as methanol, ethanol, or the like. In this case, the reducing agent is used in an amount of from 1 to 10 mol, preferably from 1 to 3 mol, relative to 1 mol of Compound (XXII). The reaction temperature can be appropriately selected by a person having ordinary skill in the art in accordance with the starting compound or reaction solvent used, but it is typically from 0° C. to the boiling point of the solvent. Also, the reaction is typically completed between 10 minutes to 24 hours, but the reaction time can be appropriately extended or reduced.

The resulting Compound (XXII) is subjected to isolation and purification by known separation and purification means such as, for example, concentration, concentration under reduced pressure, crystallization, solvent extraction, reprecipitation or chromatography, or may be subjected to the next process without isolation and purification.

Among the compounds represented by the General Formula (I) (wherein $R_1$, $R_1'$, $R_2$, $R_3$, $X_1$, $X_2$, $X_3$, and W have the same meaning as defined in the above) according to the invention, the compound of Formula (I-2):

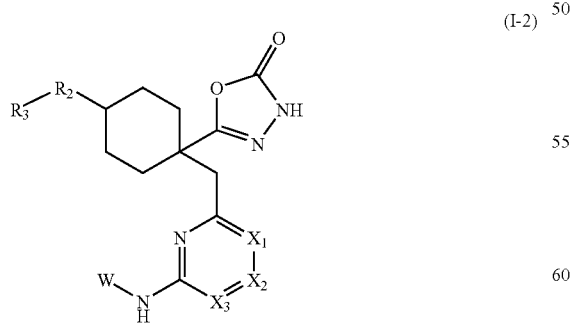

(wherein $R_1$ is 1,3,4-oxadiazol-2(3H)-one; $R_2$ is O or S; $R_1'$ is a hydrogen atom; $R_3$, $X_1$, $X_2$, $X_3$, and W have the same meaning as the symbols for the above Formula (I)) can be prepared by, for example, the following method.

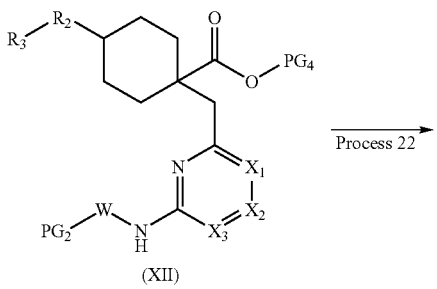
(XII)

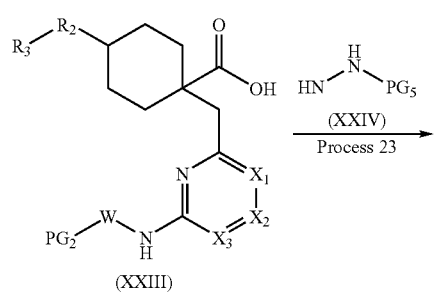
(XXIII)

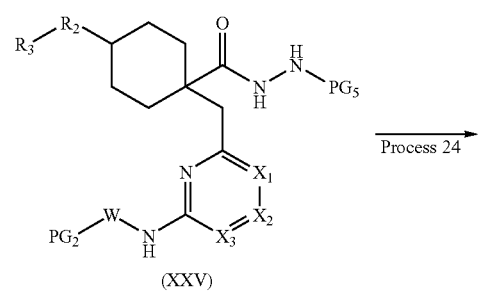
(XXV)

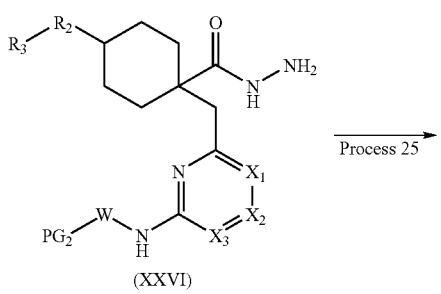
(XXVI)

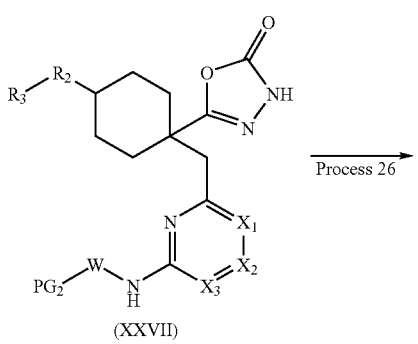
(XXVII)

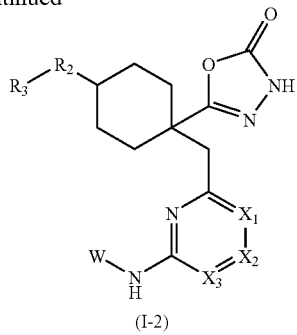

(Process 22) The present process is a method of deprotecting the protective group $PG_4$ of Compound (XII) (wherein $PG_2$ and $PG_4$ have the same meaning as defined above; $R_2$ is O or S; and $R_3$, $X_1$, $X_2$, $X_3$, and W have the same meaning as the symbols for the above Formula (I)), obtained in the above-described Process 7, thereby to produce Compound (XXIII) (wherein $PG_2$ has the same meaning as defined above; $R_2$ is O or S; and $R_3$, $X_1$, $X_2$, $X_3$, and W have the same meaning as the symbols for the above Formula (I)).

As to the removal of the protective group $PG_4$ used in this process, the method of removal may vary depending on the type of the protective group and stability of the compound, but methods described in the literature [See T. W. Greene, *Protective Groups in Organic Synthesis*, John Wiley & Sons (1981)] or methods equivalent thereto can be carried out. For example, the Compound (XII) in which $PG_4$ is tert-butyl can be deprotected in a mixed solvent of trifluoroacetic acid and chloroform. The reaction temperature can be appropriately selected by a person having ordinary skill in the art in accordance with the starting compound or reaction solvent used, but it is typically from room temperature to the boiling point of the solvent. Also, the reaction is typically completed between 1 hour to 24 hours, but the reaction time can be appropriately extended or reduced.

The resulting Compound (XXIII) is subjected to isolation and purification by known separation and purification means such as, for example, concentration, concentration under reduced pressure, crystallization, solvent extraction, reprecipitation or chromatography, or may be subjected to the next process without isolation and purification.

(Process 23) The present process is a method of subjecting Compound (XXIII) (wherein $PG_2$ has the same meaning as defined above; $R_2$ is O or S; and $R_3$, $X_1$, $X_2$, $X_3$ and W have the same meaning as the symbols for the above Formula (I)), obtained by the above-described Process 22, and Compound (XXIV) (wherein $PG_5$ may be absent, or if present, it is a protective group such as tert-butoxycarbonyl, ethoxycarbonyl or benzyloxycarbonyl) to a condensation reaction, thereby to produce Compound (XXV) (wherein $PG_2$ and $PG_5$ have the same meaning as defined above; $R_2$ is O or S; and $R_3$, $X_1$, $X_2$, $X_3$, and W have the same meaning as the symbols for the above Formula (I)).

The Compound (XXIV) used in this process may be exemplified by tert-butylcarbazate, ethoxycarbonylhydrazine, benzyloxycarbonylhydrazine, or hydrazine. The Compound (XXIV) is commercially available, or can be produced by a known method.

The condensation reaction used in this process employs the carboxylic acid of the Compound (XXIII) or a reactive derivative thereof, and the Compound (XXIV). The Compound (XXIII) as a reactive derivative can be exemplified by a mixed acid anhydride, activated ester, activated amide, and the like; they can be obtained by a method described, for example, in the international publication of WO98/05641. Specifically, the condensation can be conducted, for example, using the Compound (XXIII) and the Compound (XXIV) in a solvent such as tetrahydrofuran, dimethylsulfoxide, N,N-dimethylformamide, 1,4-dioxane, dichloromethane, chloroform, and the like, together with a condensation agent such as 1-(3-dimethylaminopropyl)-3-ethylcarbodiimide, and 1-hydroxybenzotriazole. In this case, Compound (XXIV) is used in an amount of from 1 to 3 mol, preferably 1 mol; the condensation agent is used in an amount of from 1 to 10 mol, preferable from 1 to 3 mol, relative to 1 mol of compound (XXIII). The reaction temperature is appropriately selected by a person skilled in the art in accordance with the starting compound or reaction solvent used, but it is typically from room temperature to the boiling point of the solvent used in the reaction. Also, the reaction is typically completed between 1 hour to 24 hours, but the reaction time can be appropriately extended or reduced.

The resulting Compound (XXV) is subjected to isolation and purification by known separation and purification means such as, for example, concentration, concentration under reduced pressure, crystallization, solvent extraction, reprecipitation or chromatography, or may be subjected to the next process without isolation and purification.

(Process 24) The present process is a method of deprotecting the protective group $PG_5$ of Compound (XXV) (wherein $PG_2$ and $PG_5$ have the same meaning as defined above; $R_2$ is O or S; and $R_3$, $X_1$, $X_2$, $X_3$, and W have the same meaning as the symbols for the above Formula (I)), obtained in the above-described Process 23, thereby to produce Compound (XXVI) (wherein $PG_2$ has the same meaning as defined above; $R_2$ is O or S; and $R_3$, $X_1$, $X_2$, $X_3$, and W have the same meaning as the symbols for the above Formula (I)).

As to the removal of the protective group $PG_5$ used in this process, the method of removal may vary depending on the type of the protective group and stability of the compound, but methods described in the literature [See T. W. Greene, *Protective Groups in Organic Synthesis*, John Wiley & Sons (1981)] or methods equivalent thereto can be carried out. For example, the Compound (XXV) in which $PG_5$ is tert-butoxycarbonyl can be deprotected in a mixed solvent of trifluoroacetic acid and chloroform. The reaction temperature can be appropriately selected by a person having ordinary skill in the art in accordance with the starting compound or reaction solvent used, but it is typically from room temperature to the boiling point of the solvent. Also, the reaction is typically completed between 1 hour to 24 hours, but the reaction time can be appropriately extended or reduced.

The resulting Compound (XXVI) is subjected to isolation and purification by known separation and purification means such as, for example, concentration, concentration under reduced pressure, crystallization, solvent extraction, reprecipitation or chromatography, or may be subjected to the next process without isolation and purification.

(Process 25) The present process is a method of converting a carbohydrazide group of the Compound (XXVI) (wherein $PG_2$ has the same meaning as defined above; $R_2$ is O or S; and $R_3$, $X_1$, $X_2$, $X_3$, and W have the same meaning as the symbols for the above Formula (I)), obtained in the above-described Process 24, into a heterocyclic group thereof, thereby to produce Compound (XXVII) (wherein $PG_2$ has the same meaning as defined above; $R_2$ is O or S; and $R_3$, $X_1$, $X_2$, $X_3$, and W have the same meaning as the symbols for the above Formula (I)).

The reaction used in this process employs a method well known to a person skilled in the art. The reaction can be carried out in accordance with the method described in literature, for example, Journal of Medicinal Chemistry (1993) Vol. 36, Page 1090. The reaction used in this process, specifically, for example, the Compound (XXVII) can be synthesized by reacting the Compound (XXVI) with 1,1'-carbonyldiimidazole, if necessary using a base such as triethylamine or N,N-diisopropylethylamine, in the presence of a solvent such as, for example, tetrahydrofuran, 1,4-dioxane or N-methyl-2-pyrrolidinone. In this case, 1,1'-carbonyldiimidazole is used in an amount of from 1 to 10 mol, preferably 1 to 3 mol; if necessary, a base is used in an amount of from 1 to 10 mol, preferable from 1 to 3 mol, relative to 1 mol of compound (XXVI). The reaction temperature is appropriately selected by a person skilled in the art in accordance with the starting compound or reaction solvent used, but it is typically from room temperature to the boiling point of the solvent used in the reaction. Also, the reaction is typically completed between 1 hour to 24 hours, but the reaction time can be appropriately extended or reduced.

The resulting Compound (XXVII) is subjected to isolation and purification by known separation and purification means such as, for example, concentration, concentration under reduced pressure, crystallization, solvent extraction, reprecipitation or chromatography, or may be subjected to the next process without isolation and purification.

If there is no need for deprotection regarding the Compound (XXVII), then the Compound (XXVII) per se becomes the compound according to the present invention without conducting Process 26 and the processes thereafter.

(Process 26) The present process is a method of deprotecting the protective group $PG_2$ of Compound (XXVII) (wherein $PG_2$ has the same meaning as defined above; $R_2$ is O or S; and $R_3$, $X_1$, $X_2$, $X_3$, and W have the same meaning as the symbols for the above Formula (I)), obtained in the above-described Process 25, thereby to produce Compound (I-2) (wherein $R_2$ is O or S; and $R_3$, $X_1$, $X_2$, $X_3$, and W have the same meaning as the symbols for the above Formula (I)), As to the removal of the protective group $PG_2$ used in this process, the method of removal may vary depending on the type of the protective group and stability of the compound, but methods described in the literature [See T. W. Greene, *Protective Groups in Organic Synthesis*, John Wiley & Sons (1981)] or methods equivalent thereto can be carried out. For example, the Compound (XXVII) in which $PG_2$ is tert-butyl can be deprotected in a solvent of formic acid. The reaction temperature can be appropriately selected by a person having ordinary skill in the art in accordance with the starting compound or reaction solvent used, but it is typically from room temperature to the boiling point of the solvent. Also, the reaction is typically completed between 1 hour to 24 hours, but the reaction time can be appropriately extended or reduced.

The resulting Compound (I-2) is subjected to isolation and purification by known separation and purification means such as, for example, concentration, concentration under reduced pressure, crystallization, solvent extraction, reprecipitation or chromatography.

Among the compounds represented by the General Formula (I) (wherein $R_1$, $R_1'$, $R_2$, $R_3$, $X_1$, $X_2$, $X_3$, and W have the same meaning as defined in the above) according to the invention, the compound of Formula (I-3) (wherein $R_1$ is 1,3,4-oxadiazol-2(3H)-one; $R_1'$ is a hydrogen atom; $R_2$ is $SO_2$; $R_3$, $X_1$, $X_2$, $X_3$, and W have the same meaning as the symbols for the above Formula (I)) can be prepared by, for example, the following method.

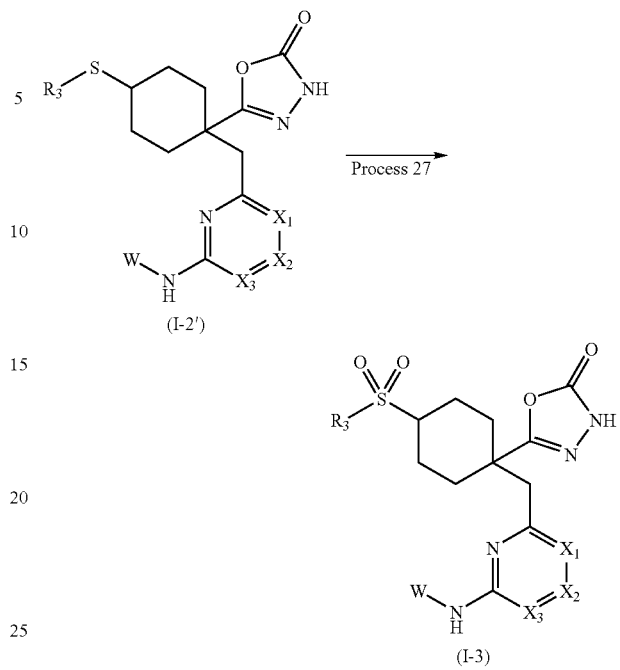

(Process 27) Among the Compound (I-2) (wherein $R_2$ is O or S; and $R_3$, $X_1$, $X_2$, $X_3$, and W have the same meaning as the symbols for the above Formula (I)), the present process is a method of oxidizing the sulfur atom of Compound (I-2') (wherein $R_2$ is S; and $R_3$, $X_1$, $X_2$, $X_3$, and W have the same meaning as the symbols for the above Formula (I)), obtained in the above Process 26, thereby to produce Compound (I-3) (wherein $R_2$ is $SO_2$; and $R_3$, $X_1$, $X_2$, $X_3$, and W have the same meaning as the symbols for the above Formula (I)).

The oxidation reaction used in this process employs a method well-known to a person skilled in the art. The reaction can be carried out in accordance with the method described in literature, for example, Tetrahedron Letters (1981) Vol. 22, Page 1287. In the oxidation reaction used in this process, specifically, for example, the Compound (I-3) can be synthesized by reacting Compound (I-2') with OXONE® (Trade name; purchased from Aldrich, Co. Ltd.), in a mixed solvent of acetonitrile and water. In this case, OXONE® is used in an amount of from 1 to 10 mol, preferably 2 to 5 mol, relative to 1 mol of compound (I-2'). The reaction temperature is appropriately selected by a person skilled in the art in accordance with the starting compound or reaction solvent used, but it is typically from room temperature to the boiling point of the solvent used in the reaction. Also, the reaction is typically completed between 1 hour to 24 hours, but the reaction time can be appropriately extended or reduced.

The resulting Compound (I-3) is subjected to isolation and purification by known separation and purification means such as, for example, concentration, concentration under reduced pressure, crystallization, solvent extraction, reprecipitation or chromatography.

Among the compounds represented by the General Formula (I) (wherein $R_1$, $R_1'$, $R_2$, $R_3$, $X_1$, $X_2$, $X_3$, and W have the same meaning as defined in the above) according to the invention, the compound of Formula (I-4) (wherein $R_1$ is $CONR_{a2}'R_{a2}'$; $R_1'$ is a hydrogen atom; $R_2$ is O or S; $R_3$, $R_{a2}$, $R_{a2}'$ $X_1$, $X_2$, $X_3$, and W have the same meaning as the symbols for the above Formula (I)) can be prepared by, for example, the following method.

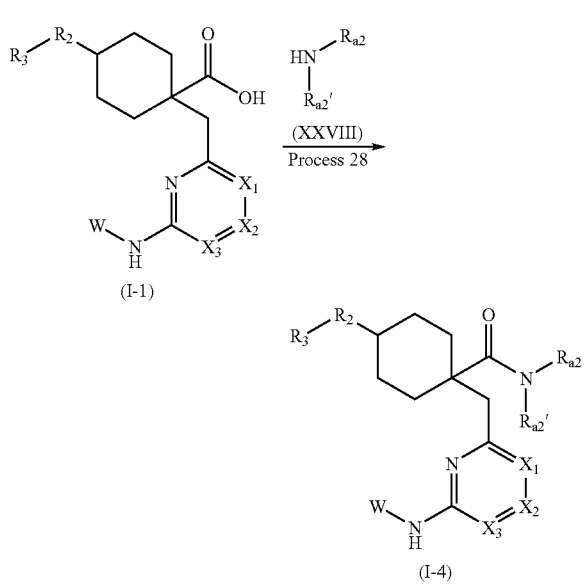

Also in the case where $R_1$ is $CONR_{a4}OR_{a4}'$ (wherein $R_{a4}$ and $R_{a4}'$ have the same meaning as the symbols for the above Formula (I)), the relevant reaction can be carried out by the same method as used in Process 28 above, or a method equivalent thereto, or a combination of the same with a commonly used method.

Among the compounds represented by the General Formula (I) (wherein $R_1$, $R_1'$, $R_2$, $R_3$, $X_1$, $X_2$, $X_3$, and W have the same meaning as defined in the above) according to the invention, the compound of Formula (I-5) (wherein $R_1$ is $NR_{a3}COR_{a3}'$; $R_2$ is O or S; $R_1'$ is a hydrogen atom; $R_3$, $R_{a3}$, $R_{a3}'$, $X_1$, $X_2$, $X_3$, and W have the same meaning as the symbols for the above Formula (I)) can be prepared by, for example, the following method.

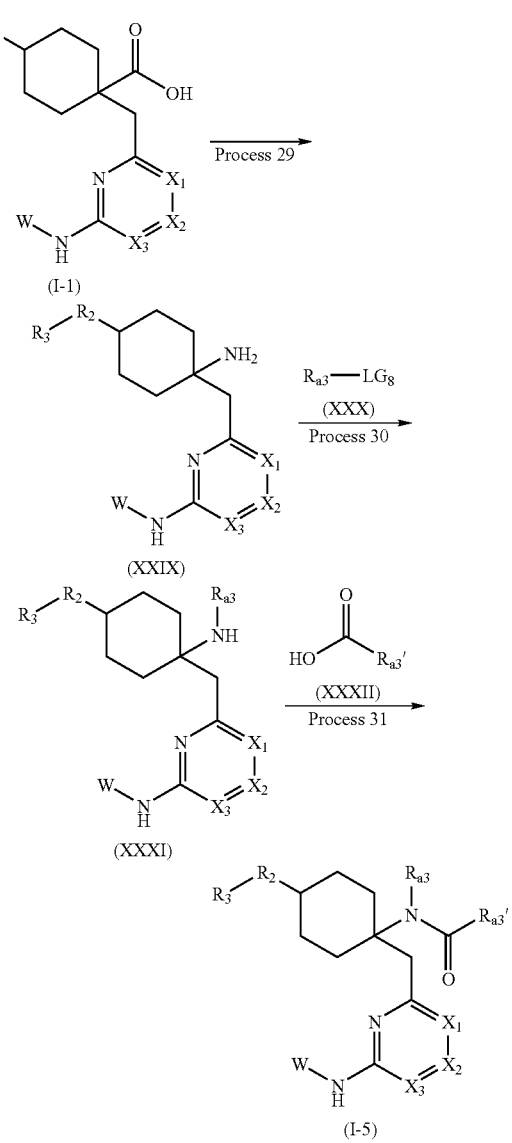

(Process 28) The present process is a method of subjecting the Compound (I-1) (wherein $R_2$ is O or S; $R_3$, $X_1$, $X_2$, $X_3$, and W have the same meaning as the symbols for the above Formula (I)), obtained in the above Process 10, and Compound (XXVIII) (wherein $R_{a2}$ and $R_{a2}'$ have the same meaning as the symbols for the above Formula (I)), to a condensation reaction, thereby to produce Compound (I-4) (wherein $R_2$ is O or S; $R_3$, $R_{a2}$, $R_{a2}'$, $X_1$, $X_2$, $X_3$, and W have the same meaning as the symbols for the above Formula (I)).

The Compound (XXVIII) used in this reaction can be exemplified by ammonium chloride, methylamine, dimethylamine, and the like. The Compound (XXVIII) is commercially available, or can be prepared by a known method.

The condensation reaction used in this process can be conducted using a carboxylic acid of the Compound (I-1) or a reactive derivative thereof, and the Compound (XXVIII). The "reactive derivative" of the Compound (I-1) can be exemplified by a mixed acid anhydride, activated ester, activated amide, and the like; and they can be obtained in accordance with the method described in the international publication of WO98/05641. Specifically, for example, the condensation reaction can be conducted using the Compound (I-1) and the Compound (XXVIII) in a solvent such as, for example, tetrahydrofuran, dimethylsufoxide, N,N-dimethylformamide, 1,4-dioxane, dichloromethane, or chloroform, together with a condensation agent such as 1-(3-dimethylaminopropyl)-3-ethylcarbodiimide, and 1-hydroxybenzotriazole. In this case, the Compound (XXVIII) is used in an amount of from 1 to 10 mol, preferably 1 to 3 mol; and the condensation agent is used in an amount of 1 to 10 mol, preferably 1 to 3 mol, relative to 1 mol of Compound (I-1). The reaction temperature is appropriately selected by a person skilled in the art in accordance with the starting compound or reaction solvent used, but it is typically from room temperature to the boiling point of the solvent used in the reaction. Also, the reaction is typically completed between 1 hour to 24 hours, but the reaction time can be appropriately extended or reduced.

The resulting Compound (I-4) is subjected to isolation and purification by known separation and purification means such as, for example, concentration, concentration under reduced pressure, crystallization, solvent extraction, reprecipitation or chromatography.

(Process 29) The present process is a method of converting the carboxylic acid of the Compound (I-1) (wherein $R_2$ is O or S; $R_3$, $X_1$, $X_2$, $X_3$, and W have the same meaning as the symbols for the above Formula (I)) obtained in the Process 10, into a amino group thereof thereby to Compound (XXIX) (wherein $R_2$ is O or S; $R_3$, $X_1$, $X_2$, $X_3$, and W have the same meaning as the symbols for the above Formula (I)).

The reaction used in this process is a method well-known to a person skilled in the art, for example, the Curtius rearrangement reaction (Tetrahedron (1974) Vol. 30, Page 2151). In the rearrangement reaction used in this process, specifically, for example, the Compound (XXIX) can be synthesized by reacting the Compound (I-1) with diphenyl phosphoric azide in a solvent such as, for example, 1,4-dioxane, or toluene, in the presence of a base such as, for example, triethylamine to produce an acyl azide, followed by heating, thereby to afford the Compound (XXIX). In this case, the base is used in an amount of from 1 to 10 mol, preferably 1 to 3 mol; and diphenyl phosphoric azide is used in an amount of 1 to 10 mol, preferably 1 to 3 mol, relative to 1 mol of compound (I-1). The reaction temperature is appropriately selected by a person skilled in the art in accordance with the starting compound or reaction solvent used, but it is typically from room temperature to the boiling point of the solvent used in the reaction. Also, the reaction is typically completed between 1 hour to 24 hours, but the reaction time can be appropriately extended or reduced.

The resulting Compound (XXIX) is subjected to isolation and purification by known separation and purification means such as, for example, concentration, concentration under reduced pressure, crystallization, solvent extraction, reprecipitation or chromatography, or may be subjected to the next process without isolation and purification.

(Process 30) The present process is a method of reacting the Compound (XXIX) (wherein $R_2$ is O or S; $R_3$, $X_1$, $X_2$, $X_3$, and W have the same meaning as the symbols for the above Formula (I)) obtained in the Process 29, with Compound (XXX) (wherein $LG_8$ is a leaving group such as halogen atom, and $R_{3a}$ has the same meaning as the symbols for the above Formula (I)), thereby to Compound (XXXI) (wherein $R_2$ is O or S; $R_3$, $R_{a3}$, $X_1$, $X_2$, $X_3$, and W have the same meaning as the symbols for the above Formula (I)).

The Compound (XXX) used in this process is, for example, methyl iodide, ethyl iodide, and the like. The Compound (XXX) is commercially available.

The reaction used in this process is a method well-known to a person skilled in the art. In the reaction used in this process, specifically, for example, the Compound (XXXI) can be synthesized by reacting the Compound (XXX) with a base such as, for example, potassium carbonate, cesium carbonate, triethylamine, diisopropylethylamine, or sodium hydroxide, in a solvent such as, for example, tetrahydrofuran, 1,4-dioxane, or N,N-dimethylformamide. In this case, the Compound (XXX) is used in an amount of from 0.5 to 10 mol, preferably 0.5 to 3 mol; and the base is used in an amount of 1 to 10 mol, preferably 1 to 3 mol, relative to 1 mol of compound (XXIX). The reaction temperature is appropriately selected by a person skilled in the art in accordance with the starting compound or reaction solvent used, but it is typically from room temperature to the boiling point of the solvent used in the reaction. Also, the reaction is typically completed between 1 hour to 24 hours, but the reaction time can be appropriately extended or reduced.

The resulting Compound (XXXI) is subjected to isolation and purification by known separation and purification means such as, for example, concentration, concentration under reduced pressure, crystallization, solvent extraction, reprecipitation or chromatography, or may be subjected to the next process without isolation and purification.

(Process 31) The present process is a method of subjecting the Compound (XXXI) (wherein $R_2$ is O or S; $R_3$, $R_{a3}$, $X_1$, $X_2$, $X_3$, and W have the same meaning as the symbols for the above Formula (I)) obtained in the Process 30, and Compound (XXXII) (wherein $R_{3a}'$ has the same meaning as the symbols for the above Formula (I)), to a condensation reaction, thereby to produce Compound (I-5) (wherein $R_2$ is O or S; $R_3$, $R_{a3}$, $R_{a3}'$, $X_1$, $X_2$, $X_3$, and W have the same meaning as the symbols for the above Formula (I)).

The Compound (XXXII) used in this process can be exemplified by acetic anhydride, propionic acid, butyric acid. The Compound (XXXII) is commercially available, or can be produced by a known method.

The condensation reaction used in this process can be conducted using the Compound (XXXI), and the carboxylic acid of the Compound (XXXII) or a reactive derivative thereof. The reactive derivative of the Compound (XXXII) can be exemplified by a mixed acid anhydride, activated ester, activated amide, and the like. They can be obtained, for example, by the method described in the international publication of W098/05641. Specifically, for example, the condensation can be conducted using the Compound (XXXI) and the Compound (XXXII) in a solvent such as, for example, tetrahydrofuran, dimethylsulfoxide, N,N-dimethylformamide, 1,4-dioxane, dichloromethane, or chloroform, together with a condensation agent such as 1-(3-dimethylaminopropyl)-3-ethylcarbodiimide, and 1-hydroxybenzotriazol. In this case, the Compound (XXXII) is used in an amount of from 1 to 10 mol, preferably 1 to 3 mol; and the condensation agent is used in an amount of 1 to 10 mol, preferably 1 to 3 mol, relative to 1 mol of compound (XXXI). The reaction temperature is appropriately selected by a person skilled in the art in accordance with the starting compound or reaction solvent used, but it is typically from room temperature to the boiling point of the solvent used in the reaction. Also, the reaction is typically completed between 1 hour to 24 hours, but the reaction time can be appropriately extended or reduced.

The resulting Compound (I-5) is subjected to isolation and purification by known separation and purification means such as, for example, concentration, concentration under reduced pressure, crystallization, solvent extraction, reprecipitation or chromatography.

Also in the case where $R_1$ is $NR_{a5}CONR_{a5}'$, $NR_{a6}COOR_{a6}'$, or $NR_{a8}SO_2R_{a8}'$ (wherein $R_{a5}$, $R_{a5}'$, $R_{a6}$, $R_{a6}'$, $R_{a8}$, and $R_{a8}'$ have the same meaning as the symbols for the above Formula (I)), the relevant reaction can be carried out by the same method as used in the Process 30 above, or a method equivalent thereto, or a combination of the same with a commonly used method.

Next, the Aurora A and Aurora B inhibitory actions of the compound of General Formula (I) according to the invention will be explained below.

Aurora A Inhibitory Activity (1) Purification of Aurora A cDNA of N-terminal His-tagged human Aurora A was integrated into an expression vector, which was then highly expressed in *Escherichia coli* BL21-CodonPlus(DE3)-RIL cells. The *Escherichia coli* was harvested and lysed, and then the His-tagged human Aurora A protein was applied onto a nickel chelate column and eluted from the column with imidazole. The active fractions were desalted with a desalting column to give a purified enzyme.

(2) Measurement of Activity of Aurora A

For measurement of the activity of Aurora A, the substrate used was a synthetic peptide (5-FAM (5-carboxyfluorescein)-y-aminobutyric acid-Ala-Leu-Arg-Arg-Ala-Ser-Leu-Gly-NH$_2$)(SEQ.ID.NO.: 1), which was purchased from Toray Research Center, Inc.

For the phosphorylation reaction, the method by Upstate, Inc. [Kinase Profiler™ Assay Protocols] was referred to, and phosphorylation of the substrate was detected using IMAP® technology (Molecular Devices, Co. Ltd.) (Gaudet E W. et. al, J. Biomol. Screen, 8, 164-175(2003)). Concretely, the phosphorylation reaction and the detection were carried out as follows:

The phosphorylation reaction was conducted using 384 well plate, and the reaction volume was 10 µl/well. The reaction buffer is comprised of 50 mM Tris-chloride buffer (pH 7.4), 15 mM magnesium acetate, and 0.2 mM ethylenediamine-N,N,N',N'-tetraacetic acid (EDTA). Thereto, the purified Aurora A protein, 100 nM of the peptide substrate, and 20 µM of adenosine 5'-triphosphate (ATP) were added, and then the reaction was carried out at 30° C. for 120 minutes.

Thereafter, in order to terminate and detect the reaction, 30 µl of the IMAP (registered trademark) binding reagent (IMAP Progressive Binding Reagent, R7284) that had been diluted (1:400) in the 1× IMAP binding buffer A (IMAP Progressive Binding Buffer A, 5× stock, R7282) was added to each well. The solution stood still for 60 minutes in the dark, and then fluorescence polarization was measured using a high-end microplate reader (excitation wavelength: 485 nm; emission wavelength: 520 nm).

The compound to be tested was added to the reaction system such that a dilution series of the compound in dimethylsulfoxide (DMSO) was prepared, and then 0.5 µL of this solution was added for the testing to each well. Each control well was provided by adding 0.5 µL of DMSO to the well in place of the DMSO solution containing the compound to be tested.

Aurora B Inhibitory Activity (1) Measurement of Activity of Aurora B (Method A)

An assay development kit for IMAP (registered trademark) (Aurora B), purchased from Cama Biosciences, Inc., was used for phosphorylation reaction, and the phosphorylation of a substrate was detected using the IMAP technology. The assay development kit used is comprised of an assay buffer, GST-tagged human Aurora B(AurB)/His-tagged human INCENP complex proteins (amino acid sequence: 803-916, AAU04398.1), and an ATP/substrate solution. Using the same, the phosphorylation reaction was conducted in accordance with a partially revised protocol attached to the kit, and then the phosphorylation of the substrate was detected using the IMAP technology.

For the phosphorylation reaction, 384 well plate was used, and the reaction volume was 10 µl/well. The composition of the reaction buffer (assay buffer) is comprised of 20 mM of HEPES buffer (pH 7.4), 0.01% Tween-20, and 2 mM of dithiothreitol (DTT). Thereto, AurB/INCENP complex protein, 100 nM of the substrate, and 40 µM of ATP, and 1 mM of magnesium salt were added, and then the reaction was conducted at 25° C. for 45 minutes. Thereafter, in order to terminate and detect the reaction, 30 µl of the IMAP (registered trademark) binding reagent (IMAP Progressive Binding Reagent, R7284) that had been diluted (1:400) in the 1× IMAP binding buffer A (IMAP Progressive Binding Buffer A, 5× stock, R7282) was added to each well. The solution stood still for 60 minutes in the dark, and then fluorescence polarization was measured using a high-end microplate reader (excitation wavelength: 485 nm; emission wavelength: 520 nm).

The compound to be tested was added to the reaction system such that a dilution series of the compound in DMSO was prepared, and then 0.5 µL of this solution was added for the testing to each well. Each control well was provided by adding 0.5 µL of DMSO to the well in place of the DMSO solution containing the compound to be tested.

(2) Measurement of Activity of Aurora B (Method B)

(a) Purification of Aurora B cDNA of human Aurora B having histidine tag fused at the amino terminal was integrated into an expression vector, which was then highly expressed in *Escherichia coli* BL21-CodonPlus(DE3)-RIL cells. The *Escherichia coli* cells were recovered and solubilized, and then the histidine-tagged Aurora A protein was adsorbed onto a nickel chelate column and eluted from the column with imidazole. The active fraction was desalted with a desalting column to give a pure enzyme.

(b) Measurement of Activity of Aurora B

For measurement of the activity of Aurora B, the substrate used was Kemptide (Leu-Arg-Arg-Ala-Ser-Leu-Gly) (SEQ.ID.NO.: 2), a synthetic peptide purchased from Sigma-Aldrich, Inc. [Certificate of analysis (Upstate, Inc.)].

Reaction was conducted by a partial modification of the method of activity measurement for Aurora A. The amount of the reaction liquid was 21.1 µL, and the composition of the reaction buffer (R2 buffer) was 50 mM Tris-hydrochloride buffer (pH 7.4)/15 mM magnesium acetate/0.2 mM ethylenediamine-N,N,N',N'-tetraacetic acid (EDTA). To this, purified Aurora B, 100 µM of a substrate peptide, 100 µM of unlabeled adenosine triphosphate (ATP) and 1 µCi of [γ-$^{33}$P] labeled ATP (2,500 Ci/mmole or more) were added, and the mixture was reacted at 30° C. for 20 minutes. Then, 10 µL of 350 mM phosphate buffer was added to the reaction system to stop the reaction. The substrate peptide was adsorbed on a P81 paper filter 96-well plate and then washed with 130 mM phosphate buffer for several times. The radiation activity of the peptide was measured with a liquid scintillation counter. The [γ-$^{33}$P] labeled ATP was purchased from Amersham Biosciences Co., Ltd.

The compound to be tested was added to the reaction system such that a dilution series of the compound in dimethylsulfoxide was first prepared, and 1.1 µL of this solution was added. A control was provided by adding 1.1 µL of DMSO to the reaction system.

Using the above method (in the measurement of activity of Aurora B, Method A was used), the results for measurement of the activities of Aurora A and Aurora B were obtained as shown in Table 1. The compound according to the invention exhibited excellent Aurora A selective inhibitory activity. Similar results are obtained when Method B is used in the measurement of activity of Aurora B.

TABLE 1

| Example | Inhibitory activity for Aurora A ($IC_{50}$, nM) | Inhibitory activity for Aurora B ($IC_{50}$, nM) |
|---|---|---|
| Example 1 | 0.07 | 25 |
| Example 3 | 0.12 | 59 |
| Example 4 | 0.11 | 32 |
| Example 5 | 0.12 | 130 |
| Example 6 | 0.07 | 37 |
| Example 7 | 0.17 | 130 |
| Example 8 | 0.54 | 150 |
| Example 9 | 0.16 | 190 |
| Example 10 | 0.15 | 200 |
| Example 11 | 1.8 | 750 |
| Example 12 | 2.5 | >1000 |
| Example 13 | 1.3 | >1000 |
| Example 15 | 2.0 | 870 |
| Example 16 | 1.6 | >1000 |
| Example 17 | 0.45 | 350 |
| Example 18 | 0.49 | 200 |
| Example 19 | 0.82 | 320 |
| Example 20 | 1.0 | 660 |
| Example 21 | 2.8 | >1000 |
| Example 22 | 4.1 | >1000 |
| Example 23 | 0.39 | 490 |
| Example 24 | 0.12 | 130 |
| Example 25 | 0.87 | 690 |
| Example 26 | 1.4 | 800 |
| Example 27 | 2.4 | 220 |
| Example 28 | 3.5 | 710 |
| Example 29 | 0.19 | 670 |
| Example 30 | 0.08 | 39 |

TABLE 1-continued

| Example | Inhibitory activity for Aurora A (IC$_{50}$, nM) | Inhibitory activity for Aurora B (IC$_{50}$, nM) |
|---|---|---|
| Example 31 | 0.19 | 53 |
| Example 32 | 0.15 | 70 |
| Example 33 | 0.13 | 210 |
| Example 34 | 0.47 | 690 |
| Example 35 | 0.31 | 120 |
| Example 36 | 0.43 | 370 |
| Example 40 | 0.09 | 95 |
| Example 41 | 0.18 | 110 |
| Example 42 | 0.23 | 142 |

Next, the cell growth suppressive action of the compound of the General Formula (I) according to the invention will be explained below.

Method For Judging The Pharmaceutical Effect Using Cells a) Reagent

Fetal calf serum (FCS) was purchased from Moregate Biotech, and DMEM medium was purchased from Invitrogen Corp. WST-8 was purchased from Kishida Chemical Co., Ltd.

b) Cells

Human cervical cancer cells (HeLa S3) were obtained from the American Type Culture Collection (ATCC).

c) Method of Judging the Effect

Cells were suspended in a DMEM medium containing 10% FCS, and the cell suspension was dispensed to a 96-well plastic plate at a rate of 750 cells/100 microliters per well. The plate was incubated overnight in 5% $CO_2$-95% air at 37° C. A drug was subjected to graded dilution in dimethylsulfoxide and further diluted with a DMEM medium containing 10% FCS. Then, the dilution was dispensed to the plate on which cells had been disseminated, at a rate of 100 microliters per well. The plate was incubated for further three days in 5% $CO_2$-95%/(air at 37° C. Cell growth after incubation was measured by the WST-8 method (H. Tominaga, et al., *Anal. Commun.*, 36, 47-50 (1999)). Here, the WST-8 method refers to a method in which 20 microliters of a WST-8 reagent solution is added to each well, incubation is conducted at 37° C. for 60 minutes, the plate is stirred, and the amount of formazan produced is measured by a colorimetric method to determine the inhibitory rate of the drug. The concentration for 50% growth inhibition (IC$_{50}$, μM) of the compound was determined.

As shown in Table 2, the compound according to the invention exhibited excellent cell growth inhibitory effect against human-derived cancer cells (HeLa S3).

| | Cell growth inhibitory effect (HeLaS3) (IC50, μM) |
|---|---|
| Example 1 | 1.97 |
| Example 3 | 3.95 |
| Example 4 | 0.83 |
| Example 6 | 1.93 |
| Example 8 | 1.26 |
| Example 9 | 2.21 |
| Example 11 | 2.80 |
| Example 15 | 1.76 |
| Example 18 | 0.90 |
| Example 20 | 0.90 |
| Example 23 | 0.76 |
| Example 24 | 1.15 |
| Example 26 | 3.30 |
| Example 29 | 0.67 |
| Example 30 | 0.34 |
| Example 31 | 5.89 |
| Example 32 | 0.59 |
| Example 33 | 2.22 |
| Example 34 | 0.87 |
| Example 35 | 0.22 |
| Example 36 | 1.13 |

Method for Judging the Effect by Combined use of Drugs in Cells a) Reagent

Fetal calf serum (FCS) was purchased from Moregate Biotech, DMEM medium from Invitrogen Corp., docetaxel (tradename: Taxere) from Sigma-Aldrich, Inc., and WST-8 from Kishida Chemical Co., Ltd.

b) Cells

Human cervical cancer cells (HeLa S3) were obtained from the American Type Culture Collection (ATCC).

c) Method of Judging the Effect

Cells were suspended in a DMEM medium containing 10% FCS, and the cell suspension was dispensed to two 96-well plastic plates at a rate of 750 cells/100 microliters per well. The plates were incubated overnight in 5% $CO_2$-95% air at 37° C. A drug was subjected to graded dilution in dimethylsulfoxide and further diluted with DMSO or with a DMEM medium containing 10% FCS and also containing 0.6 nM docetaxel. Then, the dilutions were each dispensed to one of the plates on which cells had been disseminated, at a rate of 100 microliters per well. The final concentration of docetaxel at this stage was 0.3 nM. Also, the concentrations in the case of sole administration of the compound according to the invention were 0.003, 0.01, 0.03, 0.1, 0.3, 1, 3 and 10 μM. The plates were incubated for further three days in 5% $CO_2$-95% air at 37° C. Cell growth after incubation was measured by the WST-8 method (H. Tominaga, et al., *Anal. Commun.*, 36, 47-50 (1999)). Here, the WST-8 method refers to a method in which 20 microliters of a WST-8 reagent solution is added to each well, incubation is conducted at 37° C. for 60 minutes, the plate is stirred, and the amount of formazan produced is measured by a colorimetric method to determine the inhibitory rate of the drug. The growth inhibitory effects of docetaxel and of the compound according to the invention were determined, with the value obtained in sole treatment of DMSO being defined as 0%.

The compound according to the invention exhibited excellent cell growth inhibitory effect as well as a synergistic action with a taxane-type anti-tumor agent such as docetaxel against human-derived cancer cells (HeLa S3), as shown in Table 3.

TABLE 3

| Example | Cell growth inhibitory effect by sole administration of docetaxel (0.3 nM) (%) | Conc. of the compound of Example (μM) | Cell growth inhibitory effect by sole administration of the compound of Example (%) | Cell growth inhibitory effect by combined administration of docetaxel and the compound of Example (%) |
|---|---|---|---|---|
| Example 1 | 25.6 | 0.3 | 4.4 | 84.7 |
| Example 3 | 53.4 | 0.3 | 5.4 | 74.1 |
|  |  | 1.0 | 26.9 | 90.4 |
| Example 4 | 52.1 | 0.3 | 22.9 | 88.6 |
|  |  | 1.0 | 52.9 | 93.8 |
| Example 6 | 52.1 | 0.3 | 7.2 | 70.0 |
|  |  | 1.0 | 25.6 | 87.0 |
| Example 8 | 53.4 | 0.3 | 12.2 | 84.6 |
|  |  | 1.0 | 49.0 | 95.0 |
| Example 9 | 53.4 | 1.0 | 37.1 | 91.8 |
|  |  | 3.0 | 59.0 | 95.0 |
| Example 11 | 53.4 | 0.3 | 15.1 | 72.1 |
|  |  | 1.0 | 25.4 | 84.5 |
| Example 15 | 53.4 | 0.3 | 17.0 | 76.4 |
|  |  | 1.0 | 42.4 | 90.8 |
| Example 18 | 52.1 | 0.1 | 7.4 | 61.5 |
|  |  | 0.3 | 21.3 | 77.4 |
| Example 20 | 52.1 | 0.3 | 25.9 | 85.0 |
|  |  | 1.0 | 49.8 | 94.4 |
| Example 23 | 49.6 | 0.1 | 3.7 | 71.5 |
|  |  | 0.3 | 36.0 | 87.4 |
| Example 24 | 49.6 | 0.1 | 0.5 | 72.8 |
|  |  | 0.3 | 25.4 | 87.8 |
| Example 26 | 49.6 | 0.3 | 11.8 | 67.3 |
|  |  | 1.0 | 18.2 | 88.5 |
| Example 29 | 49.6 | 0.1 | 11.3 | 79.0 |
|  |  | 0.3 | 39.9 | 92.9 |
| Example 30 | 52.1 | 0.1 | 28.3 | 81.2 |
|  |  | 0.3 | 53.4 | 92.0 |
| Example 31 | 48.9 | 1.0 | 1.0 | 75.1 |
|  |  | 3.0 | 38.5 | 89.0 |
| Example 32 | 48.9 | 0.1 | 6.3 | 88.6 |
|  |  | 0.3 | 40.8 | 94.0 |
| Example 33 | 48.9 | 0.3 | 0.3 | 75.5 |
|  |  | 1.0 | 23.4 | 91.3 |
| Example 34 | 48.9 | 0.1 | 3.9 | 83.8 |
|  |  | 0.3 | 40.8 | 93.9 |
| Example 35 | 48.9 | 0.03 | 25.1 | 78.0 |
|  |  | 0.1 | 42.7 | 89.9 |
| Example 36 | 49.6 | 0.1 | 2.6 | 76.8 |
|  |  | 0.3 | 32.0 | 88.9 |

From the above, the compound according to the invention is believed to be useful as an antitumor agent since it exhibits not only excellent cell growth inhibitory action based on Aurora A selective inhibitory activity, but also a synergistic action in combined use with other antitumor agent. Thus, it is believed that a pharmaceutical composition or Aurora A selective inhibitor containing the novel aminopyridine derivative according to the invention or a pharmaceutically acceptable salt or ester thereof, or an antitumor agent containing the compound according to the invention or a pharmaceutically acceptable salt or ester thereof is effective in the treatment of cancer patients.

The above-mentioned pharmaceutical composition and inhibitor, and the above-mentioned antitumor agent may contain a pharmaceutically acceptable carrier or diluent. Here, the "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.); additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

A suitable tumor for which the therapeutic effect of the compound according, to the invention is expected may be exemplified by human solid cancer. Examples of human solid cancer include brain cancer, head and neck cancer, esophageal cancer, thyroid cancer, small cell carcinoma, non-small cell carcinoma, breast cancer, stomach cancer, gallbladder and bile duct cancer, liver cancer, pancreas cancer, colon cancer, rectal cancer, ovarian cancer, chorioepithelioma, uterine cancer, cervical cancer, renal pelvic and ureteral cancer, bladder cancer, prostate cancer, penile cancer, testicular cancer, embryonal cancer, Wilms' tumor, skin cancer, malignant melanoma, neuroblastoma, osteosarcoma, Ewing's tumor, soft tissue sarcoma, and the like.

Next, the above-described "pharmaceutically acceptable salt or ester" will be explained below.

When the compound according to the invention is used as an antitumor agent or the like, it may be also used in a form of pharmaceutically acceptable salt. Typical examples of the pharmaceutically acceptable salt include a salt with an alkali metal such as sodium and potassium; a salt with an inorganic acid, such as hydrochloride, sulfate, nitrate, phosphate, carbonate, hydrogen carbonate, and perchlorate; a salt with an organic acid, such as acetate, propionate, lactate, maleate, fumarate, tartrate, malate, citrate, and ascorbate; a salt with sulfonic acid, such as methanesulfonate, isethionate, benzenesulfonate, and toluenesulfonate; a salt with acidic amino acid, such as aspartate and glutamate; and the like. A pharmaceutically acceptable salt of the Compound (I) is preferably a salt with an inorganic acid, such as hydrochloride, sulfate, nitrate, phosphate, carbonate, hydrogen carbonate, and perchlorate; more preferably hydrochloride.

The process for preparation of a pharmaceutically acceptable salt of the compound according to the invention may be carried out by an appropriate combination of those methods that are conventionally used in the field of organic synthetic chemistry. A specific example thereof is a method in which a solution of the compound according to the invention in its free form is subjected to neutralization titration with an alkaline solution or an acidic solution.

Examples of the ester of the compound according to the invention include methyl ester and ethyl ester. Such esters can be prepared by esterification of a free carboxyl group according to a conventional method.

With regard to each preparation of the combined preparation according to the invention, various preparation forms can be selected, and examples thereof include oral preparations such as tablets, capsules, powders, granules or liquids, or sterilized liquid parenteral preparations such as solutions or suspensions, suppositories, ointments and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of the compound of the above Formula (I) as an active ingredient, based on the total weight of the preparation.

Liquid preparations are produced in the forms of suspension, syrup, injection and drip infusion (intravenous fluid) using appropriate additives that are conventionally used in liquid preparations, such as water, alcohol or a plant-derived oil such as soybean oil, peanut oil and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of the preparation.

Liquid preparations such as suspension or syrup for oral administration may contain, for example, 0.1 to 10% by weight of an active ingredient based on the total weight of the preparation.

Each preparation of the combined preparation according to the invention can be prepared by a person having ordinary skill in the art according to conventional methods or common techniques. For example, a preparation containing another antitumor agent that is used in combination with the compound represented by the above General Formula (I), can be prepared, if the preparation is an oral preparation, for example, by mixing an appropriate amount of the antitumor agent with an appropriate amount of lactose and filling this mixture into hard gelatin capsules which are suitable for oral administration. On the other hand, preparation can be carried out, if the preparation containing the antitumor agent is an injection, for example, by mixing an appropriate amount of the antitumor agent with an appropriate amount of 0.9% physiological saline and filling this mixture in vials for injection.

Also, in the case of a combination preparation containing the compound represented by the above General Formula (I) according to the invention and another antitumor agent, a person having ordinary skill in the art can easily prepare the preparation according to conventional methods or common techniques.

In the process according to the invention, preferred therapeutic unit may vary in accordance with, for example, the administration route of the compound represented by the General Formula (I), the type of the compound represented by the General Formula (I) used, and the dosage form of the compound represented by the General Formula (I) used; the type, administration route and dosage form of the other antitumor agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound represented by the above General Formula (I) may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other antitumor agent used in combination with the compound represented by the General Formula (I) is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 m$^2$; 50 mg in one administration for an area of 1.25 m$^2$ to less than 1.5 m$^2$; 60 mg in one administration for an area of 1.5 m$^2$ or more. This dose is appropriately increased or decreased depending on the condition of the patient.

The therapeutic unit for gemcitabine is, for example, 1 g as gemcitabine/m$^2$ in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/m$^2$ (body surface area) or less, and it may be appropriately increased or decreased within the range.

The therapeutic unit for etoposide is such that, for example, in the case of intravenous injection, 60 to 100 mg/m$^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/m$^2$ (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/m$^2$ (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/m$^2$ (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/m$^2$ is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/m$^2$ is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/m$^2$ is administered once a day by intravenous drip infusion for 3 or 4 times at an interval of one week, followed by withdrawal from medication for at least two weeks.

The therapeutic unit for topotecan is such that, for example, 1.5 mg/m$^2$ is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 m$^2$. The total dose is 3,000 to 8,000 m$^2$, which may be appropriately increased or decreased. If necessary, it may be injected or infused intramuscularly, intrathoracically or intratumorally. On the other hand, in the case of oral administration, for example, 100 to 200 m$^2$ is administered a day.

The therapeutic unit for gefitinib is such that 250 mg is orally administered once a day.

The therapeutic unit for cetuximab is such that, for example, 400 mg/m$^2$ is administered on the first day by intravenous drip infusion, and then 250 mg/m$^2$ is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/m$^2$ of 5-FU and 200 mg/m$^2$ of leucovorin are administered from the first day to the fifth day by intravenous drip infusion, and this course is repeated at an interval of 4 weeks.

The therapeutic unit for sorafenib is such that, for example, 200 mg is orally administered twice a day (400 mg per day) at least 1 hour before or 2 hours after eating.

The therapeutic unit for sunitinib is such that, for example, 50 mg is orally administered once a day for four weeks, followed by 2 weels off.

WORKING EXAMPLES

In a thin-layer chromatography of Examples and Referential Examples, Silica gel$_{60}$F$_{254}$ (Merck) was used as a plate and a UV detector was used as a detecting method. As silica gel for the column, Biotage FLASH column (SI, NH) was used. In a reversed phase preparative liquid chromatography, XBridge Prep C18 (Waters) was used as a column and a 0.1% aqueous trifluoroacetic acid solution and a 0.1% solution of trifluoroacetic acid in acetonitrile were used in a mobile phase. MS spectra were measured using Waters micromass ZQ2000 (ESI, ESCi). NMR spectra were measured using a spectrometer in the type of JEOL JNM-AL400 (400 MHz) or Varian MERCURY400 (400 MHz) and all δ values are represented in ppm. Melting points were measured under a 1° C./min raise condition using a combination of Mettler Toledo FP82HT Hot Stage and NIKON Eclipse E600 POL.

Meanings of abbreviations are as follows.

s: singlet
d: doublet
dd: double doublet
t: triplet
dt: double triplet
q: quartet
qui: quintet
m: multiplet
br: broad
J: coupling constant
Hz: Hertz
DMSO-d$_6$: dimethylsulfoxide-d$_6$
TBS: tert-butyl(dimethyl)silyl group
MOM: methoxymethyl group
TBDPS: tert-butyl(diphenyl)silyl group
TsOH: p-toluenesulfonic acid
SEM: (2-(trimethylsilyl)ethoxy)methyl group Example 1

Synthesis of trans-4-(3-chloro-2-fluorophenoxy)-1-((6-(1,3-thiazol-2-ylamino)pyridin-2-yl)methyl)cyclohexanecarboxylic acid hydrochloride

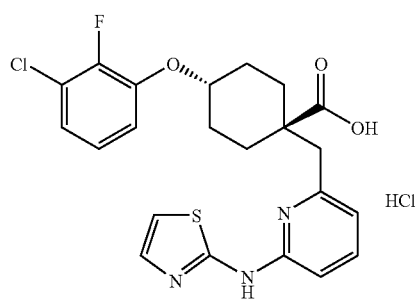

(1) Synthesis of 2-bromo-6-(((tert-butyl(dimethyl)silyl)oxy)methyl)pyridine

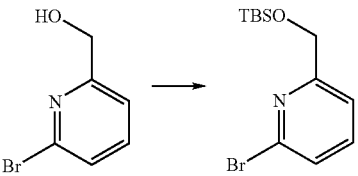

To a solution of 10 g of (6-bromo-pyridin-2-yl)methanol in 50 ml of N,N-dimethylformamide were successively added 4 g of imidazole and 8.4 g of tert-butyldimethylsilyl chloride at room temperature, followed by stirring the reaction mixture at room temperature for 2 hours. After adding water to the reaction mixture, the mixture was extracted with n-hexane. The resulting hexane solution was dried over anhydrous magnesium sulfate and filtered. The filtrate was concentrated in vacuo to give the title compound as colorless oil.

(2) Synthesis of 6-(((tert-butyl(dimethyl)silyl)oxy)methyl)-N-((2Z)-3-(methoxymethyl)-1, 3-thiazol-2(3H)-ylidene)pyridin-2-amine

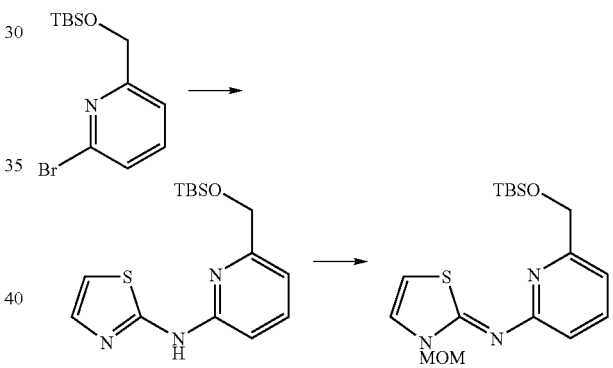

A mixture of 15.92 g of 2-bromo-6-(((tert-butyl(dimethyl)silyl)oxy)methyl)pyridine, 5.53 g of 2-aminothiazole, 3.04 g of 9,9-dimethyl-4,5-bis(diphenylphosphino)xanthene, 2.72 g of tris(dibenzylideneacetone)dipalladium(0)-chloroform complex, 18.86 g of cesium carbonate and 100 ml of toluene was stirred at 120° C. overnight, followed by cooling down to room temperature and an insoluble matter was filtered off using Celite. The resulting toluene solution was washed with water. The organic layer was dried over anhydrous magnesium sulfate and filtered. The filtrate was concentrated in vacuo to give the crude product.

The resulting crude product was suspended in 100 ml of chloroform, and then, under cooling with ice, 13.7 ml of N,N-diisopropylethylamine and 4.8 ml of chloromethylinethylether were added successively, followed by stirring the reaction mixture at room temperature overnight. The chloroform was removed in vacuo and water was added to the residue, followed by extraction with ethyl acetate. The resulting ethyl acetate solution was dried over anhydrous magnesium sulfate and filtered. The filtrate was concentrated in vacuo. The obtained residue was purified by a silica gel column chromatography (eluent: hexane to hexane/ethyl acetate=5/1) to give the title compound as a pale yellow solid.

(3) Synthesis of (6-(((2Z)-3-(methoxymethyl)-1,3-thiazol-2(3H)-ylidene)amino)pyridin-2-yl)methanol

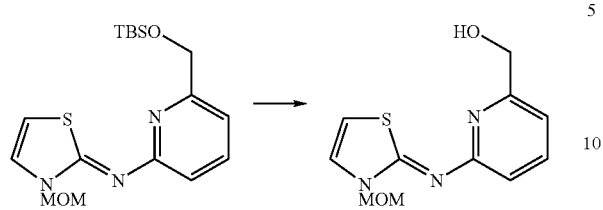

To a solution of 14.28 g of 6-(((tert-butyl(dimethyl)silyl)oxy)methyl)-N-((2Z)-3-(methoxymethyl)-1,3-thiazol-2(3H)-ylidene)pyridin-2-amine in 30 ml of chloroform and 30 ml of methanol was added 30 ml of trifluoroacetic acid under cooling with ice, followed by stirring the reaction mixture at room temperature overnight. The reaction mixture was evaporated in vacuo. The resulting residue was neutralized with saturated aqueous sodium bicarbonate solution and extracted with ethyl acetate. The resulting ethyl acetate solution was dried over anhydrous magnesium sulfate and filtered. The filtrate was concentrated in vacuo. The resulting residue was purified by a silica gel column chromatography (eluent: hexane to hexane/ethyl acetate =1/1) to give the title compound as a pale yellow solid.

(4) Synthesis of 6-(bromomethyl)-N-((2Z)-3-(methoxymethyl)-1,3-thiazol-2(3H)-ylidene)pyridin-2-amine

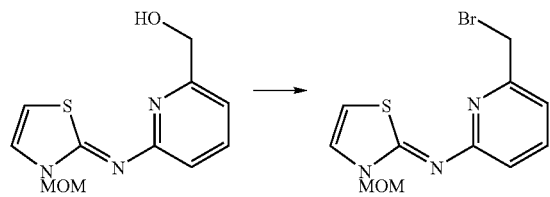

To a solution of 4.43 g of (6-(((2Z)-3-(methoxymethyl)-1,3-thiazol-2(3H)-ylidene)amino)pyridin-2-yl)methanol in 40 ml of tetrahydrofuran were successively added 3.2 ml of triethylamine and 1.5 ml of methanesulfonyl chloride under cooling with ice, followed by stirring the reaction mixture at room temperature for 1 hour. 0.74 ml of triethylamine and 0.27 ml of methanesulfonyl chloride were successively added at room temperature, followed by stirring the reaction mixture at room temperature for 1 hour. A precipitate was filtered off and washed with tetrahydrofuran, and then the filtrate was concentrated in vacuo. To a solution of the resulting residue in 30 ml of N,N-dimethylformamide was added 4.58 g of lithium bromide under cooling with ice, followed by stirring the reaction mixture at room temperature overnight. To the reaction mixture was added water and extracted with ethyl acetate. The resulting ethyl acetate solution was successively washed with water and brine, dried over anhydrous magnesium sulfate and filtered. The filtrate was concentrated in vacuo. The resulting residue was purified by a silica gel column chromatography (eluent: chloroform to chloroform/ethyl acetate=10/1) to give the title compound as a pale yellow solid.

(5) Synthesis of tert-butyl cis-4-((tert-butyl(diphenyl)silyl)oxy)-1-((6-(((2Z)-3-(methoxymethyl)-1,3-thiazol-2(3H)-ylidene)amino)pyridin-2-yl)methyl)cyclohexanecarboxylate

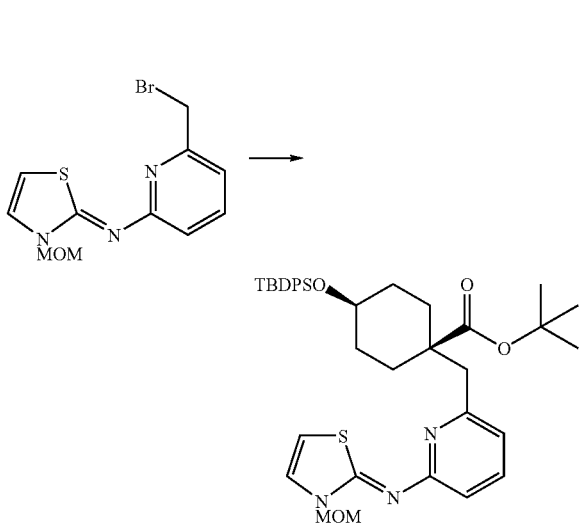

To a solution of 3.8 ml of diisopropylamine in tetrahydrofuran was added 17.3 ml of a hexane solution containing 1.58M n-butyl lithium under cooling with ice, followed by stirring the reaction mixture for 30 minutes. After cooling down to −78° C., 12 g of tert-butyl 4-((tert-butyl(diphenyl)silyl)oxy)cyclohexanecarboxylate as obtained in Reference 1 in 30 ml of tetrahydrofuran was added to the solution, and the resultant solution was stirred for 2 hours at −78° C. To the reaction mixture were added a solution of 2.87 g of 6-(bromomethyl)-N-((2Z)-3-(methoxymethyl)-1,3-thiazol-2(3H)-ylidene)pyridin-2-amine and 7.9 ml of hexamethylphosphoramide in 20 ml of tetrahydrofuran, followed by gradually warming up the reaction mixture to room temperature. The reaction mixture was stirred at room temperature overnight. To the reaction mixture was added saturated aqueous ammonium chloride solution, followed by extraction with ethyl acetate. The resulting ethyl acetate layer was washed with brine, dried over anhydrous magnesium sulfate, filtered. The filtrate was concentrated in vacuo. The resulting residue was purified by a silica gel column chromatography (eluent: hexane to hexane/ethyl acetate=10/1-4/1) to give the title compound as a pale yellow oil.

(6) Synthesis of tert-butyl cis-4-hydroxy-1-((6-(((2Z)-3-(methoxymethyl)-1,3-thiazol-2(3H)-ylidene)amino)pyridin-2-yl)methyl)cyclohexanecarboxylate

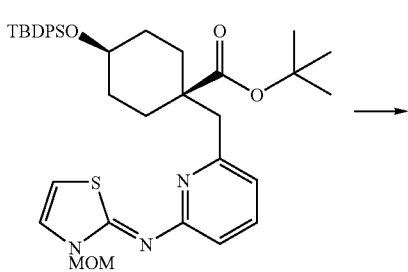

-continued

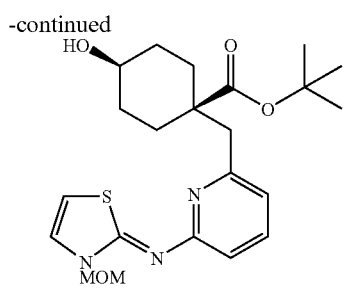

To a solution of 5.56 g of tert-butyl cis-4-((tert-butyl (diphenyl)silyl)oxy)-1-((6-(((2Z)-3-(methoxymethyl)-1,3-thiazol-2(3H)-ylidene)amino)pyridin-2-yl)methyl)cyclohexanecarboxylate in 100 ml of tetrahydrofuran was added 49.6 ml of 1 M tetrabutylammonium fluoride in tetrahydrofuran at room temperature, followed by stirring the reaction mixture at 60° C. overnight. The reaction mixture was cooled to room temperature, followed by dilution with ethyl acetate. The resulting solution was successively washed with a pH 6.8 phosphate buffer solution and brine, dried over anhydrous magnesium sulfate, filtered. The filtrate was concentrated in vacuo. The obtained residue was purified by a silica gel column chromatography (eluent: hexane to hexane/ethyl acetate=1/2) to give the title compound as a pale yellow oil.

(7) Synthesis of tert-butyl trans-4-(3-chloro-2-fluorophenoxy)-1-((6-(((2Z)-3-(methoxymethyl)-1,3-thiazol-2(3H)-ylidene)amino)pyridin-2-yl)methyl)cyclohexanecarboxylate

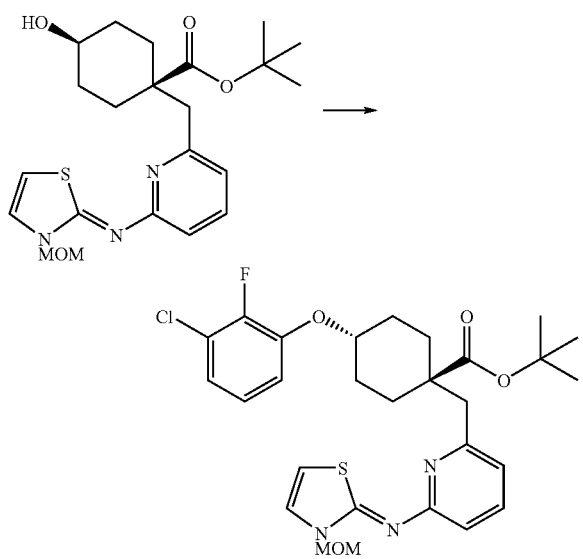

To a solution mixture of 4.34 g of tert-butyl cis-4-hydroxy-1-((6-(((2Z)-3-(methoxymethyl)-1,3-thiazol-2(3H)-ylidene)amino)pyridin-2-yl)methyl)cyclohexanecarboxylate, 2.93 g of 3-chloro-2-fluorophenol and 5.24 g of triphenylphosphine in 70 ml of tetrahydrofuran was added 3.94 ml of diisopropyl azodicarboxylate under cooling with ice, followed by stirring the reaction mixture at room temperature for 1 hour. To the reaction mixture was added water and extracted with ethyl acetate. The resulting ethyl acetate layer was washed with brine, dried over anhydrous magnesium sulfate, and filtered. The filtrate was concentrated in vacuo. The resulting residue was purified by a silica gel column chromatography (eluent: hexane to hexane/ethyl acetate=3/1) to give the title compound as a pale yellow oil.

(8) Synthesis of trans-4-(3-chloro-2-fluorophenoxy)-1-(6-(1,3-thiazol-2-ylamino)pyridin-2-yl)methyl) cyclohexanecarboxylic acid hydrochloride

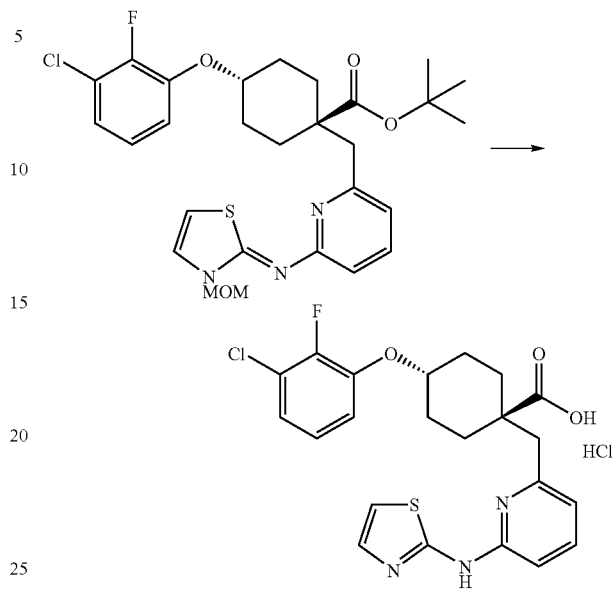

To a 3.9 g of tert-butyl trans-4-(3-chloro-2-fluorophenoxy)-1-((6-(((2Z)-3-(methoxymethyl)-1,3-thiazol-2(3H)-ylidene)amino)pyridin-2-yl)methyl)cyclohexanecarboxylate was added 100 ml of 4 M hydrogen chloride in 1,4-dioxane, followed by stirring the reaction mixture at 90° C. for 5 hours. After cooling the reaction mixture to room temperature, 100 ml of tert-butylmethylether was added to the mixture. The resulting precipitate was collected by filtration and washed with tert-butylmethylether to give a colorless solid.

The resulting colorless solid was dissolved in 1.2 l of ethanol at 80° C. The ethanol was distilled away to reduce to about one-third of the solution volume. The resulting solution was cooled to room temperature, followed by stirring at room temperature overnight. The resulting solid was collected by filtration and washed with cooled ethanol to obtain the title compound as a colorless crystal.

$^1$H-NMR(DMSO-$d_6$)δ: 1.60-1.92(8H,m), 3.03(2H,s), 4.62 (1H,brs), 6.90(1H,d,J=7.4 Hz), 7.05-7.22(5H,m), 7.53(1H,d, J=4.1 Hz), 7.74(1H,t,J=7.8 Hz).

mass:462,464(M+1)$^+$

Example 2

Synthesis of trans-4-(3-chloro-2-fluorophenoxy)-1-(6-(1,3-thiazol-2-ylamino)pyridin-2-yl)methyl)cyclohexanecarboxylic acid

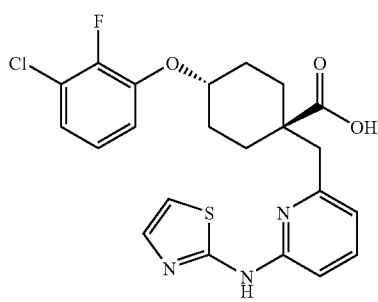

[Method A]

To a 47.9 mg of trans-4-(3-chloro-2-fluorophenoxy)-1-(6-(1,3-thiazol-2-ylamino)pyridin-2-yl)methyl)cyclohexanecarboxylic acid hydrochloride as obtained in Example 1 were successively added 4 ml of water and 4 ml of ethanol, followed by stirring the reaction mixture at room temperature for 12 hours. The resulting precipitate was collected by filtration and washed with water to give the title compound as a colorless needle (mp: 202-222° C.).

$^1$H-NMR(DMSO-d$_6$)δ: 1.60-1.92(8H,m), 2.98(2H,s), 4.61 (1H,brs), 6.71 (1H,d,J=7.2 Hz), 6.90(1H,d,J=8.2 Hz), 6.98 (1H,d,J=3.5 Hz), 7.10-7.22(3H,m), 7.38(1H,d,J=3.5 Hz), 7.60(1H,t,J=7.6 Hz).

mass:462,464(M+1)$^+$

[Method B]

To 460 mg of trans-4-(3-chloro-2-fluorophenoxy)-1-(6-(1,3-thiazol-2-ylamino)pyridin-2-yl)methyl)cyclohexanecarboxylic acid hydrochloride as obtained in Example 1 were successively added 40 ml of water and 40 ml of ethanol, followed by stirring the reaction mixture at room temperature for 4 days. The resulting precipitate was collected by filtration and washed with water to give the title compound as a colorless plate (mp: 224-242° C.).

$^1$H-NMR(DMSO-d$_6$)δ: 1.60-1.92(8H,m), 2.98(2H,s), 4.61 (1H,brs), 6.71 (1H,d,J=7.2 Hz), 6.90(1H,d,J=8.2 Hz), 6.98 (1H,d,J=3.5 Hz), 7.10-7.22(3H,m), 7.38(1H,d,J=3.5 Hz), 7.60(1H,t,J=7.6 Hz).

mass:462,464(M+1)$^+$

Example 3

Synthesis of trans-4-(2,3-difluorophenoxy)-1-((6-(1,3-thiazol-2-ylamino)pyridin-2-yl)methyl)cyclohexanecarboxylic acid hydrochloride

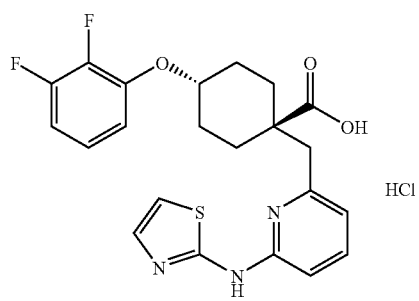

The title compound was obtained as a white solid in the same manner as in Example 1 using 2,3-difluorophenol, instead of 3-chloro-2-fluorophenol as used in the step of Example 1(7).

$^1$H-NMR(DMSO-d$_6$)δ: 1.60-1.92(8H,m),3.02(2H,s),4.62 (1H,brs),6.84(1H,d,J=8.4 Hz),6.97-7.15(5H,m),7.49(1H,d,J=3.7 Hz),7.70(1H,t,J=7.8 Hz).

mass:446(M+1)$^+$

Example 4

Synthesis of trans-4-(2-fluoro-3-(trifluoromethyl)phenoxy)-1-((6-(1,3-thiazol-2-ylamino)pyridin-2-yl)methyl)cyclohexanecarboxylic acid hydrochloride

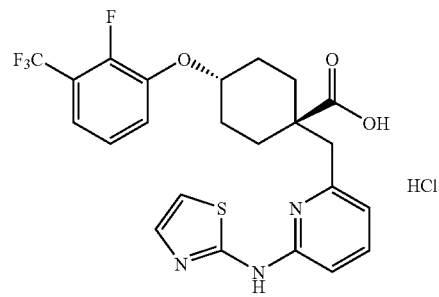

The title compound was obtained as a white solid in the same manner as in Example 1 using 2-fluoro-3-(trifluoromethyl)phenol, instead of 3-chloro-2-fluorophenol as used in the step of Example 1(7).

$^1$H-NMR(DMSO-d$_6$)δ: 1.62-1.95(8H,m),3.03(2H,s),4.68 (1H,brs),6.89(1H,d,J=7.2 Hz),7.07(1H,d,J=8.4 Hz),7.15(1H,d,J=3.7 Hz), 7.28-7.35(2H,m),7.52(1H,d,J=3.7 Hz),7.56(1H,t,J=6.8 Hz),7.73(1H,t,J=7.8 Hz).

mass:496(M+1)$^+$

Example 5

Synthesis of trans-4-(3-chlorophenoxy)-1-((6-(1,3-thiazol-2-ylamino)pyridin-2-yl)methyl)cyclohexanecarboxylic acid hydrochloride

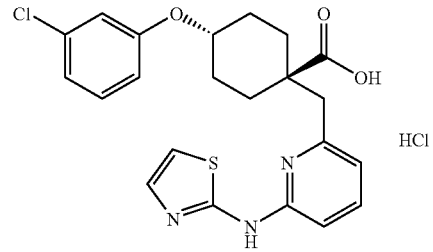

The title compound was obtained as a white solid in the same manner as in Example 1 using 3-chlorophenol, instead of 3-chloro-2-fluorophenol as used in the step of Example 1(7).

$^1$H-NMR(CDCl$_3$)δ: 1.71-1.87(4H,m), 1.95-2.13(4H,m), 3.12(2H,brs),4.54(1H,brs),6.45(1H,brs),6.80-7.01 (5H,m), 7.17-7.25(2H,m),7.65(1H,t,J=7.8 Hz).

mass:444,446(M+1)$^+$

Example 6

Synthesis of trans-4-(2,3-dichlorophenoxy)-1-((6-(1,3-thiazol-2-ylamino)pyridin-2-yl)methyl)cyclohexanecarboxylic acid hydrochloride

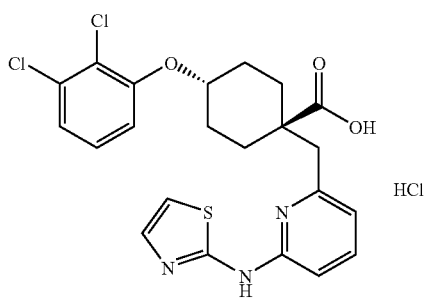

The title compound was obtained as a white solid in the same manner as in Example 1 using 2,3-dichlorophenol instead of 3-chloro-2-fluorophenol as used in the step of Example 1(7).

$^1$H-NMR(DMSO-d$_6$)δ: 1.51-1.66(2H,m),1.69-1.89(6H,m),2.97(2H,s),4.72(1H,brs),6.75-6.85(1H,m),6.95-7.10(2H,m),7.10-7.16(2H,m),7.25(1H,t,J=8.2 Hz),7.42-7.49(1H,m),7.62-7.72(1H,m).

mass:478,480(M+1)$^+$

Example 7

Synthesis of trans-1-((6-(1,3-thiazol-2-ylamino)pyridin-2-yl)methyl)-4-(3-(trifluoromethyl)phenoxy)cyclohexanecarboxylic acid hydrochloride

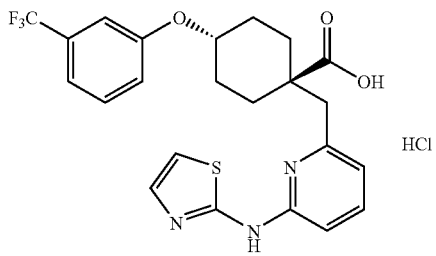

The title compound was obtained as a white solid in the same manner as in Example 1 using 3-(trifluoromethyl)phenol instead of 3-chloro-2-fluorophenol as used in the step of Example 1(7).

$^1$H-NMR(CD$_3$OD)δ: 1.72-1.90(4H,m), 1.91-2.04(4H,m), 3.18(2H,s),4.60-4.66(1H,m),7.09-7.16(3H,m),7.16-7.22(2H,m),7.27(1H,d,J=4.3 Hz),7.45(1H,t,J=8.0 Hz),7.57(1H,d,J=4.3 Hz),7.87(1H,t,J=7.9 Hz).

mass:478(M+1)$^+$

Example 8

Synthesis of trans-4-(3-chloro-2-fluorophenoxy)-1-((6-(1,3-thiazol-2-ylamino)pyridin-2-yl)methyl)cyclohexanecarboxamide

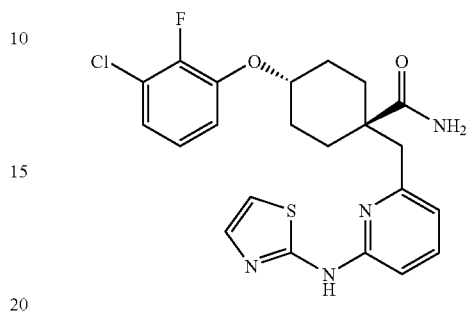

To a solution of 20 mg of trans-4-(3-chloro-2-fluorophenoxy)-1-((6-(1,3-thiazol-2-ylamino)pyridin-2-yl)methyl)cyclohexanecarboxylic acid hydrochloride as obtained in Example 1 in 3 ml of chloroform were successively added 21 mg of ammonium chloride, 0.056 ml of triethylamine, 31 mg of hydroxybenzotriazole hydrate and 38 mg of 1-(3-dimethylaminopropyl)-3-ethylcarbodiimide hydrochloride at room temperature, followed by stirring the reaction mixture at room temperature overnight. After adding saturated aqueous sodium bicarbonate solution to the reaction mixture, the mixture was extracted with ethyl acetate. The resulting ethyl acetate solution was dried over anhydrous magnesium sulfate and filtered. The filtrate was concentrated in vacuo. The obtained residue was purified by a preparative thin-layer chromatography (Kieselgel™60F$_{254}$, Art5744 (Merck), chloroform/methanol=10/1) to give the title compound as a white solid.

$^1$H-NMR(DMSO-d$_6$)δ: 1.63-1.93(8H,m),2.92(2H,s),4.55(1H,brs),6.68(1H,d,J=7.4 Hz),6.85(1H,d,J=8.4 Hz),6.94(2H,d,J=3.1 Hz), 7.05-7.20(3H,m),7.25(1H,s),7.35(1H,d,J=3.5 Hz),7.55(1H,t,J=7.8 Hz), 11.13(1H,s).

mass:461,463(M+1)$^+$

Example 9

Synthesis of trans-4-(2-fluoro-3-(trifluoromethyl)phenoxy)-1-((6-(1H-pyrazol-3-ylamino)pyridin-2-yl)methyl)cyclohexanecarboxylic acid trifluoroacetate

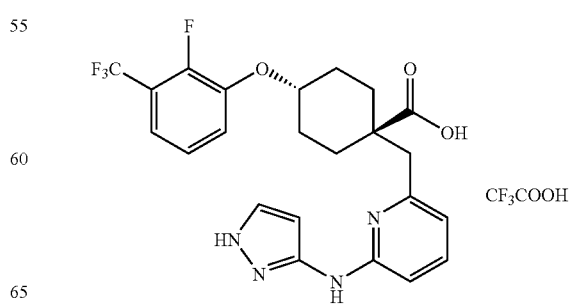

(1) Synthesis of 2-bromo-6-(bromomethyl)pyridine

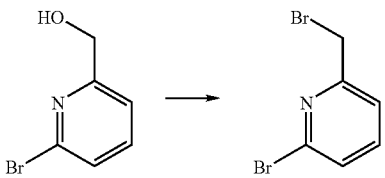

To a solution of 498 mg of (6-bromo-pyridin-2-yl)methanol in 6 ml of N,N-dimethylformamide were successively added 1.15 ml of diisopropylethylamine and a solution of 695 mg of methanesulfonic anhydride in 2 ml of N,N-dimethylfornamide under cooling with ice, followed by stirring the reaction mixture at room temperature for 20 minutes. Then 693 mg of lithium bromide was added to the solution, followed by stirring the reaction mixture at room temperature for 1 hour. After adding saturated aqueous sodium bicarbonate solution to the reaction mixture, the mixture was extracted with ethyl acetate. The resulting ethyl acetate solution was dried over anhydrous magnesium sulfate and filtered. The filtrate was concentrated in vacuo. The resulting residue was purified by a silica gel column chromatography (eluent: hexane/ethyl acetate=20/1-3/2) to give the title compound as a pale yellow solid.

(2) Synthesis of tert-butyl cis-1-((6-bromopyridin-2-yl)methyl)-4-((tert-butyl(diphenyl)silyl)oxy)cyclohexanecarboxylate

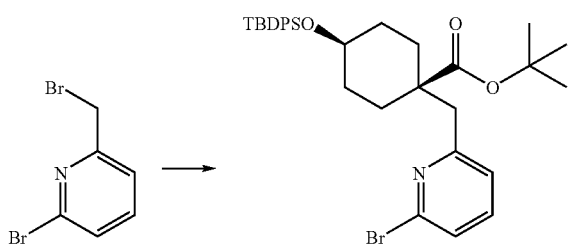

To a solution of 0.82 ml of diisopropylamine in 20 ml of tetrahydrofuran was added 3.7 ml of a hexane solution containing 1.58M n-butyl lithium under cooling with ice, followed by stirring the reaction mixture for 30 minutes. After cooling down the reaction mixture to −78° C., a solution of 2.67 g of tert-butyl 4-((tert-butyl(diphenyl)silyl)oxy)cyclohexanecarboxylate as obtained in Reference 1 in 10 ml of tetrahydrofuran was added to the solution, and the resultant solution was stirred for 1 hour at −78° C. To the reaction mixture were added a solution of 980 mg of 2-bromo-6-(bromomethyl)pyridine and 2.7 ml of hexamethylphosphoramide in 5 ml of tetrahydrofuran, followed by gradually warming up the reaction mixture to room temperature, and then the reaction mixture was stirred at room temperature overnight. To the reaction mixture was added saturated aqueous ammonium chloride solution, followed by extraction with chloroform. The resulting chloroform solution was dried over anhydrous magnesium sulfate, and filtered. The filtrate was concentrated in vacuo. The resulting residue was purified by a silica gel column chromatography (eluent: hexane/ethyl acetate=100/1-9/1) to give the title compound as a pale yellow oil.

(3) Synthesis of tert-butyl cis-1-((6-bromopyridin-2-yl)methyl)-4-hydroxycyclohexanecarboxylate

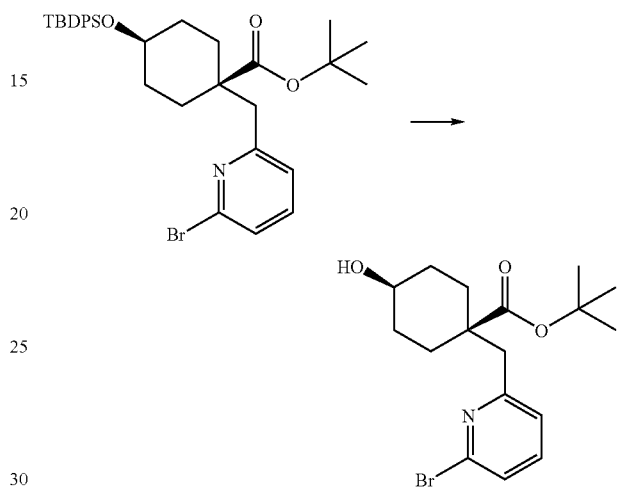

To a solution of 1.6 g of tert-butyl cis-1-((6-bromopyridin-2-yl)methyl)-4-((tert-butyl(diphenyl)silyl)oxy)cyclohexanecarboxylate in 30 ml of tetrahydrofuran was added 16 ml of tetrahydrofuran solution containing 1 M tetrabutylammonium fluoride at room temperature, followed by stirring the reaction mixture at 60° C. overnight. The reaction mixture was cooled to room temperature, followed by dilution with chloroform. The resulting solution was successively washed with a pH 6.8 phosphate buffer solution and brine, dried over anhydrous magnesium sulfate, and filtered. The filtrate was concentrated in vacuo. The obtained residue was purified by a silica gel column chromatography (eluent: hexane/ethyl acetate=8/1 to ethyl acetate) to give the title compound as a pale yellow solid.

(4) Synthesis of tert-butyl trans-1-((6-bromopyridin-2-yl)methyl)-4-(2-fluoro-3-(trifluoromethyl)phenoxy)cyclohexanecarboxylate

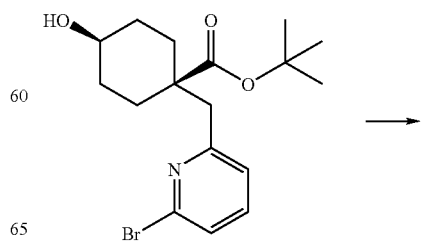

-continued

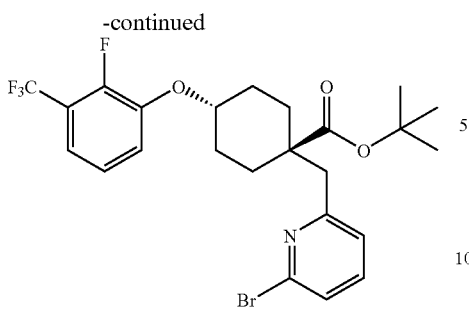

To a solution of 150 mg of tert-butyl cis-1-((6-bromopyridin-2-yl)methyl)-4-hydroxycyclohexanecarboxylate, 219 mg of 2-fluoro-3-(trifluoromethyl)phenol and 320 mg of triphenylphosphine in 2.5 ml of tetrahydrofuran was added 0.24 ml of diisopropyl azodicarboxylate under cooling with ice, followed by stirring the reaction mixture at room temperature for 15 minutes. The reaction mixture was concentrated in vacuo, and the resulting residue was purified by a silica gel column chromatography (eluent: hexane/ethyl acetate=50/1-4/1) to give the title compound as a pale yellow oil.

(5) Synthesis of tert-butyl trans-1-((6-((1-tert-butyl-1H-pyrazol-5-yl)amino)pyridin-2-yl)methyl)-4-(2-fluoro-3-(trifluoromethyl)phenoxy)cyclohexanecarboxylate

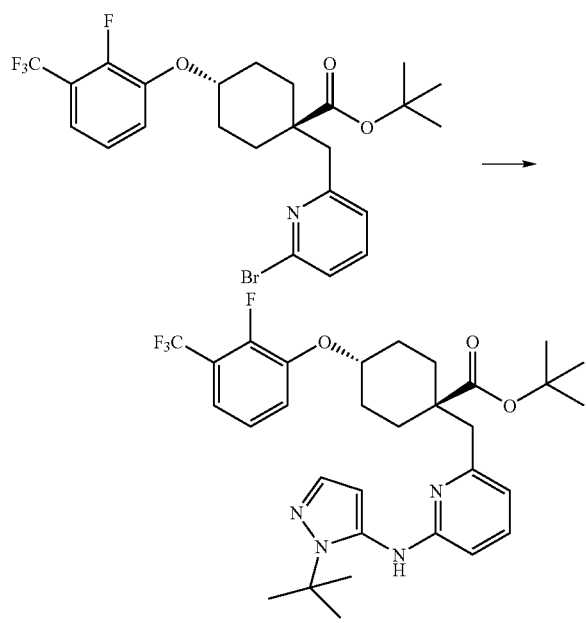

A mixture of 140 mg of tert-butyl trans-1-((6-bromopyridin-2-yl)methyl)-4-(2-fluoro-3-(trifluoromethyl)phenoxy)cyclohexanecarboxylate, 102 mg of 1-tert-butyl-1H-pyrazol-5-amine p-toluenesulfonate as obtained in Reference 4, 25.4 mg of 9,9-dimethyl-4,5-bis(diphenylphosphino)xanthene, 21.6 mg of tris(dibenzylideneacetone)dipalladium(0)-chloroform complex, 139 mg of potassium phosphate and 4 ml of 1,4-dioxane was stirred at 100° C. overnight, followed by cooling down to room temperature. An insoluble matter was filtered off using Celite and washed with ethyl acetate. The resulting ethyl acetate solution was washed with water, dried over anhydrous sodium sulfate, and filtered. The filtrate was concentrated in vacuo. The resulting residue was purified by a silica gel column chromatography (eluent: hexane/ethyl acetate=20/1-3/2) to give the title compound as a pale yellow oil.

(6) Synthesis of trans-4-(2-fluoro-3-(trifluoromethyl)phenoxy)-1-((6-(1H-pyrazol-3-ylamino)pyridin-2-yl)methyl)cyclohexanecarboxylic acid trifluoroacetate

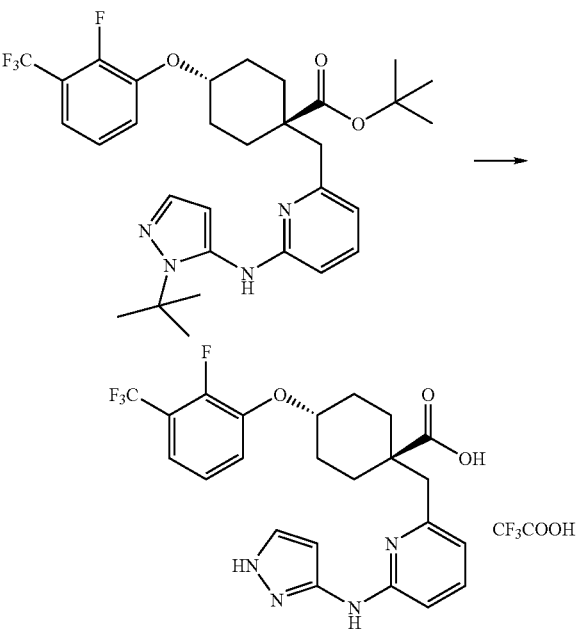

A solution of 88.8 mg of tert-butyl trans-1-((6-((1-tert-butyl-1H-pyrazol-5-yl)amino)pyridin-2-yl)methyl)-4-(2-fluoro-3-(trifluoromethyl)phenoxy)cyclohexanecarboxylate of 1 ml of formic acid was stirring at 110° C. for 1 hour. The reaction mixture was cooled to room temperature, followed by concentration in vacuo. The resulting residue was purified by a reversed phase preparative liquid chromatography, followed by concentrating the obtained fraction in vacuo to give the title compound as a pale yellow solid.

$^1$H-NMR(CD$_3$OD):δ: 1.82-2.17(8H,m),3.24(2H,s),4.70 (1H,s),6.18(1H,d,J=2.8 Hz),7.05(1H,d,J=7.2 Hz),7.19-7.31 (3H,m),7.45(1H,dt,J=8.4,2.8 Hz),7.78(1H,d,J=2.4 Hz),8.06 (1H,dd,J=8.8,7.2 Hz).
mass:479(M+1)$^+$ Example 10

Synthesis of trans-4-(3-chloro-2-fluorophenoxy)-1-((6-(1H-pyrazol-3-ylamino)pyridin-2-yl)methyl) cyclohexanecarboxylic acid trifluoroacetate

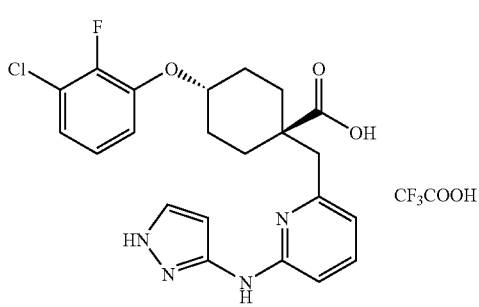

The title compound was obtained as a white solid in the same manner as in Example 9 using 3-chloro-2-fluorophenol, instead of 2-fluoro-3-trifluoromethyl)phenol as used in the step of Example 9(4).

$^1$H-NMR(CD$_3$OD)δ: 1.79-2.15(8H,m),3.20(2H,s),4.62 (1H,s),6.18(1H,d,J=2.4 Hz),7.01-7.15(4H,m),7.20(1H,d,J=8.8 Hz),7.79(1H,d,J=2.4 Hz),8.04(1H,dd,J=8.8,7.2 Hz).

mass:445,447(M+1)$^+$

Example 11

Synthesis of trans-4-(3-chloro-2-fluorophenoxy)-1-((6-(1H-pyrazol-3-ylamino)pyridin-2-yl)methyl)cyclohexanecarboxamide

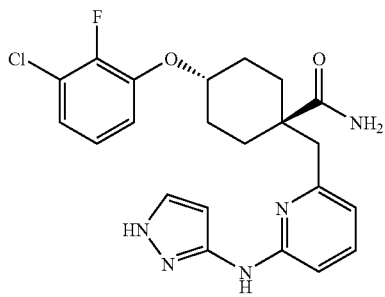

To a solution of 32.1 mg of trans-4-(3-chloro-2-fluorophenoxy)-1-((6-(1H-pyrazol-3-ylamino)pyridin-2-yl)methyl)cyclohexanecarboxylic acid trifluoroacetate as obtained in Example 10 in 1 ml of dimethylsulfoxide were successively added 7.5 mg of ammonium chloride, 0.038 ml of triethylamine, 20.2 mg of hydroxybenzotriazole hydrate and 24.6 mg of 1-(3-dimethylaminopropyl)-3-ethylcarbodiimide hydrochloride at room temperature, followed by stirring the reaction mixture at room temperature overnight. The reaction mixture was purified by a reversed phase preparative liquid chromatography, followed by a preparative thin-layer chromatography (NH-PLC05 (FUJI SILYSIA CHEMICAL), chloroform/methanol=20/1) to give the title compound as a white solid.

$^1$H-NMR(CD$_3$OD)δ: 1.82-2.00(8H,m),3.04(2H,s),4.55 (1H,s),5.75(1H,brs),6.60-6.80(2H,m),7.00-7.10(3H,m),7.44 (1H,brs),7.50(1H,t,J=8.0 Hz).

mass:444,446(M+1)$^+$

Example 12

Synthesis of trans-4-(3-chloro-2-fluorophenoxy)-N-methyl-1-((6-(1H-pyrazol-3-ylamino)pyridin-2-yl)methyl)cyclohexanecarboxamide

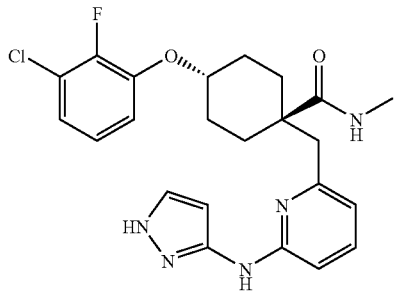

The title compound was obtained as a white solid in the same manner as in Example 11 using methylamine hydrochloride, instead of ammonium chloride as used in Example 11.

$^1$H-NMR(CD$_3$OD)δ: 1.73-2.03(8H,m),2.62(3H,s),2.98 (2H,s),4.54(1H,s),6.08(1H,brs),6.62(1H,d,J=7.2 Hz),6.70-6.80(1H,m),7.01-7.11 (3H,m),7.46(1H,brs),7.49(1H,t,J=7.6 Hz).

mass:458,460(M+1)$^+$

Example 13

Synthesis of trans-4-(3-chloro-2-fluorophenoxy)-N,N-dimethyl-1-((6-(1H-pyrazol-3-ylamino)pyridin-2-yl)methyl)cyclohexanecarboxamide

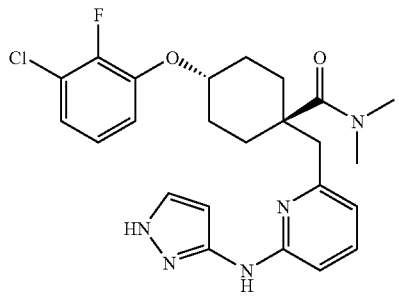

The title compound was obtained as a white solid in the same manner as in Example 11 using dimethylamine hydrochloride, instead of ammonium chloride as used in Example 11.

$^1$H-NMR(CD$_3$OD)δ: 1.75-1.87(2H,m), 1.90-2.03(4H,m), 2.18-2.30(2H,m),3.02(3H,brs),3.10(3H,brs),4.56(1H,s),5.83 (1H,brs),6.55-6.80(2H,m),7.00-7.10(3H,m),7.35-7.65(2H, m).

mass:472,474(M+1)$^+$

Example 14

Synthesis of trans-4-(3-chloro-2-fluorophenoxy)-1-((6-(1H-pyrazol-3-ylamino)pyrazin-2-yl)methyl)cyclohexanecarboxylic acid trifluoroacetate

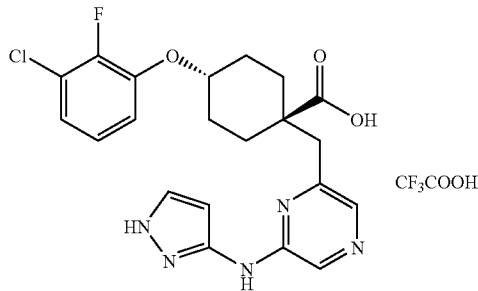

(1) Synthesis of N-(1-tert-butyl-1H-pyrazol-5-yl)-6-chloropyrazin-2-amine

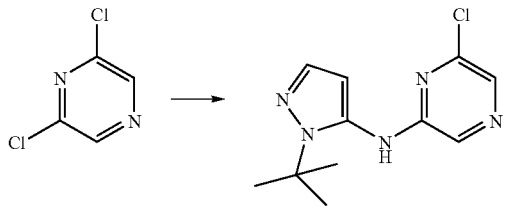

A mixture of 60.6 g of 2,6-dichloropyrazine, 62.2 g of 1-tert-butyl-1H-pyrazol-5-amine as obtained in Reference 3, 23.5 g of 9,9-dimethyl-4,5-bis(diphenylphosphino)xanthene, 21.0 g of tris(dibenzylideneacetone)dipalladium(0)-chloroform complex, 172.6 g of potassium phosphate and 1.17 l of 1,4-dioxane was stirred at 100° C. overnight, followed by cooling down to room temperature. An insoluble matter was filtered off using Celite and washed with ethyl acetate. The resulting ethyl acetate solution was washed with water and brine, dried over anhydrous magnesium sulfate and filtered. The filtrate was concentrated in vacuo. The obtained residue was purified by a silica gel column chromatography (eluent: hexane/ethyl acetate=4/1-2/1) to give the title compound as a yellow solid.

(2) Synthesis of N-(1-tert-butyl-1H-pyrazol-5-yl)-6-vinylpyrazin-2-amine

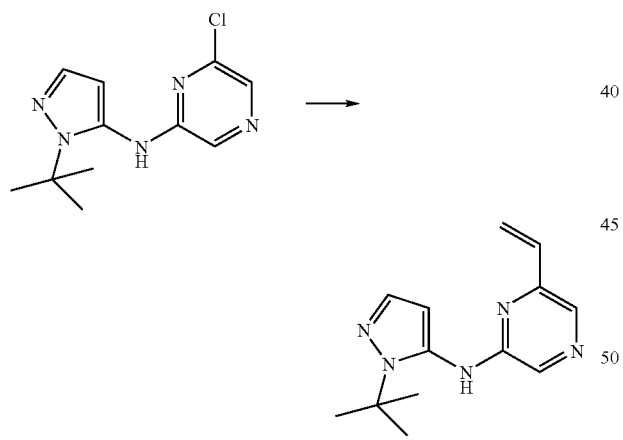

A mixture of 65.04 g of N-(1-tert-butyl-1H-pyrazol-5-yl)-6-chloropyrazin-2-amine, 41.6 g of potassium vinyltrifluoroborate, 4.22 g of (1,1'-bis (diphenylphosphino)ferrocene) dichloropalladium(II) dichloromethane complex, 72 ml of triethylamine and 685 ml of 1-propanol was stirred at 110° C. overnight, followed by cooling down to room temperature and concentrated in vacuo. The obtained residue was diluted with ethyl acetate, and an insoluble matter was filtered off using Celite. The resulting ethyl acetate solution was washed with water, dried over anhydrous magnesium sulfate and filtered. The filtrate was concentrated in vacuo. The obtained residue was suspended in 100 ml of ethyl acetate, and 400 ml of diisopropylether was added to the mixture. The obtained precipitate was collected to give the title compound as a pale brown solid.

(3) Synthesis of 6-((1-tert-butyl-1H-pyrazol-5-yl)amino)pyrazin-2-carbaldehyde

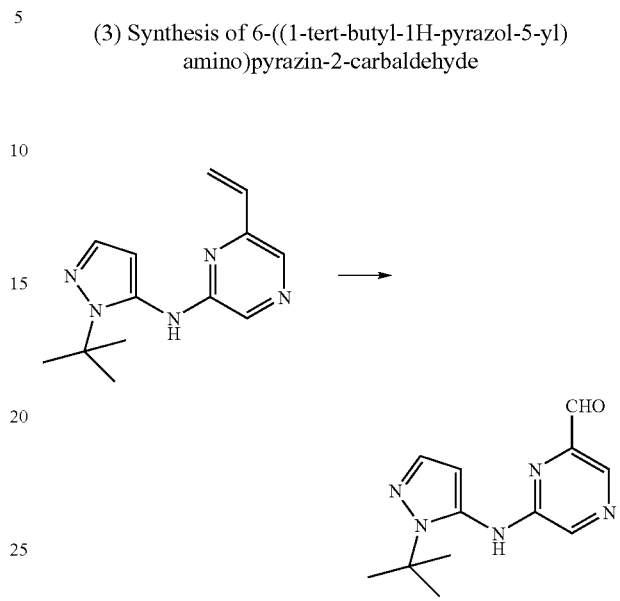

To a solution of 56.36 g of N-(1-tert-butyl-1H-pyrazol-5-yl)-6-vinylpyrazin-2-amine in 570 ml of acetonitrile were successively added 48.9 g of N-methylmorpholine N-oxide and 215 ml of 0.1M aqueous osmium tetraoxide solution at room temperature, followed by stirring the reaction mixture at room temperature overnight. After adding 73 g of sodium sulfite and 580 ml of water to the reaction mixture, the mixture was extracted with ethyl acetate. The resulting ethyl acetate solution was washed with brine, dried over anhydrous magnesium sulfate and filtered. The filtrate was concentrated in vacuo to give the crude product.

To a solution of the obtained residue in 572 ml of acetonitrile and 858 ml of water was added 62.8 g of sodium periodate under cooling with ice, followed by stirring the reaction mixture at room temperature for 3 hours. The reaction mixture was diluted with water, and extracted with ethyl acetate. The resulting ethyl acetate solution was washed with brine, dried over anhydrous magnesium sulfate and filtered. The filtrate was concentrated in vacuo. The obtained residue was purified by a silica gel column chromatography (eluent: chloroform to chloroform/methanol=20/1) to give the title compound as a dark brown oil.

(4) Synthesis of (6-((1-tert-butyl-1H-pyrazol-5-yl)amino)pyrazin-2-yl)methanol

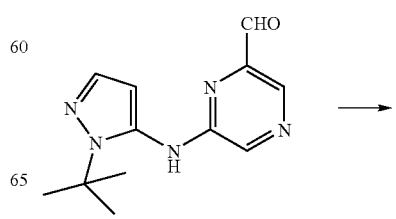

-continued

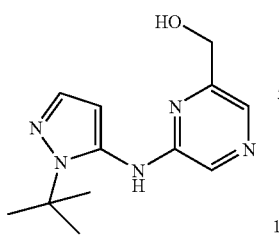

To a solution of 14.99 g of 6-((1-tert-butyl-1H-pyrazol-5-yl)amino)pyrazin-2-carbaldehyde in 235 ml of ethanol was added 2.31 g of sodium borohydride under cooling with ice, followed by stirring the reaction mixture for 1 hour. After slowly adding 61 ml of 1M hydrochloric acid to the reaction mixture under cooling with ice, ethanol was concentrated in vacuo. The obtained residue was diluted with water, and extracted with chloroform. The resulting chloroform solution was washed with brine, dried over anhydrous magnesium sulfate and filtered. The filtrate was concentrated in vacuo. The obtained residue was purified by a silica gel column chromatography (eluent: chloroform to chloroform/methanol=20/1) to give the title compound as a brown solid.

(5) Synthesis of N-(1-tert-butyl-1H-pyrazol-5-yl)-6-(chloromethyl)pyrazin-2-amine

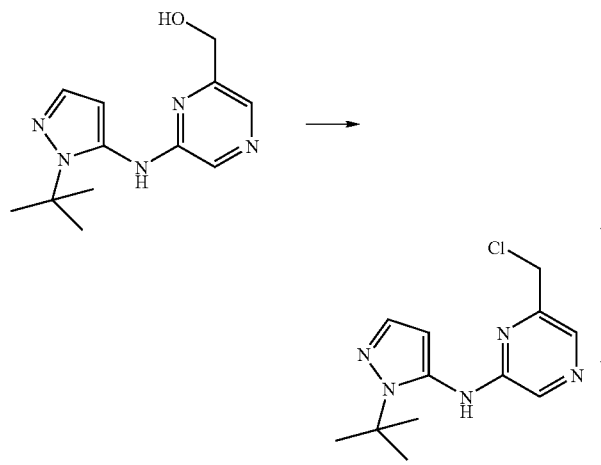

To a solution of 507.3 mg of (6-((1-tert-butyl-1H-pyrazol-5-yl)amino)pyrazin-2-yl)methanol in 6.8 ml of chloroform were successively added 1.08 ml of diisopropylethylamine and 0.24 ml of methylsulfonyl chloride under cooling with ice, followed by stirring the reaction mixture at room temperature for 1.5 hours. To the reaction mixture were successively added 442.9 mg of lithium chloride and 6.8 ml of N,N-dimethylformamide, followed by stirring the reaction mixture at room temperature for 2 hours. After diluting the reaction mixture with ethyl acetate, the ethyl acetate solution was successively washed with water and brine, dried over anhydrous magnesium sulfate and filtered. The filtrate was concentrated in vacuo. The resulting residue was purified by a silica gel column chromatography (eluent: hexane/ethyl acetate=20/1-1/4) to give the title compound as a yellow solid.

(6) Synthesis of tert-butyl cis-4-((tert-butyl(diphenyl)silyl)oxy)-1-((6-(((1-tert-butyl-1H-pyrazol-5-yl)amino)pyrazin-2-yl)methyl)cyclohexanecarboxylate

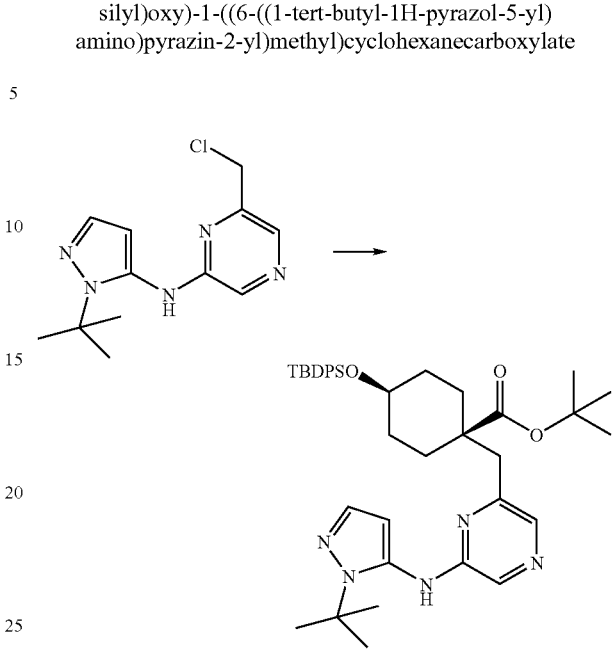

To a solution of 0.15 ml of diisopropylamine in 4.2 ml of tetrahydrofuran was added 0.7 ml of a hexane solution containing 1.58M n-butyl lithium under cooling with ice, followed by stirring the reaction mixture for 30 minutes. After cooling down to −78° C., a solution of 488 mg of tert-butyl 4-((tert-butyl(diphenyl)silyl)oxy)cyclohexanecarboxylate as obtained in Reference 1 in 2 ml of tetrahydrofuran was added to the solution. The resultant solution was stirred for 1 hour at −78° C. To the reaction mixture were added a solution of 115 mg of N-(1-tert-butyl-1H-pyrazol-5-yl)-6-(chloromethyl)pyrazin-2-amine and 0.5 ml of hexamethylphosphoramide in 1.5 ml of tetrahydrofuran, followed by gradually warming up the reaction mixture to room temperature. The reaction mixture was stirred at room temperature overnight. To the reaction mixture was added saturated aqueous ammonium chloride solution, followed by extraction with chloroform. The resulting chloroform solution was dried over anhydrous magnesium sulfate, filtered. The filtrate was concentrated in vacuo. The resulting residue was purified by a silica gel column chromatography (eluent: hexane to hexane/ethyl acetate=1/4) to give the title compound as a yellow oil.

(7) Synthesis of tert-butyl cis-1-((6-(((1-tert-butyl-1H-pyrazol-5-yl)amino)pyrazin-2-yl)methyl)-4-hydroxycyclohexanecarboxylate

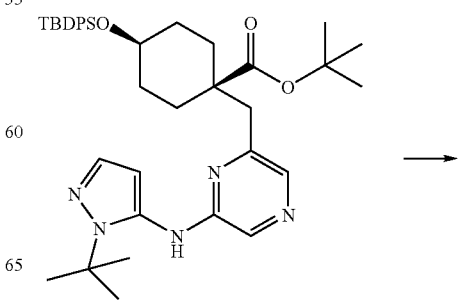

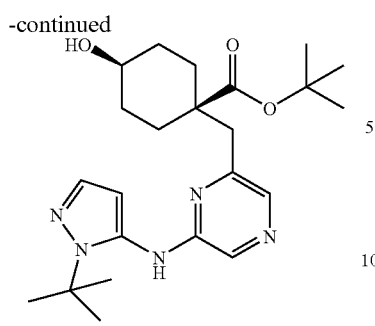

To a solution of 60.5 mg of tert-butyl cis-4-((tert-butyl(diphenyl)silyl)oxy)-1-((6-((1-tert-butyl-1H-pyrazol-5-yl)amino)pyrazin-2-yl)methyl)cyclohexanecarboxylate in 1 ml of tetrahydrofuran was added 0.36 ml of tetrahydrofuran solution containing 1 M tetrabutylammonium fluoride at room temperature, followed by stirring the reaction mixture at 60° C. overnight. The reaction mixture was cooled to room temperature, followed by dilution with chloroform. The resulting solution was successively washed with a pH 6.8 phosphate buffer solution and brine, dried over anhydrous magnesium sulfate, and filtered. The filtrate was concentrated in vacuo. The obtained residue was purified by a silica gel column chromatography (eluent: chloroform/methanol=50/1-4/1) to give the title compound as a yellow oil.

(8) Synthesis of tert-butyl trans-1-((6-((1-tert-butyl-1H-pyrazol-5-yl)amino)pyrazin-2-yl)methyl)-4-(3-chloro-2-fluorophenoxy)cyclohexanecarboxylate

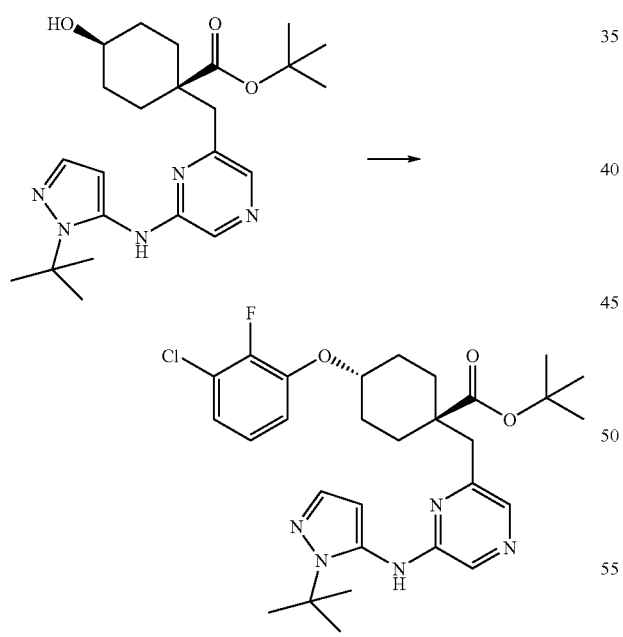

To a solution of 28.9 mg of tert-butyl cis-1-((6-((1-tert-butyl-1H-pyrazol-5-yl)amino)pyrazin-2-yl)methyl)-4-hydroxycyclohexanecarboxylate, 30 mg of 3-chloro-2-fluorophenol and 52.2 mg of triphenylphosphine in 0.5 ml of tetrahydrofuran was added 0.04 ml of diisopropyl azodicarboxylate under cooling with ice, followed by stirring the reaction mixture at room temperature overnight. The reaction mixture was concentrated in vacuo, and the resulting residue was purified by a preparative thin-layer chromatography (NH-PLC05 (FUJI SILYSIA CHEMICAL), hexane/ethyl acetate=1/1) to give the title compound as a yellow oil.

(9) Synthesis of trans-4-(3-chloro-2-fluorophenoxy)-1-((6-(1H-pyrazol-3-ylamino)pyrazin-2-yl)methyl)cyclohexanecarboxylic acid trifluoroacetate

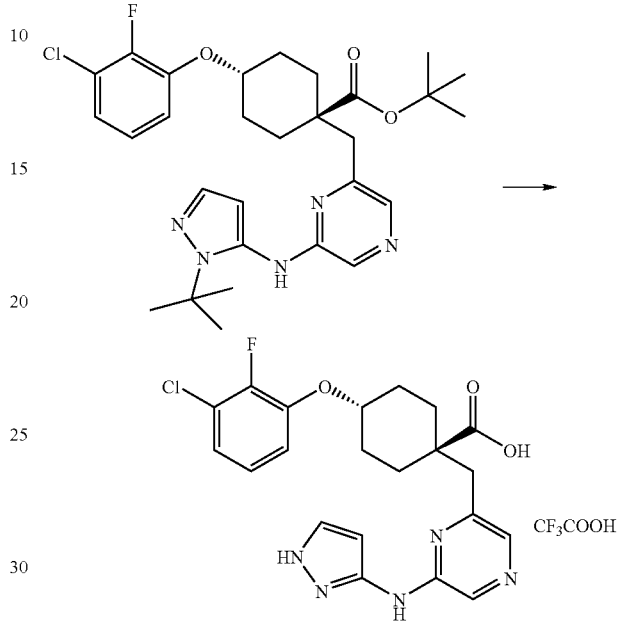

A solution of 16.2 mg of tert-butyl trans-1-((6-((1-tert-butyl-1H-pyrazol-5-yl)amino)pyrazin-2-yl)methyl)-4-(3-chloro-2-fluorophenoxy)cyclohexanecarboxylate in 0.5 ml of formic acid was stirred at 100° C. for 1.5 hours. The reaction mixture was cooled to room temperature, followed by concentration in vacuo. The resulting residue was purified by a reversed phase preparative liquid chromatography, followed by concentrating the obtained fraction in vacuo to give the title compound as a pale yellow solid.

$^1$H-NMR(CD$_3$OD)δ: 1.75-2.04(8H,m),3.05(2H,s),4.53-4.59(1H,m),6.39(1H,d,J=2.4 Hz),6.98-7.09(3H,m),7.62(1H, d,J=2.4 Hz),7.84(1H,s),8.17(1H,s).

mass:446,448(M+1)$^+$

Example 15

Synthesis of trans-4-(3-chloro-2-fluorophenoxy)-1-((6-(1H-pyrazol-3-ylamino)pyrazin-2-yl)methyl)cyclohexanecarboxamide

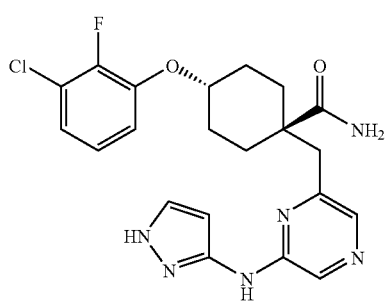

The title compound was obtained as a pale yellow solid in the same manner as in Example 11 using trans-4-(3-chloro-2-fluorophenoxy)-1-((6-(1H-pyrazol-3-ylamino)pyrazin-2-yl)methyl)cyclohexanecarboxylic acid trifluoroacetate as obtained in Example 14, instead of trans-4-(3-chloro-2-fluorophenoxy)-1-((6-(1H-pyrazol-3-ylamino)pyridin-2-yl)methyl)cyclohexanecarboxylic acid trifluoroacetate as used in Example 11.

$^1$H-NMR(DMSO-$d_6$)δ: 1.62-1.93(8H,m),2.82(2H,s),4.54(1H,brs),6.50(1H,brs),6.93(1H,brs),7.06-7.22(3H,m),7.26(1H,brs),7.55(1H,brs),7.67(1H,s),8.28(1H,brs),9.60(1H,brs).

mass:445,447(M+1)$^+$

Example 16

Synthesis of trans-4-(3-chloro-2-fluorophenoxy)-1-((6-(1H-pyrazol-3-ylamino)pyridin-2-yl)methyl)cyclohexanecarbonitrile

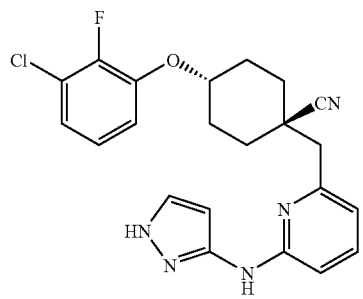

(1) Synthesis of trans-4-(3-chloro-2-fluorophenoxy)-1-((6-((1-((2-(trimethylsilyl)ethoxy)methyl)-1H-pyrazol-3-yl)amino)pyridin-2-yl)methyl)cyclohexanecarbonitrile

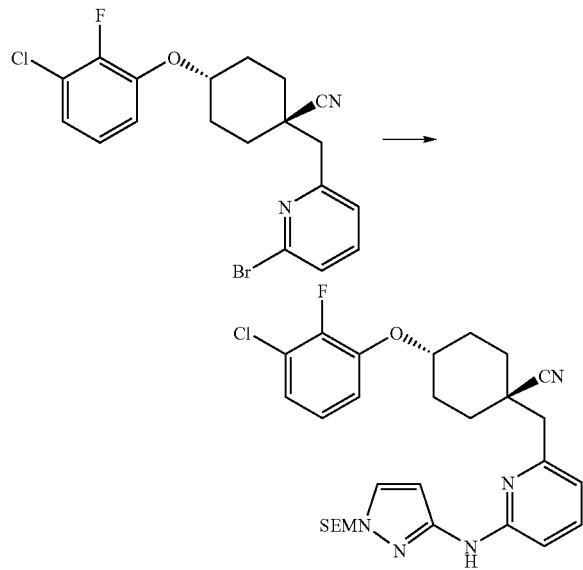

A mixture of 71.2 mg of trans-1-((6-bromopyridin-2-yl)methyl)-4-(3-chloro-2-fluorophenoxy)cyclohexanecarbonitrile synthesized in the same manner as in the steps of Example 9(2) to 9(4) using 4-((tert-butyl(diphenyl)silyl)oxy)cyclohexanecarbonitrile as obtained in Reference 2, instead of tert-butyl 4-((tert-butyl(diphenyl)silyl)oxy)cyclohexanecarboxylate as used in the step of Example 9(2), 53.7 mg of 1-((2-(trimethylsilyl)ethoxy)methyl)-1H-pyrazol-3-amine, 29.2 mg of 9,9-dimethyl-4,5-bis(diphenylphosphino)xanthene, 26.1 mg of tris(dibenzylideneacetone)dipalladium(0)-chloroform complex, 89.2 mg of potassium phosphate and 3 ml of 1,4-dioxane was stirred at 100° C. overnight, followed by cooling down to room temperature. An insoluble matter was filtered off using Celite and washed with ethyl acetate. The resulting ethyl acetate solution was washed with water, dried over anhydrous sodium sulfate, and filtered. The filtrate was concentrated in vacuo. The resulting residue was purified by a silica gel column chromatography (eluent: hexane/ethyl acetate=20/1-3/2) to give the title compound as a pale yellow oil.

(2) Synthesis of trans-4-(3-chloro-2-fluorophenoxy)-1-((6-(1H-pyrazol-3-ylamino)pyridin-2-yl)methyl)cyclohexanecarbonitrile

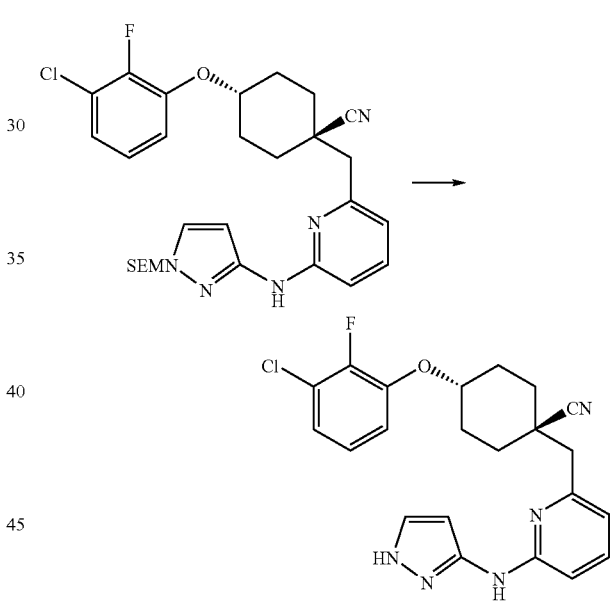

A solution of 29.6 mg of trans-4-(3-chloro-2-fluorophenoxy)-1-((6-((1-((2-(trimethylsilyl)ethoxy)methyl)-1H-pyrazol-3-yl)amino)pyridin-2-yl)methyl)cyclohexanecarbonitrile in 1 ml of trifluoroacetic acid and 0.1 ml of water was stirred at room temperature for 2 hours. After adding 2 M sodium hydroxide to the reaction mixture, the mixture was extracted with ethyl acetate. The resulting ethyl acetate solution was dried over anhydrous magnesium sulfate, and filtered. The filtrate was concentrated in vacuo. The obtained residue was purified by a preparative thin-layer chromatography (Kieselgel™60F$_{254}$, Art5744 (Merck), chloroform/methanol=10/1) to give the title compound as a pale yellow solid.

$^1$H-NMR(CDCl$_3$)δ: 1.81-2.01 (6H,m),2.02-2.15(2H,m),2.99(2H,s),4.58(1H,s),6.11 (1H,s),6.78(1H,d,J=7.4 Hz),6.85-6.93(2H,m),6.94-7.03(2H,m),7.30(1H,brs),7.47(1H,s),7.51(1H,t,J=7.8 Hz).

mass:426,428(M+1)$^+$

Example 17

Synthesis of 6-((trans-4-(3-chloro-2-fluorophenoxy)-1-(2H-tetrazol-5-yl)cyclohexyl)methyl)-N-1H-pyrazol-3-ylpyridin-2-amine trifluoroacetate

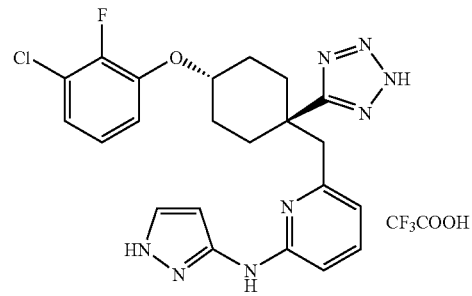

(1) Synthesis of 6-((trans-4-(3-chloro-2-fluorophenoxy)-1-(2H-tetrazol-5-yl)cyclohexyl)methyl)-N-(1-((2-(trimethylsilyl)ethoxy)methyl)-1H-pyrazol-3-yl)pyridin-2-amine

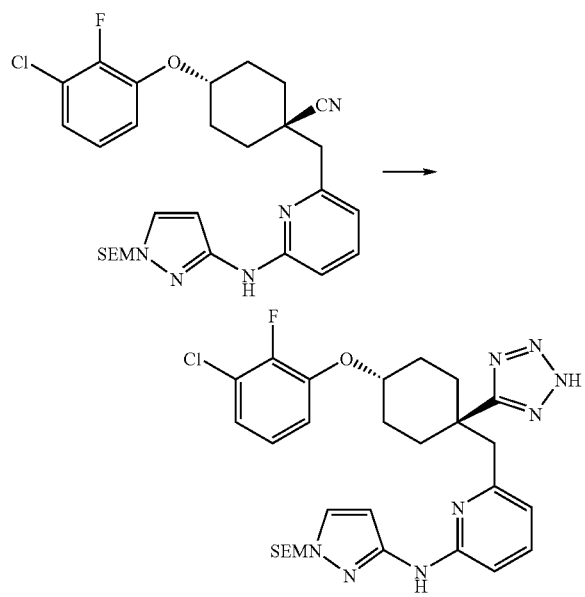

A mixture of 34.2 mg of trans-4-(3-chloro-2-fluorophenoxy)-1-((6-((1-((2-(trimethylsilyl)ethoxy)methyl)-1H-pyrazol-3-yl)amino)pyridin-2-yl)methyl)cyclohexanecarbonitrile as obtained in the step of Example 16(1), 40.0 mg of sodium azide, 84.7 mg of triethylamine hydrochloride and 2 ml of toluene was stirred at 100° C. overnight, followed by cooling down to room temperature. After adding 1 M hydrochloric acid to the reaction mixture, the mixture was extracted with ethyl acetate. The resulting ethyl acetate solution was washed with brine, dried over anhydrous magnesium sulfate, and filtered. The filtrate was concentrated in vacuo. The obtained residue was purified by a preparative thin-layer chromatography (Kieselgel™60F$_{254}$, Art5744 (Merck), chloroform/methanol=10/1) to give the title compound as a pale yellow oil.

(2) Synthesis of 6-((trans-4-(3-chloro-2-fluorophenoxy)-1-(2H-tetrazol-5-yl)cyclohexyl)methyl)-N-1H-pyrazol-3-ylpyridin-2-amine trifluoroacetate

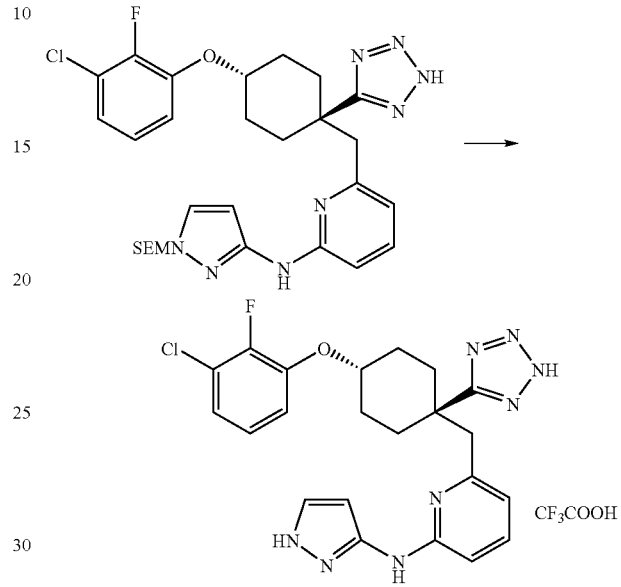

A solution of 7.8 mg of 6-((trans-4-(3-chloro-2-fluorophenoxy)-1-(2H-tetrazol-5-yl)cyclohexyl)methyl)-N-(1-((2-(trimethylsilyl)ethoxy)methyl)-1H-pyrazol-3-yl)pyridin-2-amine in 2 ml of trifluoroacetic acid and 0.2 ml of water was stirred at room temperature overnight, followed by concentrated in vacuo. The resulting residue was purified by a reversed phase preparative liquid chromatography, followed by concentrating the obtained fraction in vacuo to give the title compound as a pale yellow solid.

$^1$H-NMR(CD$_3$OD)δ: 1.49-1.62(2H,m), 1.99-2.10(2H,m), 2.23-2.40(4H,m),3.27-3.33(2H,m),4.50-4.55(1H,m),6.10 (1H,d,J=2.2 Hz),6.70(1H,d,J=7.2 Hz),6.99-7.14(4H,m),7.73 (1H,d,J=2.2 Hz),7.92(1H,dd,J=8.8,7.2 Hz).

mass:469,471(M+1)$^+$

Example 18

Synthesis of trans-4-(3-chloro-2-fluorophenoxy)-N-methoxy-1-((6-(1,3-thiazol-2-ylamino)pyridin-2-yl)methyl)cyclohexanecarboxamide

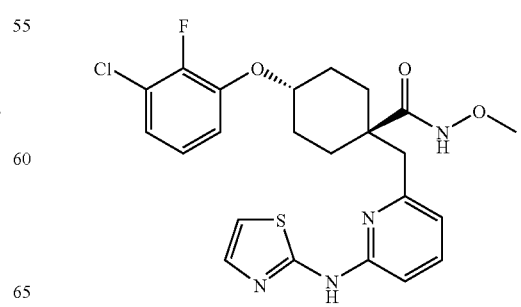

The title compound was obtained as a pale yellow solid in the same manner as in Example 8 using O-methylhydroxylamine hydrochloride, instead of ammonium chloride as used in Example 8.

$^1$H-NMR(CDCl$_3$)δ: 1.80-2.15(8H,m),3.07(2H,s),3.64 (3H,s),4.46(1H,brs),6.60(1H,s),6.70-7.03(5H,m),7.31 (1H,s),7.47(1H,t,J=7.6 Hz),9.39(1H,brs).

mass:491,493(M+1)$^+$

Example 19

Synthesis of N-(trans-4-(3-chloro-2-fluorophenoxy)-1-((6-(1,3-thiazol-2-ylamino)pyridin-2-yl)methyl)cyclohexyl)acetamide

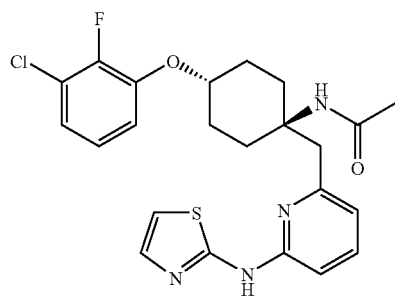

(1) Synthesis of 6-((trans-1-amino-4-(3-chloro-2-fluorophenoxy)cyclohexyl)methyl)-N-1,3-thiazol-2-ylpyridin-2-amine

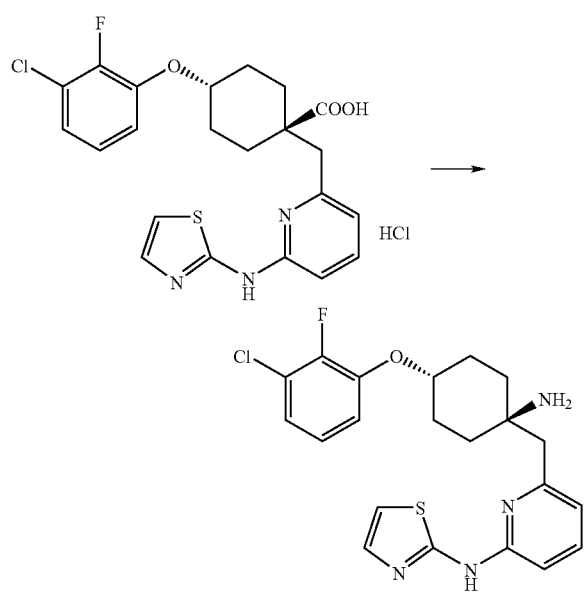

To a suspension of 99.7 mg of trans-4-(3-chloro-2-fluorophenoxy)-1-((6-(1,3-thiazol-2-ylamino)pyridin-2-yl)methyl)cyclohexanecarboxylic acid hydrochloride as obtained in Example 1 in 5 ml of 1,4-dioxane were successively added 0.084 ml of triethylamine and 0.052 ml of diphenylphosphorylazide at room temperature, followed by stirring the reaction mixture at room temperature for 1 hour. 0.056 ml of triethylamine and 0.034 ml of diphenylphosphorylazide were added to the reaction mixture at room temperature, followed by stirring the reaction mixture at room temperature for 1 hour, at 50° C. for 1 hour and at 100° C. overnight. After cooling the reaction mixture to room temperature, 2 ml of 2 M hydrochloric acid was added to the reaction mixture, followed by stirring the reaction mixture at 70° C. for 3 hours. After cooling the reaction mixture to room temperature, the reaction mixture was neutralized with 1 M sodium hydroxide followed by extracted with ethyl acetate. The resulting ethyl acetate solution was dried over anhydrous magnesium sulfate, and filtered. The filtrate was concentrated in vacuo. The resulting residue was purified by a reversed phase preparative liquid chromatography. The obtained fraction was concentrated in vacuo, basified with saturated sodium bicarbonate, and extracted with ethyl acetate. The resulting ethyl acetate solution was dried over anhydrous magnesium sulfate, and filtered. The filtrate was concentrated in vacuo to give the title compound as a pale yellow oil.

(2) Synthesis of N-(trans-4-(3-chloro-2-fluorophenoxy)-1-((6-(1,3-thiazol-2-ylamino)pyridin-2-yl)methyl)cyclohexyl)acetamide

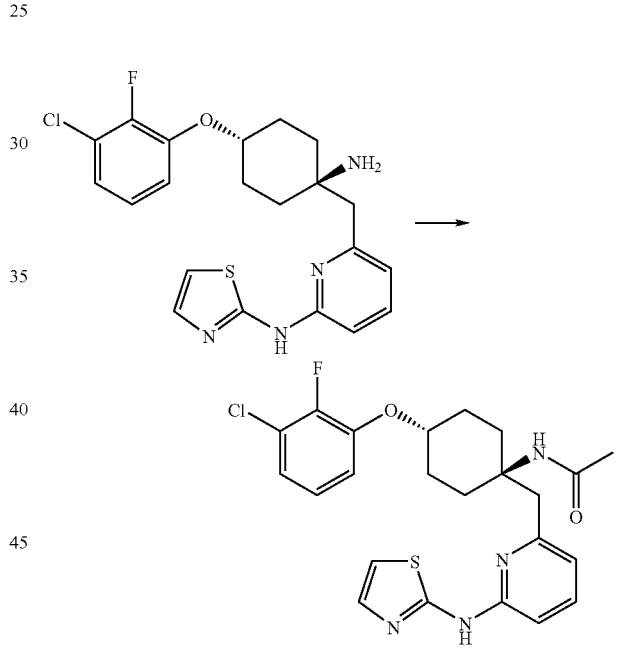

To a solution of 26 mg of 6-((trans-1-amino-4-(3-chloro-2-fluorophenoxy)cyclohexyl)methyl)-N-1,3-thiazol-2-ylpyridin-2-amine in 2 ml of pyridine was added 0.0068 ml of acetic anhydride at room temperature, followed by stirring the reaction mixture at room temperature for 1 hour. After concentrating the reaction mixture in vacuo, the resulting residue was diluted with ethyl acetate. The resulting ethyl acetate solution was washed with water, dried over anhydrous magnesium sulfate, and filtered. The filtrate was concentrated in vacuo. The obtained residue was purified by a preparative thin-layer chromatography (Kieselgel™60F$_{254}$, Art5744 (Merck), chloroform/methanol=10/1) to give the title compound as a pale yellow solid.

$^1$H-NMR(CDCl$_3$)δ: 1.84(3H,s),1.80-1.98(2H,m),2.31-2.49(2H,m),3.26(2H,s),4.45(1H,brs),5.92(1H,s),6.75-7.01 (6H,m),7.48(1H,d,J=2.8 Hz),7.56(1H,t,J=7.6 Hz).

mass:475,477(M+1)$^+$

Example 20

Synthesis of 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazol-2(3H)-one

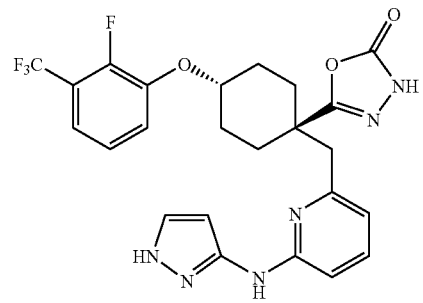

(1) Synthesis of trans-1-((6-((1-tert-butyl-1H-pyrazol-5-yl)amino)pyridin-2-yl)methyl)-4-(2-fluoro-3-(trifluoromethyl)phenoxy)cyclohexanecarboxylic acid trifluoroacetate

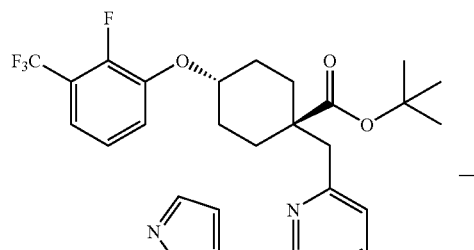

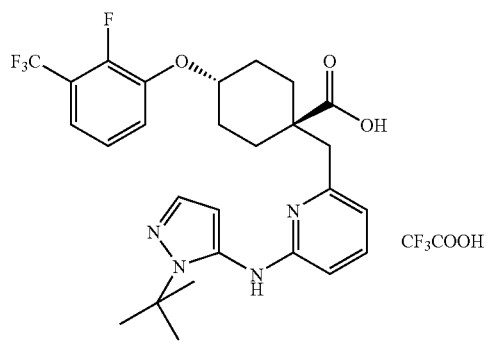

To a solution of 2.51 g of tert-butyl trans-1-((6-((1-tert-butyl-1H-pyrazol-5-yl)amino)pyridin-2-yl)methyl)-4-(2-fluoro-3-(trifluoromethyl)phenoxy)cyclohexanecarboxylate as obtained in the step of Example 9(5) in 39 ml of chloroform was added 19 ml of trifluoroacetic acid at 0° C., followed by stirring the reaction mixture at room temperature overnight. The resulting solution was concentrated in vacuo to give the title compound as yellow oil.

(2) Synthesis of tert-butyl 2-((trans-1-((6-((1-tert-butyl-1H-pyrazol-5-yl)amino)pyridin-2-yl)methyl)-4-(2-fluoro-3-trifluoromethyl)phenoxy)cyclohexyl)carbonyl)hydrazinecarboxylate

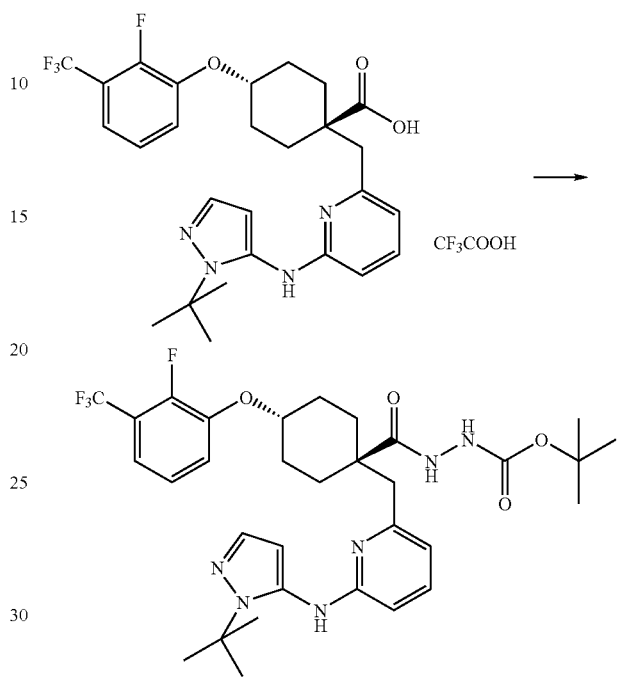

To a solution of 3.2 g of trans-1-((6-((1-tert-butyl-1H-pyrazol-5-yl)amino)pyridin-2-yl)methyl)-4-(2-fluoro-3-(trifluoromethyl)phenoxy)cyclohexanecarboxylic acid trifluoroacetate in 14.1 ml of chloroform were successively added 5.62 g of tert-butyl carbazate, 3.27 g of 1-hydroxybenzotriazole hydrate and 4.13 g of 1-(3-dimethylaminopropyl)-3-ethylcarbodiimide hydrochloride at room temperature, followed by stirring at room temperature for 8 hours. After adding ethyl acetate to the reaction mixture, the organic layer was successively washed with water and brine, dried over anhydrous magnesium sulfate, filtered, and concentrated in vacuo. The resulting residue was purified by a silica gel column chromatography (eluent: hexane to hexane/ethyl acetate=1/4) to give the title compound as a pale yellow solid.

(3) Synthesis of trans-1-((6-((1-tert-butyl-1H-pyrazol-5-yl)amino)pyridin-2-yl)methyl)-4-(2-fluoro-3-(trifluoromethyl)phenoxy)cyclohexanecarbohydrazide

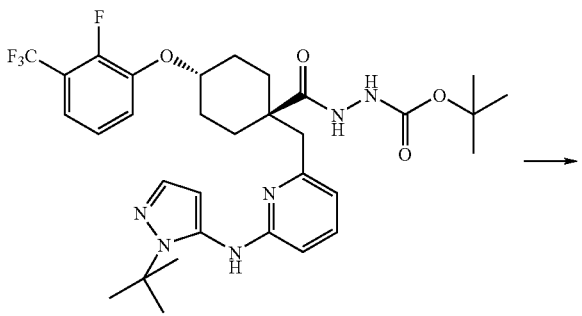

-continued

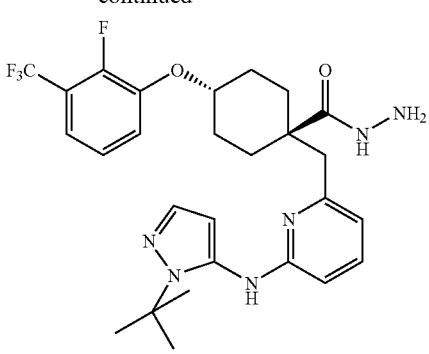

To a solution of 2.93 g of tert-butyl 2-((trans-1-((6-(((1-tert-butyl-1H-pyrazol-5-yl)amino)pyridin-2-yl)methyl)-4-(2-fluoro-3-(trifluoromethyl)phenoxy)cyclohexyl)carbonyl)hydrazinecarboxylate in 30 ml of chloroform was added 15 ml of trifluoroacetic acid at room temperature, followed by stirring at room temperature for 1 hour. After concentrating the reaction mixture in vacuo, the resulting residue was dissolved in chloroform. The chloroform solution was successively washed with saturated sodium bicarbonate and brine, dried over anhydrous magnesium sulfate, filtered, and concentrated in vacuo. The resulting residue was purified by a silica gel column chromatography (eluent: chloroform to chloroform/methanol=10/1) to give the title compound as a pale yellow solid.

(4) Synthesis of 5-(trans-1-((6-(((1-tert-butyl-1H-pyrazol-5-yl)amino)pyridin-2-yl)methyl)-4-(2-fluoro-3-(trifluoromethyl)phenoxy)cyclohexyl)-1,3,4-oxadiazol-2(3H)-one

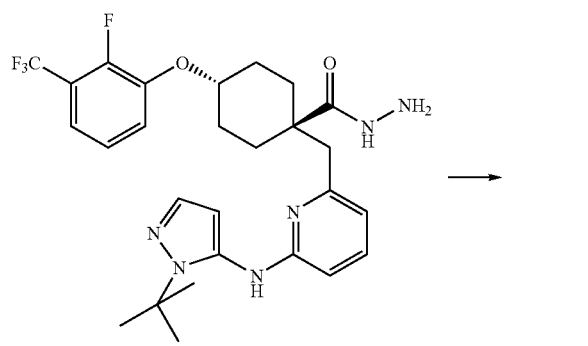

To a solution of 1.9 g of trans-1-((6-(((1-tert-butyl-1H-pyrazol-5-yl)amino)pyridin-2-yl)methyl)-4-(2-fluoro-3-trifluoromethyl)phenoxy)cyclohexanecarbohydrazide in 35 ml of tetrahydrofuran were added 3.05 ml of N,N-diisopropylethylamine and 1.70 g of 1,1'-carbonyldiimidazole at room temperature. The reaction mixture was stirred at room temperature for 1.5 hours, followed by concentrating the resulting solution in vacuo. The resulting residue was purified by a silica gel column chromatography (eluent: chloroform to chloroform/methanol=10/1) to give the title compound as a pale yellow solid.

(5) Synthesis of 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazol-2(3H)-one

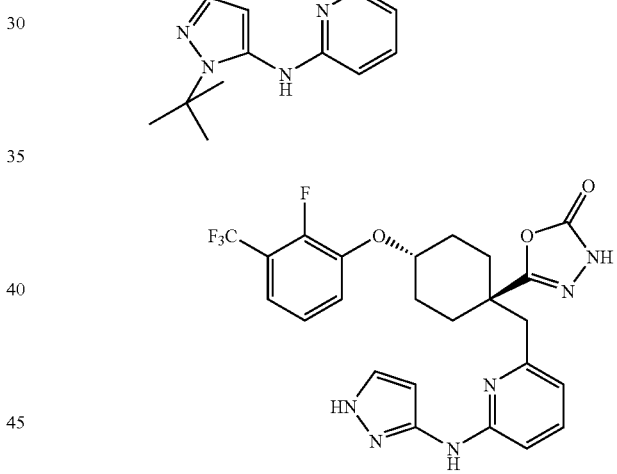

A solution of 2.11 g of 5-(trans-1-((6-(((1-tert-butyl-1H-pyrazol-5-yl)amino)pyridin-2-yl)methyl)-4-(2-fluoro-3-(trifluoromethyl)phenoxy)cyclohexyl)-1,3,4-oxadiazol-2(3H)-one in 37 ml of formic acid was stirring at 95° C. for 1.5 hours. After concentrating the reaction mixture in vacuo, the resulting residue was basified with saturated sodium bicarbonate and extracted with chloroform. The chloroform solution was successively washed with water and brine, dried over anhydrous magnesium sulfate, filtered, and concentrated in vacuo. The resulting residue was purified by a silica gel column chromatography (eluent: chloroform to chloroform/methanol=4/1) to give the title compound as a white solid.

$^{1}$H-NMR(CDCl$_{3}$)δ: 1.63-1.80(2H,m), 1.89-2.07(6H,m), 3.02(2H,s),4.47-4.53(1H,m),6.23(1H,brs),6.50(1H,d,J=8.0 Hz),6.61(1H,d,J=7.2 Hz),7.06(1H,brs),7.10-7.22(3H,m), 7.35-7.42(2H,m).

mass:519(M+1)$^{+}$

Example 21

Synthesis of 6-((trans-4-(2-fluoro-3-(trifluoromethyl)phenoxy)-1-(5-imino-4,5-dihydro-1,3,4-oxadiazol-2-yl)cyclohexyl)methyl)-N-1H-pyrazol-3-ylpyridin-2-amine trifluoroacetate

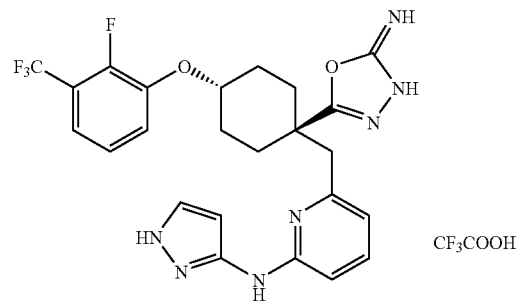

(1) Synthesis of trans-4-(2-fluoro-3-(trifluoromethyl)phenoxy)-1-((6-(1H-pyrazol-3-ylamino)pyridin-2-yl)methyl)cyclohexanecarbohydrazide

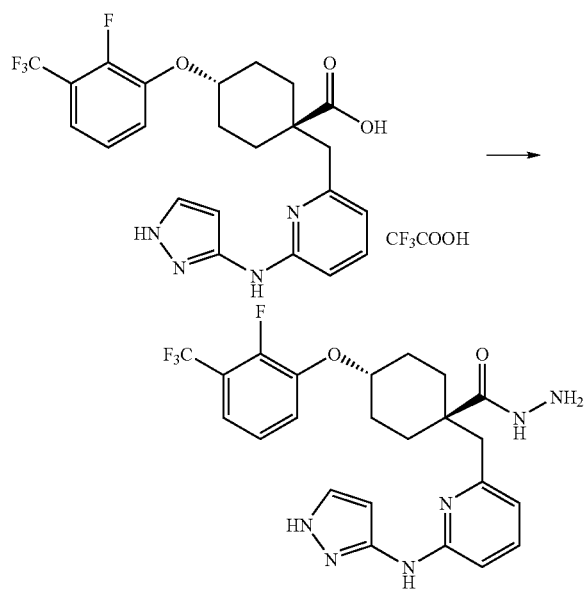

To a solution of 33.8 mg of trans-4-(2-fluoro-3-(trifluoromethyl)phenoxy)-1-((6-(1H -pyrazol-3-ylamino)pyridin-2-yl)methyl)cyclohexanecarboxylic acid trifluoroacetate as obtained in Example 9 in 1.5 ml of dimethylsulfoxide were successively added 59.9 mg of hydrazine dihydrochloride, 0.2 ml of N,N-diisopropylethylamine, 26.2 mg of 1-hydroxybenzotriazole hydrate and 32.9 mg of 1-(3-dimethylaminopropyl)-3-ethylcarbodiimide hydrochloride at room temperature, followed by stirring at room temperature overnight. After adding ethyl acetate to the reaction mixture, the organic layer was successively washed with 2 M sodium hydroxide and brine, dried over anhydrous magnesium sulfate, filtered, and concentrated in vacuo. The obtained residue was purified by a preparative thin-layer chromatography (Kieselgel™ 60F254, Art5744 (Merck), chloroform/methanol=10/1) to give the title compound as a pale yellow oil.

(2) Synthesis of 6-((trans-4-(2-fluoro-3-(trifluoromethyl)phenoxy)-1-(5-imino-4,5-dihydro-1,3,4-oxadiazol-2-yl)cyclohexyl)methyl)-N-1H-pyrazol-3-ylpyridin-2-amine trifluoroacetate

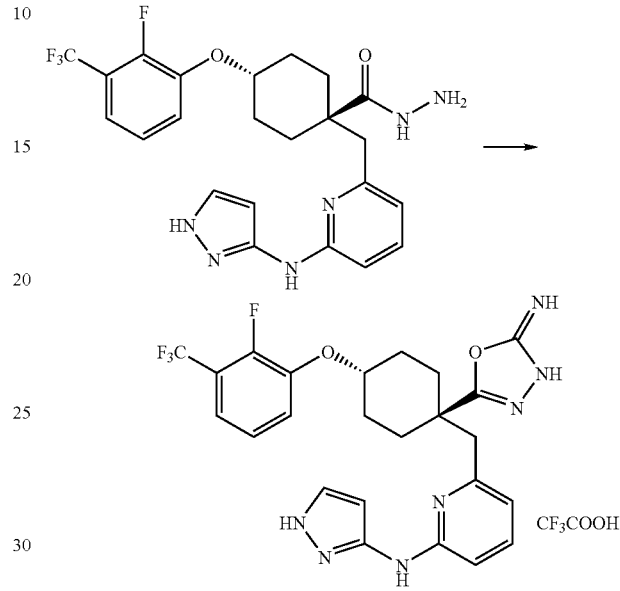

To a solution of 12.1 mg of trans-4-(2-fluoro-3-(trifluoromethyl)phenoxy)-1-((6-(1H -pyrazol-3-ylamino)pyridin-2-yl)methyl)cyclohexanecarbohydrazide in 1 ml of methanol was added 3.9 mg of cyanogen bromide at room temperature, followed by stirring the reaction mixture at 80° C. for 5 hours. The reaction mixture was concentrated in vacuo. The resulting residue was purified by a reversed phase preparative liquid chromatography, followed by concentrating the obtained fraction in vacuo to give the title compound as a pale yellow solid.

$^1$H-NMR(CDCl$_3$)δ: 1.95-2.28(8H,m),3.20(2H,s),4.49-4.60(1H,m),6.09-6.16(1H,m),6.81(1H,d,J=6.7 Hz),7.12-7.24(4H,m),7.38-7.51(1H,m),7.73-7.87(1H,m).
mass:518(M+1)$^+$

Example 22

Synthesis of 6-((trans-4-(2-fluoro-3-(trifluoromethyl)phenoxy)-1-(1,3,4-oxadiazol-2-yl)cyclohexyl)methyl)-N-1H-pyrazol-3-ylpyridin-2-amine

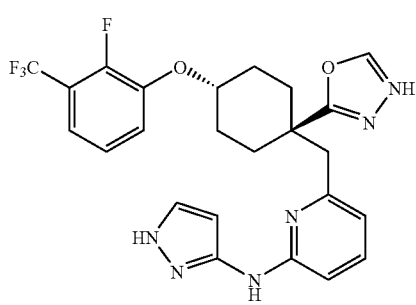

A mixture of 15.1 mg of trans-4-(2-fluoro-3-(trifluoromethyl)phenoxy)-1-((6-(1H -pyrazol-3-ylamino)pyridin-2-yl)methyl)cyclohexanecarbohydrazide as obtained in the step of Example 21(1) and 1.5 ml of triethylorthoformate was stirred at 150° C. for 5 hours, followed by concentrating the reaction mixture in vacuo. The obtained residue was purified by a preparative thin-layer chromatography (Kieselgel™60F$_{254}$, Art5744 (Merck), chloroform/methanol=20/1) to give the title compound as a pale yellow solid.

$^1$H-NMR(CDCl$_3$)δ: 1.90-2.30(8H,m),3.14(2H,s),4.45-4.54(1H,m),5.94(1H,brs),6.50(1H,d,J=7.2 Hz),6.77-6.90(1H,m),7.09-7.23(4H,m),7.38-7.48(2H,m),8.33(1H,s).

mass:503(M+1)$^+$

Example 23

Synthesis of 5-(trans-4-(3-chloro-2-fluorophenoxy)-1-((6-(1H-pyrazol-3-ylamino)pyridin-2-yl)methyl)cyclohexyl)-1,3,4-oxadiazol-2(3H)-one

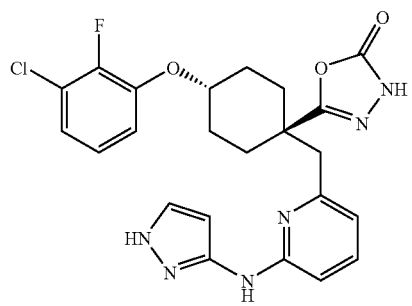

(1) Synthesis of trans-1-((6-((1-tert-butyl-1H-pyrazol-5-yl)amino)pyridin-2-yl)methyl)-4-(3-chloro-2-fluorophenoxy)cyclohexanecarbohydrazide

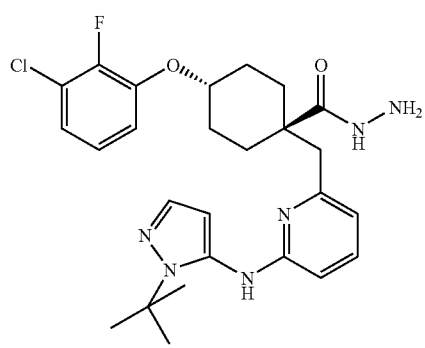

The title compound was obtained as a pale yellow oil in the same manner as in the steps of Example 9(4),(5), and Example 20(1) to 20(3) using 3-chloro-2-fluorophenol instead of 2-fluoro-3-(trifluoromethyl)phenol as used in Example 9(4).

(2) Synthesis of 5-(trans-4-(3-chloro-2-fluorophenoxy)-1-((6-(1H-pyrazol-3-ylamino)pyridin-2-yl)methyl)cyclohexyl)-1,3,4-oxadiazol-2(3H)-one

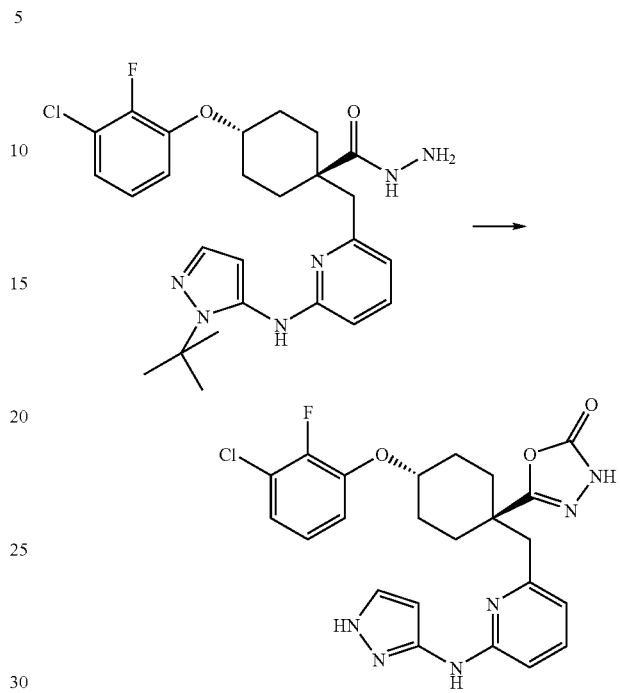

The title compound was obtained as a white solid in the same manner as in the steps of Example 20(4) and 20(5) using trans-1-((6-((1-tert-butyl-1H-pyrazol-5-yl)amino)pyridin-2-yl)methyl)-4-(3-chloro-2-fluorophenoxy)cyclohexanecarbohydrazide instead of trans-1-((6-((1-tert-butyl-1H-pyrazol-5-yl)amino)pyridin-2-yl)methyl)-4-(2-fluoro-3-(trifluoromethyl)phenoxy)cyclohexanecarbohydrazide as used in Example 20(4).

$^1$H-NMR(DMSO-d$_6$)δ: 1.65-2.00(8H,m),2.97(2H,s),4.63(1H,brs),6.30-6.45(2H,m),6.95-7.30(4H,m),7.46(1H,t,J=8.0 Hz),7.48-7.56(1H,m),9.15(1H,s),12.02(1H,s),12.07(1H,brs).

mass:485,487(M+1)$^+$

Example 24

Synthesis of 5-(trans-4-(3-chloro-2-fluorophenoxy)-1-((6-(1H-pyrazol-3-ylamino)pyridin-2-yl)methyl)cyclohexyl)-1,3,4-oxadiazole-2(3H)-thione

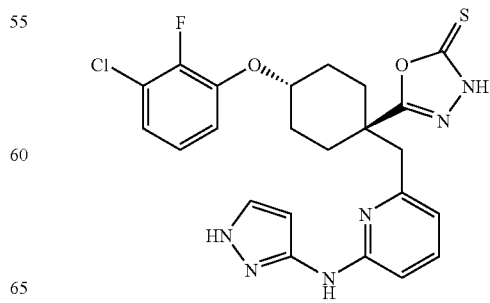

(1) Synthesis of 5-(trans-1-((6-((1-tert-butyl-1H-pyrazol-5-yl)amino)pyridin-2-yl)methyl)-4-(3-chloro-2-fluorophenoxy)cyclohexyl)-1,3,4-oxadiazole-2(3H)-thione

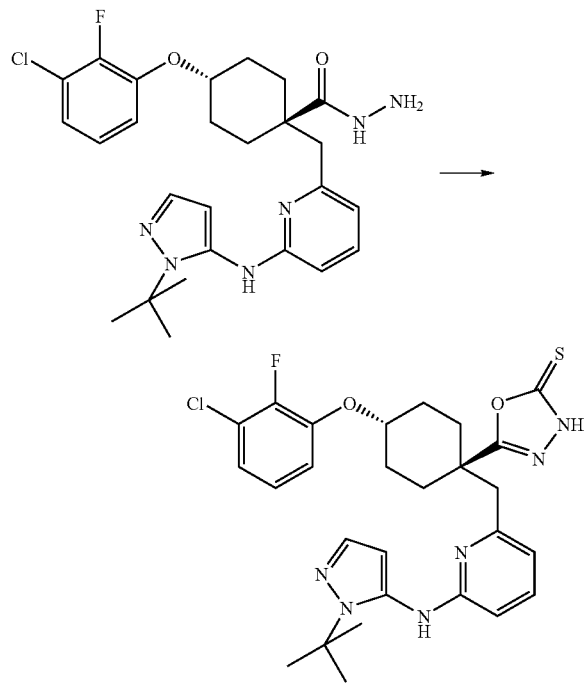

To a solution of 97 mg of trans-1-((6-((1-tert-butyl-1H-pyrazol-5-yl)amino)pyridin-2-yl)methyl)-4-(3-chloro-2-fluorophenoxy)cyclohexanecarbohydrazide as obtained in the step of Example 23(1) in 3 ml of ethanol were added 0.078 ml of carbon disulfide and 0.432 ml of an ethanol solution containing 0.87 M potassium hydroxide at room temperature. The reaction mixture was stirred at 80° C. for 3 hours, acidified with 2 M hydrochloric acid, and extracted with ethyl acetate. The ethyl acetate solution was dried over anhydrous magnesium sulfate, filtered, and concentrated in vacuo. The resulting residue was purified by a silica gel column chromatography (eluent: hexane to hexane/ethyl acetate=2/3) to give the title compound as a pale yellow oil.

(2) Synthesis of 5-(trans-4-(3-chloro-2-fluorophenoxy)-1-((6-(1H-pyrazol-3-ylamino)pyridin-2-yl)methyl)cyclohexyl)-1,3,4-oxadiazole-2(3H)-thione

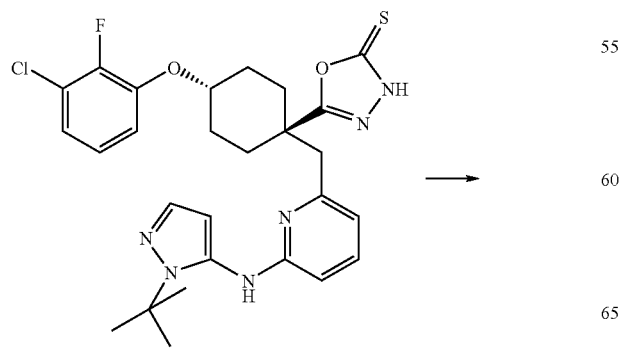

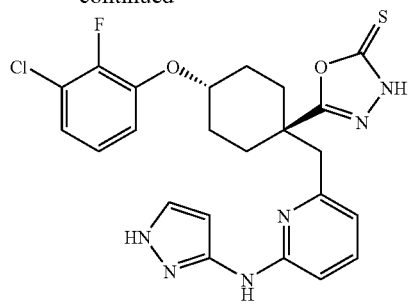

The title compound was obtained as a pale yellow solid in the same manner as in the step of Example 20(5) using 5-(trans-1-((6-((1-tert-butyl-1H-pyrazol-5-yl)amino)pyridin-2-yl)methyl)-4-(3-chloro-2-fluorophenoxy)cyclohexyl)-1,3,4-oxadiazole-2(3H)-thione instead of 5-(trans-1-((6-((1-tert-butyl-1H-pyrazol-5-yl)amino)pyridin-2-yl)methyl)-4-(2-fluoro-3-(trifluoromethyl)phenoxy)cyclohexyl)-1,3,4-oxadiazol-2(3H)-one as used in Example 20(5).

$^1$H-NMR(DMSO-d$_6$)δ: 1.61-1.74(2H,m),1.85-2.01(6H,m),2.96(2H,s),4.56(1H,brs),6.24(1H,s),6.33(1H,d,J=7.2 Hz),6.90-7.00(1H,m),7.09-7.24(3H,m),7.37(1H,t,J=7.6 Hz), 7.48(1H,s),9.01 (1H,brs).
mass:501,503(M+1)$^+$ Example 25

Synthesis of 6-((trans-4-(3-chloro-2-fluorophenoxy)-1-(5-methyl-1,3,4-oxadiazol-2-yl)cyclohexyl)methyl)-N-1H-pyrazol-3-ylpyridin-2-amine

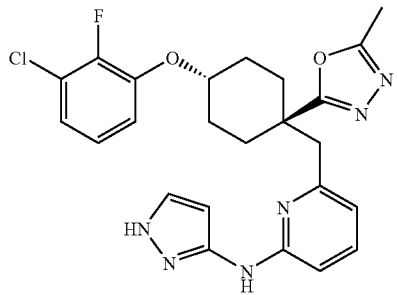

(1) Synthesis of N-(1-tert-butyl-1H-pyrazol-5-yl)-6-((trans-4-(3-chloro-2-fluorophenoxy)-1-(5-methyl-1,3,4-oxadiazol-2-yl)cyclohexyl)methyl)pyridin-2-amine

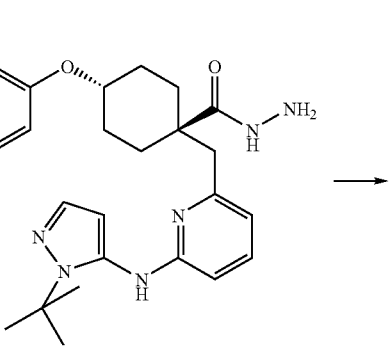

-continued

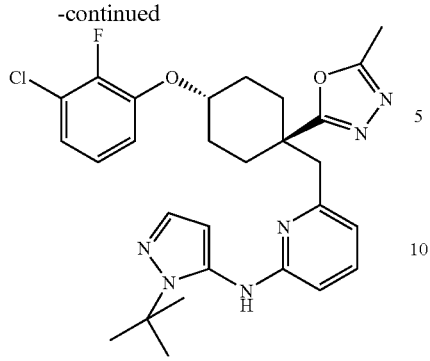

The title compound was obtained as a pale yellow oil in the same manner as in Example 22 using trans-1-((6-((1-tert-butyl-1H-pyrazol-5-yl)amino)pyridin-2-yl)methyl)-4-(3-chloro-2-fluorophenoxy)cyclohexanecarbohydrazide as obtained in the step of Example 23(1) and triethylorthoacetate, instead of both trans-4-(2-fluoro-3-(trifluoromethyl)phenoxy)-1-((6-(1H -pyrazol-3-ylamino)pyridin-2-yl)methyl)cyclohexanecarbohydrazide and triethylorthoformate as used in Example 22.

(2) Synthesis of 6-((trans-4-(3-chloro-2-fluorophenoxy)-1-(5-methyl-1,3,4-oxadiazol-2-yl)cyclohexyl)methyl)-N-1H-pyrazol-3-ylpyridin-2-amine

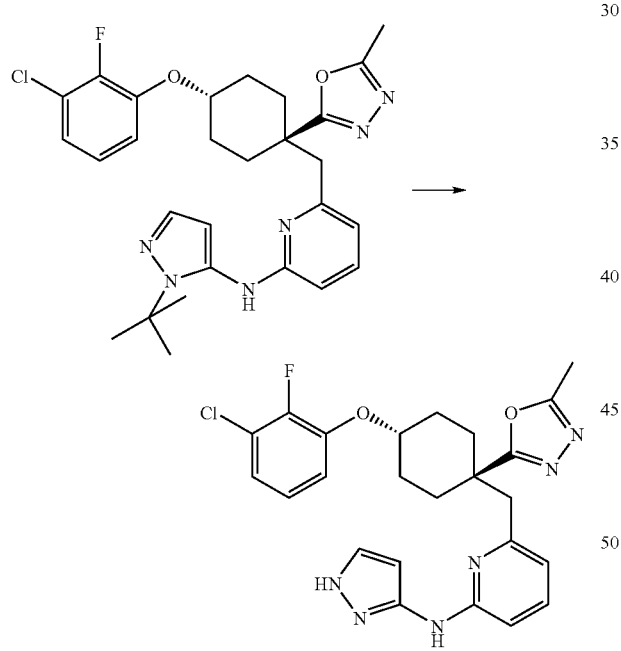

The title compound was obtained as a pale yellow solid in the same manner as in the step of Example 20(5) using N-(1-tert-butyl-1 H-pyrazol-5-yl)-6-((trans-4-(3-chloro-2-fluorophenoxy)-1-(5-methyl-1,3,4-oxadiazol-2-yl)cyclohexyl)methyl)pyridin-2-amine instead of 5-(trans-1-((6-((1-tert-butyl-1H-pyrazol-5-yl)amino)pyridin-2-yl)methyl)-4-(2-fluoro-3-(trifluoromethyl)phenoxy)cyclohexyl)-1,3,4-oxadiazol-2(3H)-one as used in Example 20(5).
$^1$H-NMR(CDCl$_3$)δ: 1.58-1.76(2H,m),1.97-2.27(6H,m), 2.40(3H,s),3.08(2H,s),4.45(1H,brs),5.90(1H,s),6.48(1H,d, J=6.8 Hz),6.69(1H,d,J=7.6 Hz), 6.85-7.15 (4H,m),7.37(1H, t,J=7.6 Hz),7.42(1H,s).
mass:483,485(M+1)$^+$

Example 26

Synthesis of 5-(trans-4-(3-chloro-2-fluorophenoxy)-1-((6-(1H-pyrazol-3-ylamino)pyridin-2-yl)methyl)cyclohexyl)-3-methyl-1,3,4-oxadiazol-2(3H)-one

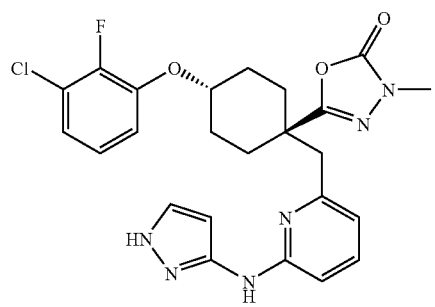

The title compound was obtained as a pale yellow solid in the same manner as in Example 23 using tert-butyl 1-methylhydrazinecarboxylate instead of tert-butyl carbazate as used in Example 23.
$^1$H-NMR(CDCl$_3$)δ: 1.58-1.75(2H,m),1.96-2.05(6H,m), 2.99(2H,s),3.20(3H,s),4.46(1H,brs),6.09(1H,s),6.55(1H,d, J=6.8 Hz),6.77(1H,d,J=8.0 Hz), 6.80-7.20(4H,m),7.42(1H,t, J=7.6 Hz),7.46(1H,s).
mass:499,501(M+1)$^+$

Example 27

Synthesis of 6-((trans-4-(2-fluoro-3-(trifluoromethyl)phenoxy)-1-(1,3,4-thiadiazol-2-yl)cyclohexyl)methyl)-N-1H-pyrazol-3-ylpyridin-2-amine

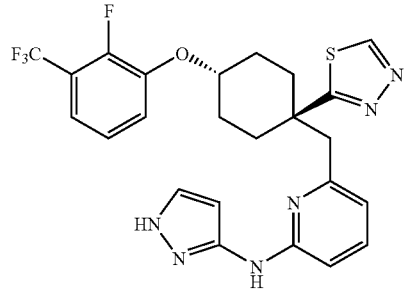

(1) Synthesis of trans-1-((6-((1-tert-butyl-1H-pyrazol-5-yl)amino)pyridin-2-yl)methyl)-4-(2-fluoro-3-(trifluoromethyl)phenoxy)-N'-formylcyclohexanecarbohydrazide

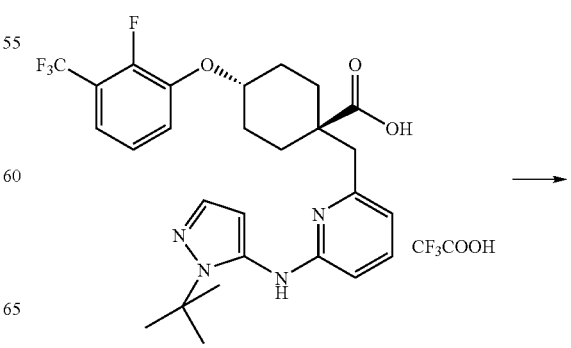

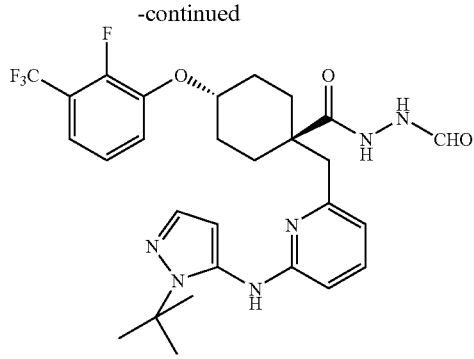

To a solution of 97 mg of trans-1-(((6-((1-tert-butyl-1H-pyrazol-5-yl)amino)pyridin-2-yl)methyl)-4-(2-fluoro-3-(trifluoromethyl)phenoxy)cyclohexanecarboxylic acid trifluoroacetate as obtained in the step of Example 20(1) in 5 ml of chloroform were added 45 mg of formic hydrazide and 86 mg of 1-(3-dimethylaminopropyl)-3-ethylcarbodiimide hydrochloride at room temperature, followed by stirring at room temperature overnight. After adding ethyl acetate to the reaction mixture, the organic layer was washed with water, dried over anhydrous magnesium sulfate, filtered, and concentrated in vacuo. The resulting residue was purified by a silica gel column chromatography (eluent: hexane/ethyl acetate=4/1 to 1/4) to give the title compound as a pale yellow oil.

(2) Synthesis of N-(1-tert-butyl-1H-pyrazol-5-yl)-6-((trans-4-(2-fluoro-3-(trifluoromethyl)phenoxy)-1-(1,3,4-thiadiazol-2-yl)cyclohexyl)methyl)pyridin-2-amine

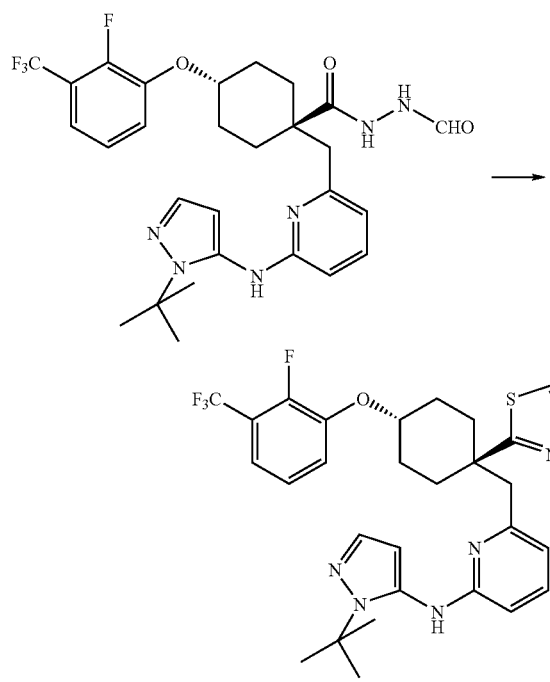

To a solution of 54.3 mg of trans-1-((6-((1-tert-butyl-1H-pyrazol-5-yl)amino)pyridin-2-yl)methyl)-4-(2-fluoro-3-(trifluoromethyl)phenoxy)-N'-formylcyclohexanecarbohydrazide in 4 ml of toluene was added 38.1 mg of Lawesson's reagent (2,4-bis(4-methoxyphenyl)-1,3-dithia-2,4-diphosphetane-2,4-disulfide) at room temperature. The reaction mixture was stirred at 110° C. for 1 hour, followed by concentrating the reaction mixture in vacuo. The obtained residue was purified by a preparative thin-layer chromatography (Kieselgel™60F$_{254}$, Art5744 (Merck), chloroform/methanol=10/1) to give the title compound as a pale yellow oil.

(3) Synthesis of 6-((trans-4-(2-fluoro-3-(trifluoromethyl)phenoxy)-1-(1,3,4-thiadiazol-2-yl)cyclohexyl)methyl)-N-1H-pyrazol-3-ylpyridin-2-amine

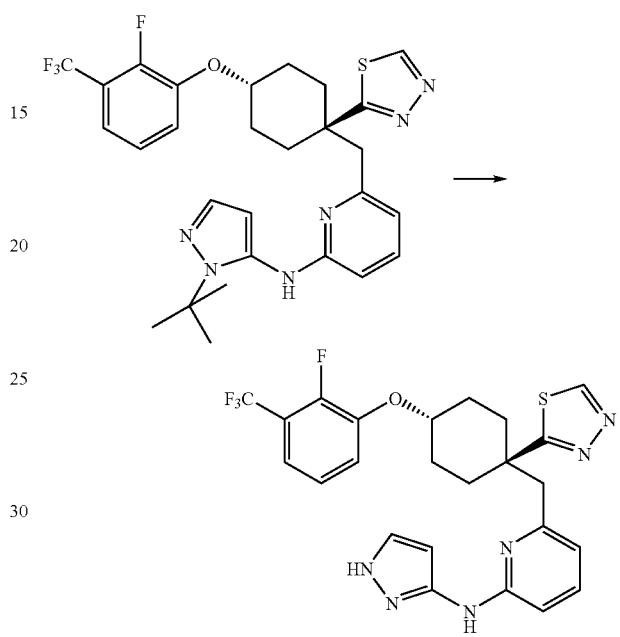

The title compound was obtained as a pale yellow solid in the same manner as in the step of Example 20(5) using N-(1-tert-butyl-1H-pyrazol-5-yl)-6-((trans-4-(2-fluoro-3-(trifluoromethyl)phenoxy)-1-(1,3,4-thiadiazol-2-yl)cyclohexyl)methyl)pyridin-2-amine instead of 5-(trans-1-((6-((1-tert-butyl-1H-pyrazol-5-yl)amino)pyridin-2-yl)methyl)-4-(2-fluoro-3-(trifluoromethyl)phenoxy)cyclohexyl)-1,3,4-oxadiazol-2(3H)-one as used in Example 20(5).

$^1$H-NMR(CDCl$_3$)δ: 1.66-1.77(2H,m),2.00-2.10(2H,m), 2.25-2.42(4H,m),3.14(2H,s),4.47(1H,brs),5.91 (1H,s),6.38 (1H,d,J=7.2 Hz),6.70(1H,d,J=8.0 Hz),7.00(1H,brs),7.09-7.20(3H,m),7.35(1H,t,J=7.6 Hz),7.42(1H,s),8.99(1H,s).
mass:519(M+1)$^+$ Example 28

Synthesis of 6-((trans-4-(2-fluoro-3-(trifluoromethyl)phenoxy)-1-(5-methyl-1,3,4-thiadiazol-2-yl)cyclohexyl)methyl)-N-1H-pyrazol-3-ylpyridin-2-amine

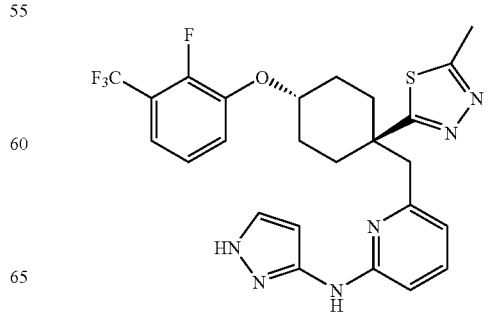

The title compound was obtained as a pale yellow solid in the same manner as in Example 27 using acetic hydrazide instead of formic hydrazide as used in the step of Example 27(1).

$^1$H-NMR(CDCl$_3$)δ: 1.65-1.77(2H,m),1.99-2.08(2H,m), 2.18-2.32(4H,m),2.61(3H,s),3.09(2H,s),4.47(1H,brs),5.83 (1H,s),6.46(1H,d,J=7.2 Hz),6.64(1H,d,J=8.0 Hz),7.09-7.20 (4H,m),7.35(1H,t,J=7.6 Hz),7.40(1H,s).

mass:533(M+1)$^+$

Example 29

Synthesis of 5-(trans-4-(3-chloro-2-fluorophenoxy)-1-((6-(1H-pyrazol-3-ylamino)pyrazin-2-yl)methyl)cyclohexyl)-1,3,4-oxadiazol-2(3H)-one

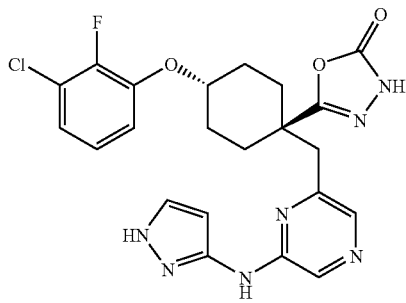

The title compound was obtained as a white solid in the same manner as in Example 20 using tert-butyl trans-1-((6-((1-tert-butyl-1H-pyrazol-5-yl)amino)pyrazin-2-yl)methyl)-4-(3-chloro-2-fluorophenoxy)cyclohexanecarboxylate as obtained in the step of Example 14(8).

$^1$H-NMR(DMSO-d$_6$)δ: 1.60-1.95(8H,m),2.92(2H,s),4.57 (1H,brs),6.38(1H,s),7.10-7.25(3H,m),7.52(1H,s),7.62(1H, s),8.27(1H,s),9.66(1H,s), 11.98(1H,s),12.16(1H,s).

mass:486,488(M+1)$^+$

Example 30

Synthesis of trans-4-((2,3-dichlorophenyl)thio)-1-((6-(1,3-thiazol-2-ylamino)pyridin-2-yl)methyl)cyclohexanecarboxylic acid trifluoroacetate

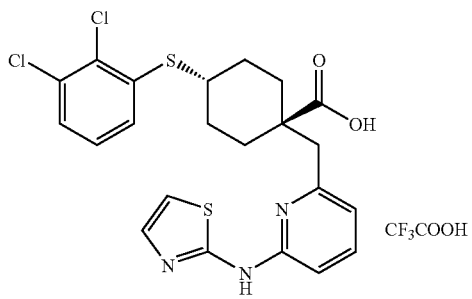

(1) Synthesis of tert-butyl trans-4-((2,3-dichlorophenyl)thio)-1-(((6-(((2Z)-3-(methoxymethyl)-1,3-thiazol-2(3H)-ylidene)amino)pyridin-2-yl)methyl)cyclohexanecarboxylate

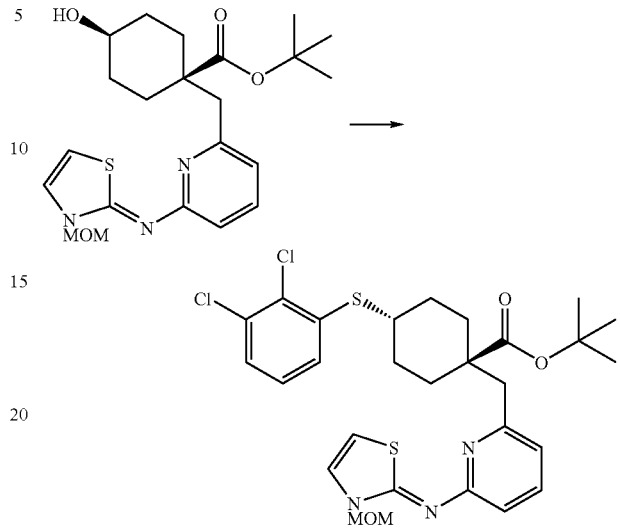

To a solution of 107.4 mg of tert-butyl cis-4-hydroxy-1-((6-(((2Z)-3-(methoxymethyl)-1,3-thiazol-2(3H)-ylidene) amino)pyridin-2-yl)methyl)cyclohexanecarboxylate as obtained in the step of Example 1(6) in 0.83 ml of tetrahydrofuran were added 0.070 ml of triethylamine and 0.029 ml of methanesulfonyl chloride at 0° C., followed by stirring the reaction mixture at room temperature for 30 minutes. The precipitate was filtered off and washed with tetrahydrofuran, and the filtrate was concentrated in vacuo. The obtained residue was purified by a silica gel column chromatography (eluent: hexane to hexane/ethyl acetate=4/1) to give tert-butyl cis-1-((6-(((2Z)-3-(methoxymethyl)-1,3-thiazol-2(3H)-ylidene)amino)pyridin-2-yl)methyl)-4-((methylsulfonyl)oxy)cyclohexanecarboxylate.

To a solution of 110 mg of tert-butyl cis-1-((6-(((2Z)-3-(methoxymethyl)-1,3-thiazol-2(3H)-ylidene)amino)pyridin-2-yl)methyl)-4-((methylsulfonyl)oxy)cyclohexanecarboxylate in 0.72 ml of N-methyl-2-pyrrolidinone were added 62.8 mg of potassium carbonate and 78.0 mg of 2,3-dichlorobenzenethiol at room temperature, followed by stirring the reaction mixture at 80° C. overnight. The reaction mixture was cooled to room temperature, and to the reaction mixture was added water and extracted with ethyl acetate. The ethyl acetate layer was washed with brine, dried over anhydrous magnesium sulfate, filtered, and concentrated in vacuo. The resulting residue was purified by a silica gel column chromatography (eluent: hexane to hexane/ethyl acetate=1/4) to give the title compound as a yellow oil.

(2) Synthesis of trans-4-((2,3-dichlorophenyl)thio)-1-((6-(1,3-thiazol-2-ylamino)pyridin-2-yl)methyl) cyclohexanecarboxylic acid trifluoroacetate

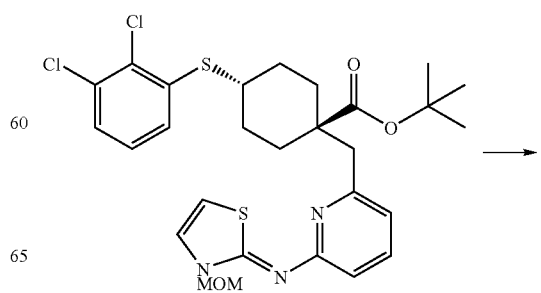

-continued

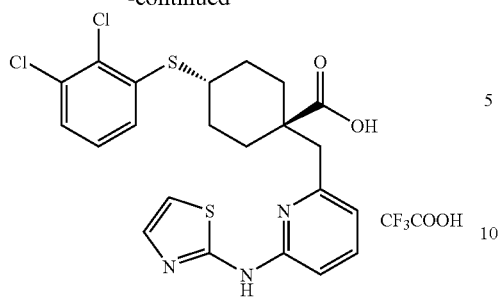

To a 39.0 mg of tert-butyl trans-4-((2,3-dichlorophenyl)thio)-1-((6-(((2Z)-3-(methoxymethyl)-1,3-thiazol-2(3H)-ylidene)amino)pyridin-2-yl)methyl)cyclohexanecarboxylate was added 1 ml of 4 M hydrogen chloride in 1,4-dioxane, followed by stirring the reaction mixture at 95° C. for 2.5 hours. After cooling the reaction mixture to room temperature, the reaction mixture was concentrated in vacuo. The resulting residue was purified by a reversed phase preparative liquid chromatography, followed by concentrating the obtained fraction in vacuo to give the title compound as a white solid.

$^1$H-NMR(DMSO-d$_6$)δ: 1.71-1.96(8H,m),3.00(2H,s),3.64 (1H,brs),6.74(1H,d,J=7.6 Hz),6.91(1H,d,J=8.0 Hz),7.03(1H, d,J=4.0 Hz),7.31(1H,t,J=8.0 Hz),7.40(1H,d,J=4.0 Hz),7.41-7.47(2H,m),7.60(1H,dd,J=8.0,7.6 Hz),11.40(1H,brs).

mass:494,496(M+1)$^+$

Example 31

Synthesis of trans-4-((2,3-dichlorophenyl)sulfinyl)-1-((6-(1,3-thiazol-2-ylamino)pyridin-2-yl)methyl)cyclohexanecarboxylic acid trifluoroacetate

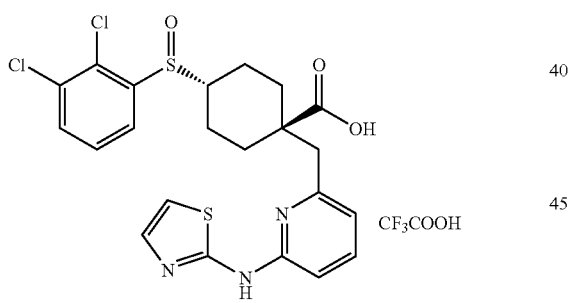

To a suspension of 8.0 mg of trans-4-((2,3-dichlorophenyl)thio)-1-((6-(1,3-thiazol-2-ylamino)pyridin-2-yl)methyl)cyclohexanecarboxylic acid trifluoroacetate as obtained in Example 30 in 0.24 ml of acetonitrile and 0.12 ml of water was added a solution of 8.6 mg of OXONE® (potassium peroxymonosulfate, purchased from Aldrich) in 0.12 ml of water at room temperature, followed by stirring the reaction mixture at room temperature for 2 hours. The reaction mixture was concentrated in vacuo. The resulting residue was purified by a reversed phase preparative liquid chromatography, followed by concentrating the obtained fraction in vacuo to give the title compound as a white solid.

$^1$H-NMR(CD$_3$OD)δ: 1.26-1.41 (1H,m),1.73-1.82(1H,m), 1.85-2.21(6H,m),3.05-3.15(1H,m),3.29(2H,s),7.07(1H,d, J=8.0 Hz),7.11(1H,d,J=7.6 Hz),7.28(1H,d,J=4.0 Hz),7.59 (1H,d,J=4.0 Hz),7.59(1H,t,J=8.0 Hz),7.71-7.78(2H,m),7.83 (1H,t,J=8.0 Hz).

mass:510,512(M+1)$^+$

Example 32

Synthesis of trans-4-((2,3-dichlorophenyl)sulfonyl)-1-((6-(1,3-thiazol-2-ylamino)pyridin-2-yl)methyl)cyclohexanecarboxylic acid trifluoroacetate

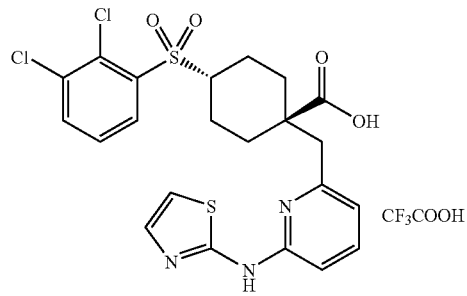

To a suspension of 6.60 mg of trans-4-((2,3-dichlorophenyl)thio)-1-((6-(1,3-thiazol-2-ylamino)pyridin-2-yl)methyl)cyclohexanecarboxylic acid trifluoroacetate as obtained in Example 30 in 0.24 ml of acetonitrile and 0.12 ml of water was added a solution of 14.7 mg of OXONE® (potassium peroxymonosulfate) in 0.12 ml of water at room temperature, followed by stirring the reaction mixture at room temperature overnight. The reaction mixture was concentrated in vacuo. The resulting residue was purified by a reversed phase preparative liquid chromatography, followed by concentrating the obtained fraction in vacuo to give the title compound as a white solid.

$^1$H-NMR(DMSO-d$_6$)δ: 1.59-1.76(4H,m),1.85-1.92(2H, m),1.98-2.11(2H,m),3.02(2H,s),3.61-3.70(1H,m),6.65(1H, d,J=8.0 Hz),6.86(1H,d,J=8.0 Hz),7.01 (1H,d,J=3.6 Hz),7.38 (1H,d,J=3.6 Hz),7.56(1H,t,J=8.0 Hz),7.65(1H,t,J=8.0 Hz), 8.03(2H,d,J=8.0 Hz), 11.15(1H,brs).

mass:526,528(M+1)$^+$

Example 33

Synthesis of trans-4-((2,3-dichlorophenyl)thio)-1-((6-(1H-pyrazol-3-ylamino)pyridin-2-yl)methyl)cyclohexanecarboxylic acid trifluoroacetate

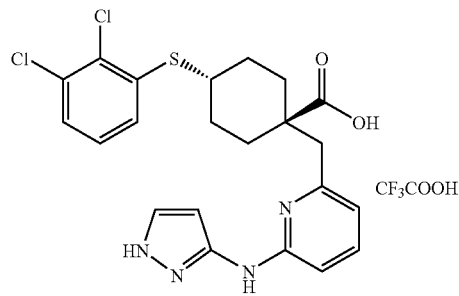

(1) Synthesis of tert-butyl cis-1-((6-((1-tert-butyl-1H-pyrazol-5-yl)amino)pyridin-2-yl)methyl)-4-hydroxycyclohexanecarboxylate

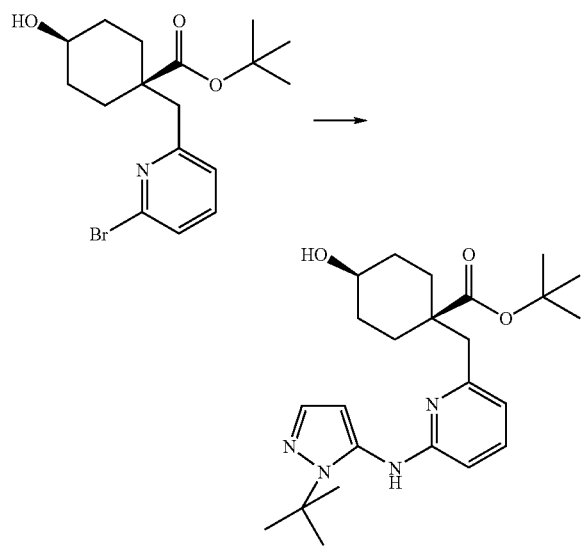

The title compound was obtained as a yellow solid in the same manner as in the step of Example 9(5) using tert-butyl cis-1-((6-bromopyridin-2-yl)methyl)-4-hydroxycyclohexanecarboxylate as obtained in the step of Example 9(3) instead of tert-butyl trans-1-((6-bromopyridin-2-yl)methyl)-4-(2-fluoro-3-(trifluoromethyl)phenoxy)cyclohexanecarboxylate as used in Example 9(5).

(2) Synthesis of tert-butyl trans-1-((6-((1-tert-butyl-1H-pyrazol-5-yl)amino)pyridin-2-yl)methyl)-4-((2,3-dichlorophenyl)thio)cyclohexanecarboxylate

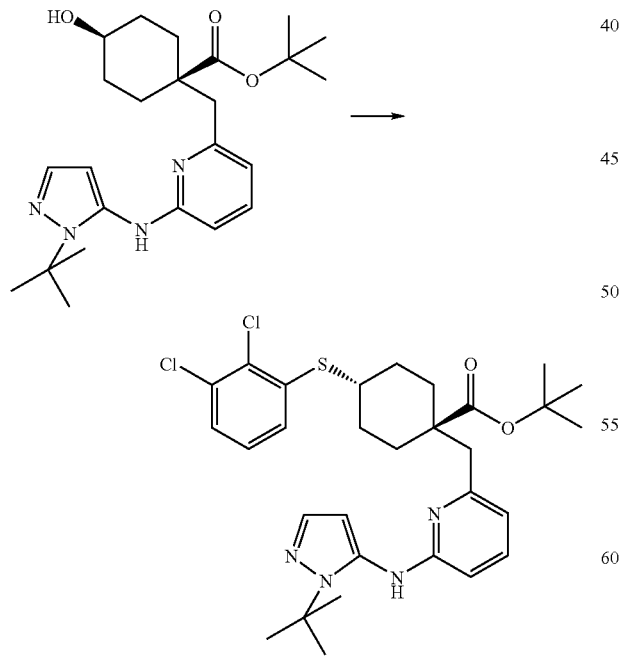

The title compound was obtained as an off-white solid in the same manner as in the step of Example 30(1) using tert-butyl cis-1-((6-((1-tert-butyl-1H-pyrazol-5-yl)amino)pyridin-2-yl)methyl)-4-hydroxycyclohexanecarboxylate instead of tert-butyl cis-4-hydroxy-1-((6-(((2Z)-3-(methoxymethyl)-1,3-thiazol-2(3H)-ylidene)amino)pyridin-2-yl)methyl)cyclohexanecarboxylate as used in the step of Example 30(1).

(3) Synthesis of trans-4-((2,3-dichlorophenyl)thio)-1-((6-(1H-pyrazol-3-ylamino)pyridin-2-yl)methyl)cyclohexanecarboxylic acid trifluoroacetate

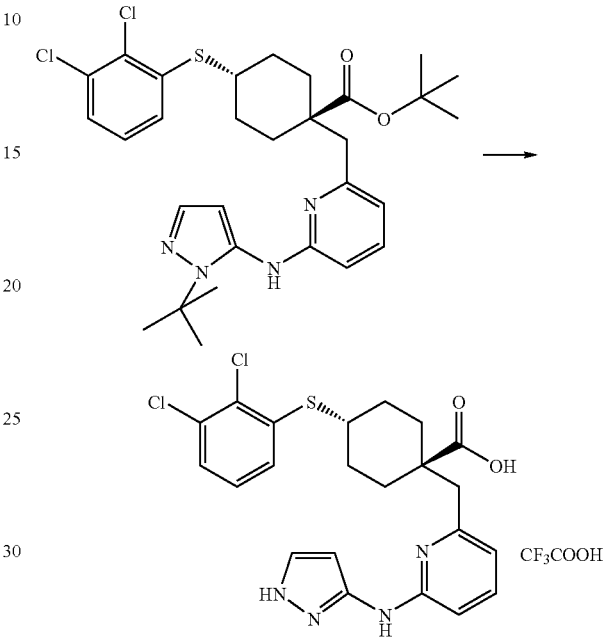

The title compound was obtained as a white solid in the same manner as in the step of Example 9(6) using tert-butyl trans-1-((6-((1-tert-butyl-1H-pyrazol-5-yl)amino)pyridin-2-yl)methyl)-4-((2,3-dichlorophenyl)thio)cyclohexanecarboxylate instead of tert-butyl trans-1-((6-((1-tert-butyl-1H-pyrazol-5-yl)amino)pyridin-2-yl)methyl)-4-(2-fluoro-3-(trifluoromethyl)phenoxy)cyclohexanecarboxylate as used in the step of Example 9(6).

$^1$H-NMR(CD$_3$OD)δ: 1.77-2.12(8H,m),3.22(2H,s),3.60-3.70(1H,m),6.13(1H,d,J=2.4 Hz),6.99(1H,d,J=8.0 Hz),7.14(1H,d,J=8.0 Hz),7.24(1H,t,J=8.0 Hz),7.37(1H,dd,J=8.0,1.2 Hz),7.40(1H,dd,J=7.6,1.2 Hz),7.75(1H,d,J=2.4 Hz),8.01(1H,dd,J=8.0,7.6 Hz).

mass:477,479(M+1)$^+$

Example 34

Synthesis of 5-(trans-4-((2,3-dichlorophenyl)thio)-1-((6-(1H-pyrazol-3-ylamino)pyridin-2-yl)methyl)cyclohexyl)-1,3,4-oxadiazol-2(3H)-one trifluoroacetate

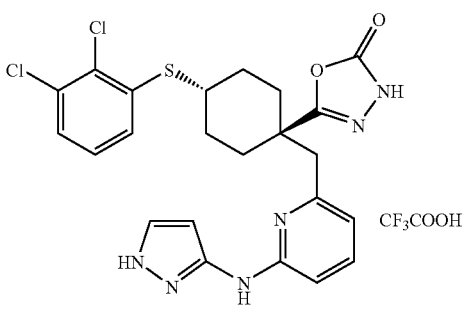

The title compound was obtained as a white solid in the same manner as in the steps of Example 20(2) to 20 (4) using trans-4-((2,3-dichlorophenyl)thio)-1-((6-(1H-pyrazol-3-ylamino)pyridin-2-yl)methyl)cyclohexanecarboxylic acid trifluoroacetate as obtained in Example 33, instead of trans-1-((6-((1-tert-butyl-1H-pyrazol-5-yl)amino)pyridin-2-yl) methyl)-4-(2-fluoro-3-(trifluoromethyl)phenoxy)cyclohexanecarboxylic acid trifluoroacetate as used in Example 20(2).

$^1$H-NMR(CD$_3$OD)δ: 1.82-1.92(2H,m),1.96-2.17(6H,m), 3.29(2H,s),3.66-3.72(1H,m),6.14(1H,d,J=2.8 Hz),6.99(1H, d,J=7.6 Hz),7.17(1H,d,J=8.8 Hz),7.25(1H,t,J=8.0 Hz),7.38 (1H,dd,J=8.0,1.6 Hz),7.41 (1H,dd,J=8.0,1.6 Hz),7.75(1H,d, J=2.8 Hz),8.02(1H,dd,J=8.8,7.6 Hz).

mass:517,519(M+1)$^+$

Example 35

Synthesis of 5-(trans-4-((2,3-dichlorophenyl)sulfinyl)-1-((6-(1H-pyrazol-3-ylamino)pyridin-2-yl)methyl)cyclohexyl)-1,3,4-oxadiazol-2(3H)-one trifluoroacetate

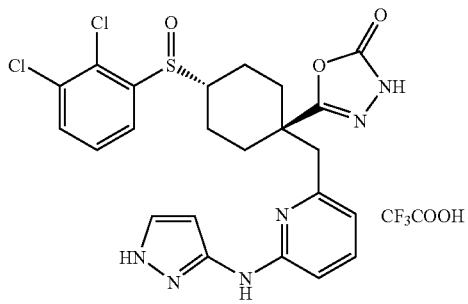

The title compound was obtained as a white solid in the same manner as in Example 31 using 5-(trans-4-((2,3-dichlorophenyl)thio)-1-((6-(1H-pyrazol-3-ylamino)pyridin-2-yl) methyl)cyclohexyl)-1,3,4-oxadiazol-2(3H)-one trifluoroacetate as obtained in Example 34, instead of trans-4-((2,3-dichlorophenyl)thio)-1-((6-(1,3-thiazol-2-ylamino)pyridin-2-yl)methyl)cyclohexanecarboxylic acid trifluoroacetate as used in Example 31.

$^1$H-NMR(CD$_3$OD)δ: 1.45-1.56(1H,m), 1.86-1.99(1H,m), 2.00-2.23(6H,m),3.12-3.23(1H,m),3.36(1H,d,J=14.4 Hz), 3.42(1H,d,J=14.4 Hz),6.15(1H,d,J=2.8 Hz),6.97(1H,d,J=7.2 Hz), 7.17(1H,d,J=8.8 Hz),7.62(1H,dd,J=8.0,7.2 Hz),7.76-7.80(3H,m),8.03(1H,dd,J=8.8,7.2 Hz).

mass:533,535(M+1)$^+$

Example 36

Synthesis of 5-(trans-4-((2,3-dichlorophenyl)sulfonyl)-1-((6-(1H-pyrazol-3-ylamino)pyridin-2-yl)methyl)cyclohexyl)-1,3,4-oxadiazol-2(3H)-one trifluoroacetate

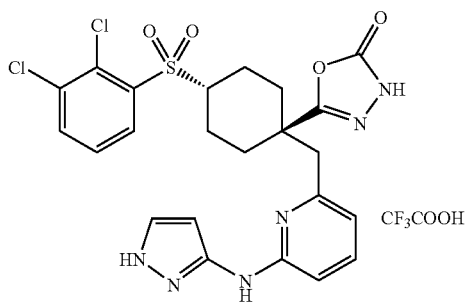

The title compound was obtained as a yellow solid in the same manner as in Example 32 using 5-(trans-4-((2,3-dichlorophenyl)thio)-1-((6-(1H-pyrazol-3-ylamino)pyridin-2-yl) methyl)cyclohexyl)-1,3,4-oxadiazol-2(3H)-one trifluoroacetate as obtained in Example 34, instead of trans-4-((2,3-dichlorophenyl)thio)-1-((6-(1,3-thiazol-2-ylamino)pyridin-2-yl)methyl)cyclohexanecarboxylic acid trifluoroacetate as used in Example 32.

$^1$H-NMR(CD$_3$OD)δ: 1.90-2.25(8H,m),3.34(2H,s),3.73-3.83(1H,m),6.15(1H,d,J=2.8 Hz),6.97(1H,d,J=7.2 Hz),7.17 (1H,d,J=8.8 Hz),7.58(1H,t,J=8.0 Hz),7.77(1H,d,J=2.8 Hz), 7.93(1H,dd,J=8.0,1.6 Hz),8.02(1 H,dd,J=8.8,7.2 Hz),8.09 (1H,dd,J=8.0,1.6 Hz).

mass:549,551(M+1)$^+$

Example 37

Synthesis of trans-4-(2-cyano-3-fluorophenoxy)-1-((6-(1H-pyrazol-3-ylamino)pyridin-2-yl)methyl) cyclohexanecarboxylic acid trifluoroacetate

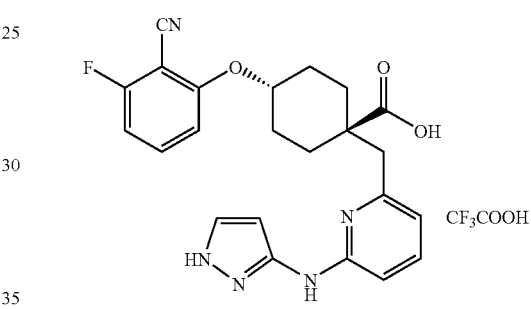

The title compound was obtained as a white solid in the same manner as in Example 9 using 2-cyano-3-fluorophenol, instead of 2-fluoro-3-(trifluoromethyl)phenol as used in Example 9(4).

$^1$H-NMR(CD$_3$OD)δ: 1.84-2.16(8H,m),3.22(2H,s),4.86 (1H,brs),6.18(1H,d,J=2.6 Hz),6.90(1H,t,J=8.8 Hz),7.03(2: H,d,J=8.8 Hz),7.21(1H,d,J=8.8 Hz),7.60-7.66(1H,m),7.77 (1H,d,J=2.6 Hz),8.05(1H,dd,J=8.8,7.2 Hz).

mass:436(M+1)$^+$

Example 38

Synthesis of trans-4-(2-cyano-3-fluorophenoxy)-1-((6-(1H-pyrazol-3-ylamino)pyridin-2-yl)methyl) cyclohexanecarboxamide

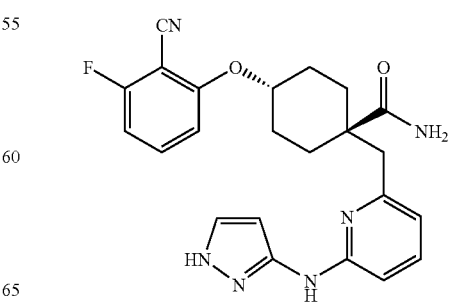

The title compound was obtained as a pale yellow solid in the same manner as in Example 11 using trans-4-(2-cyano-3-fluorophenoxy)-1-((6-(1H-pyrazol-3-ylamino)pyridin-2-yl)methyl)cyclohexanecarboxylic acid trifluoroacetate as obtained in Example 37, instead of trans-4-(3-chloro-2-fluorophenoxy)-1-((6-(1H-pyrazol-3-ylamino)pyridin-2-yl)methyl)cyclohexanecarboxylic acid trifluoroacetate as used in Example 11.

$^1$H-NMR(CD$_3$OD)δ: 1.85-2.08(8H,m),3.04(2H,brs),4.80 (1H,brs),5.74(1H,brs),6.55-6.75(2H,m),6.90(1H,t,J=8.8 Hz),7.05(1H,d,J=8.8 Hz),7.36-7.55(2H,m),7.58-7.67(1H, m).

mass:435(M+1)$^+$

Example 39

Synthesis of trans-4-(3-chloro-2-fluorophenoxy)-1-((6-((5-methyl-1H-pyrazol-3-yl)amino)pyridin-2-yl) methyl)cyclohexanecarboxylic acid trifluoroacetate

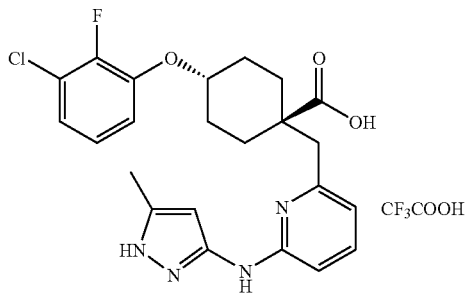

The title compound was obtained as a white solid in the same manner as in Example 9 using 3-chloro-2-fluorophenol and 1-tert-butyl-3-methyl-1H-pyrazol-5-amine, instead of both 2-fluoro-3-(trifluoromethyl)phenol and 1-tert-butyl-1H-pyrazol-5-amine p-toluenesulfonate as used in Example 9(4) and (5).

$^1$H-NMR(CD$_3$OD):δ: 1.78-2.10(8H,m),3.16(2H,s),4.59 (1H,brs),5.90(1H,s),6.95-7.20(5H,m),7.99(1H,t,J=8.0 Hz).

mass:459,461(M+1)$^+$

Example 40

Synthesis of trans-1-((4-bromo-6-(1,3-thiazol-2-ylamino)pyridin-2-yl)methyl)-4-(3-chloro-2-fluorophenoxy)cyclohexanecarboxylic acid hydrochloride

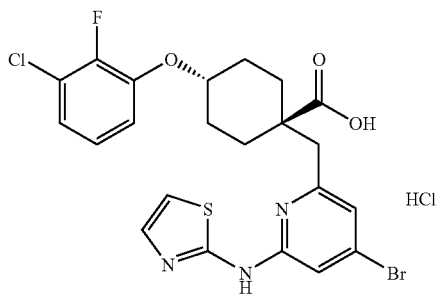

The title compound was obtained as a white solid in the same manner as in Example 1 using (4-bromo-6-(((2Z)-3-(methoxymethyl)-1,3-thiazol-2(3H)-ylidene)amino)pyridin-2-yl)methanol (WO2006/046734, Page 98), instead of (6-(((2Z)-3-(methoxymethyl)-1,3-thiazol-2(3H)-ylidene) amino)pyridin-2-yl)methanol as used in Example 1(4).

$^1$H-NMR(CDCl$_3$)δ: 1.74-1.95(4H,m),2.03-2.18(4H,m), 3.09(2H,brs),4.58(1H,s),6.77-6.82(1H,m),6.90-6.96(1H,m), 6.98-7.05(3H,m),7.17(1H,s),7.33(1H,s).

mass:540,542(M+1)$^+$

Example 41

Synthesis of 5-(trans-4-(3-chloro-2-fluorophenoxy)-1-((4-methyl-6-(1H-pyrazol-3-ylamino)pyrimidin-2-yl)methyl)cyclohexyl)-1,3,4-oxadiazol-2(3H)-one trifluoroacetate

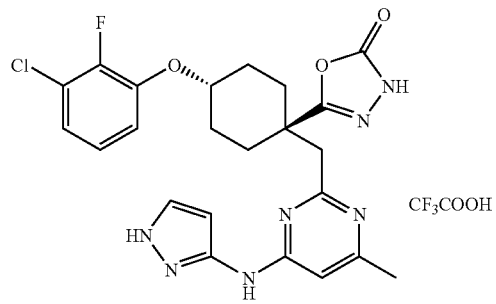

The title compound was obtained as a white solid in the same manner as in Example 14 using 2,4-dichloro-6-methylpyrimidine, instead of 2,6-dichloropyrazine as used in Example 14(1).

$^1$H-NMR(CD$_3$OD)δ: 1.73-1.86(2H,m),1.93-2.16(6H,m), 2.48(3H,s),3.15(2H,brs),4.62(1H,brs),6.99-7.11 (3H,m), 7.63(1H,brs).

mass:500,502(M+1)$^+$

Example 42

Synthesis of 5-(trans-4-(2-fluoro-3-(trifluoromethyl) phenoxy)-1-((6-(1H-pyrazol-3-ylamino)pyridin-2-yl) methyl)cyclohexyl)-1,3,4-oxadiazole-2(3H)-thione trifluoroacetate

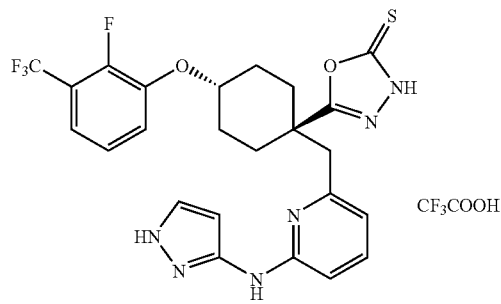

The title compound was obtained as a white solid in the same manner as in Example 24 using trans-1-((6-((1-tert-butyl-1H-pyrazol-5-yl)amino)pyridin-2-yl)methyl)-4-(2-fluoro-3-(trifluoromethyl)phenoxy)cyclohexanecarbohydrazide as obtained in Example 20(3), instead of trans-1-((6-((1-tert-butyl-1 H-pyrazol-5-yl)amino)pyridin-2-yl)methyl)-4-(3-chloro-2-fluorophenoxy)cyclohexanecarbohydrazide as used in Example 24(1).

$^1$H-NMR(CD$_3$OD)δ: 1.73-1.85(2H,m),2.01-2.25(6H,m), 3.35(2H,s),4.66(1H,brs),6.15 (1H,d,J=2.4 Hz),6.97(1H,d, J=7.2 Hz),7.18-7.28(3H,m),7.38-7.45(1H,m),7.76(1H,d, J=2.4 Hz),8.03(1H,t,J=7.6 Hz).

mass:535(M+1)$^+$

Reference 1

Synthesis of tert-butyl 4-((tert-butyl(diphenyl)silyl)oxy)cyclohexanecarboxylate

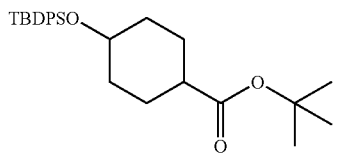

(1) Synthesis of ethyl 4-((tert-butyl(diphenyl)silyl)oxy)cyclohexanecarboxylate

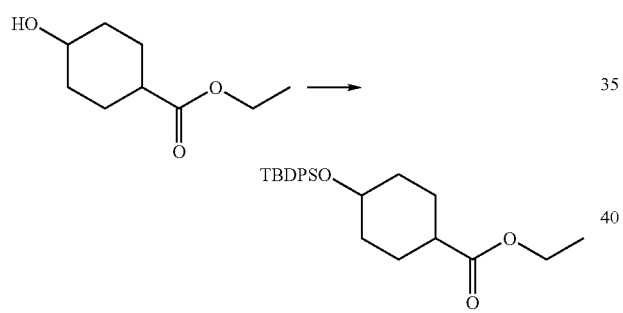

To a solution of 25 g of 4-hydroxycyclohexanecarboxylic acid in 125 ml of N,N-dimethylformamide were sequentially added 21.7 g of imidazole and 39.6 ml of tert-butyl (diphenyl)silyl chloride under cooling with ice, followed by stirring the reaction mixture at room temperature for 3 hours. To the reaction mixture was added water and extracted with hexane. The resulting hexane solution was washed with brine, dried over anhydrous magnesium sulfate and filtered. The filtrate was concentrated in vacuo to give the title compound.

(2) Synthesis of 4-((tert-butyl(diphenyl)silyl)oxy)cyclohexanecarboxylic acid

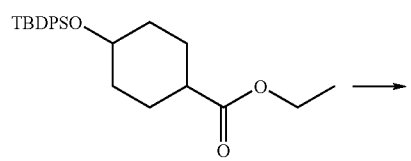

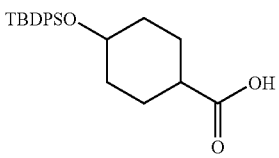

To a solution of 64.2 g of ethyl 4-((tert-butyl(diphenyl)silyl)oxy)cyclohexanecarboxylate in 200 ml of methanol and 200 ml of tetrahydrofuran was added 58 ml of 5 M aqueous sodium hydroxide solution, followed by stirring at room temperature overnight. The reaction mixture was neutralized with 5 M aqueous hydrochloride solution, followed by removal of the methanol and tetrahydrofuran in vacuo, and the resulting residue was extracted with ethyl acetate. The obtained ethyl acetate solution was washed with brine, dried over anhydrous magnesium sulfate and filtered. The filtrate was concentrated in vacuo to give the title compound.

(3) Synthesis of tert-butyl 4-((tert-butyl(diphenyl)silyl)oxy)cyclohexanecarboxylate

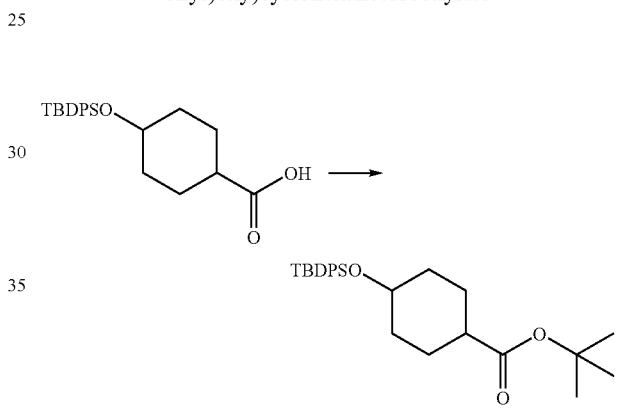

To a solution of 62.8 g of 4-((tert-butyl(diphenyl)silyl)oxy)cyclohexanecarboxylic acid in 270 ml of tert-butyl alcohol were successively added 63.3 g of di-tert-butyl dicarbonate and 5.31 g of 4-dimethylaminopyridine in room temperature, followed by stirring the reaction mixture at room temperature for 3 hours. The reaction mixture was concentrated in vacuo to remove tert-butylalcohol, and the resulting residue was purified by a silica gel column chromatography (eluent: hexane to hexane/ethyl acetate=19/1) to give the title compound as a pale yellow oil.

Reference 2

Synthesis of 4-((tert-butyl(diphenyl)silyl)oxy)cyclohexanecarbonitrile

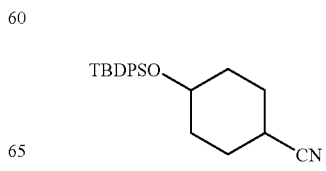

(1) Synthesis of 4-((tert-butyl(diphenyl)silyl)oxy) cyclohexanecarboxamide

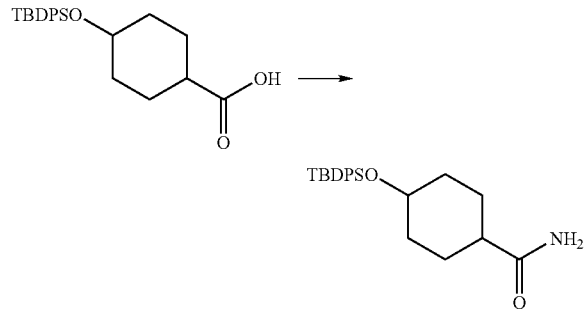

To a solution of 6.64 g of 4-((tert-butyl(diphenyl)silyl)oxy) cyclohexanecarboxylic acid as obtained in the step of Reference 1(2) in 100 ml of chloroform were successively added 4.65 g of ammonium chloride, 30.3 ml of diusopropylethylamine, 8.0 g of hydroxybenzotriazole hydrate and 10.0 g of 1-(3-dimethylaminopropyl)-3-ethylcarbodiimide hydrochloride at room temperature, followed by stirring the reaction mixture at room temperature overnight. The reaction mixture was washed with water and brine, dried over anhydrous magnesium sulfate and filtered. The filtrate was concentrated in vacuo. The obtained residue was purified by a silica gel column chromatography (eluent: hexane/ethyl acetate=10/1 to ethyl acetate) to give the title compound.

(2) Synthesis of 4-((tert-butyl(diphenyl)silyl)oxy) cyclohexanecarbonitrile

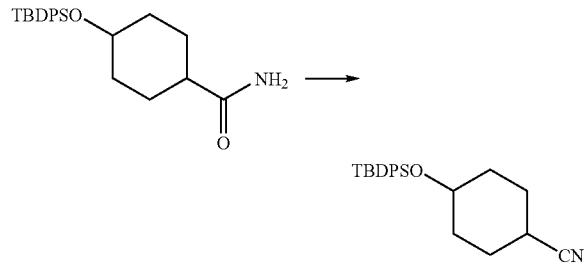

To a solution of 6.42 g of 4-((tert-butyl(diphenyl)silyl)oxy) cyclohexanecarboxamide and 2.39 ml of dimethylsulfoxide in 90 ml of methylene chloride was added a solution of 2.06 ml of oxalyl chloride in 10 ml of methylene chloride at −78° C., followed by stirring the reaction mixture at −78° C. for 15 minutes. To the reaction mixture was added 7.05 ml of triethylamine at −78° C., followed by stirring the reaction mixture at −78° C. for 30 minutes and then stirring at room temperature for 1.5 hours. The reaction mixture was washed with water and brine, dried over anhydrous magnesium sulfate and filtered. The filtrate was concentrated in vacuo. The obtained residue was purified by a silica gel column chromatography (eluent: hexane to hexane/ethyl acetate=4/1) to give the title compound as a pale yellow oil.

Reference 3

Synthesis of 1-tert-butyl-1H-pyrazol-5-amine

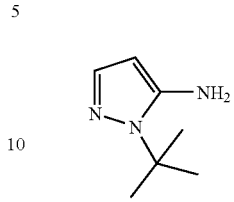

To 600 ml of ethanol were successively added 59.94 g of tert-butylhydrazine hydrochloride, 79.3 g of sodium acetate and 50 ml of 2-chloroacrylonitrile at room temperature, followed by stirring the reaction mixture at 80° C. for 12 hours. After removing the solvent in vacuo, water was added to the residue. The mixture was neutralized with sodium hydrogen carbonate, and extracted with ethyl acetate. The obtained ethyl acetate solution was washed with brine, dried over anhydrous magnesium sulfate and filtered. The filtrate was concentrated in vacuo. The obtained residue was purified by a silica gel column chromatography (eluent: hexane/ethyl acetate=2/1-1/2) to give the title compound as a pale yellow oil.

Reference 4

Synthesis of 1-tert-butyl-1H-pyrazol-5-amine p-toluenesulfonate

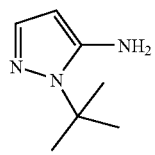

To 850 ml of ethanol were successively added 85.64 g of tert-butylhydrazine hydrochloride, 112.54 g of sodium acetate and 72 ml of 2-chloroacrylonitrile at room temperature, followed by stirring the reaction mixture at 80° C. for 12 hours. After removing the solvent in vacuo, water was added to the residue. The mixture was neutralized with sodium hydrogen carbonate, and extracted with ethyl acetate. The obtained ethyl acetate solution was washed with brine, dried over anhydrous magnesium sulfate and filtered, and the filtrate was concentrated in vacuo. To a solution of the obtained residue in 700 ml of ethyl acetate was added a solution of 96.16 g of p-toluenesulfonic acid hydrate in 140 ml of ethanol under stirring, followed by leaving the resultant mixture as it is overnight. The obtained precipitate was collected and washed with ethyl acetate to give the title compound as a white solid.

INDUSTRIAL APPLICABILITY

The compound of the invention is characterized in that it has cell growth inhibitory action as well as synergistic action with other antitumor agents, based on excellent Aurora A selective inhibitory action, and thus it is expected as a useful antitumor agent in the field of pharmaceuticals.

What is claimed is:

1. A compound of formula I:

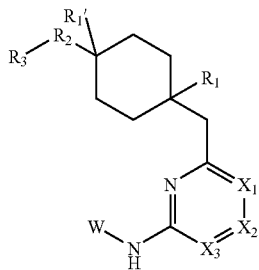

(I)

wherein:

R$_1$ is a hydrogen atom, F, CN, COOR$_{a1}$, CONR$_{a2}$R$_{a2}$', NR$_{a3}$COR$_{a3}$', CONR$_{a4}$OR$_{a4}$', NR$_{a5}$CONR$_{a5}$'R$_{a5}$''', NR$_{a6}$COOR$_{a6}$', SO$_2$NR$_{a7}$R$_{a7}$', NR$_{a8}$SO$_2$R$_{a8}$', COR$_{a9}$, SO$_2$R$_{a10}$, NO$_2$, OR$_{a11}$, NR$_{a12}$R$_{a12}$', lower alkyl which may be substituted, or a heterocyclic group which may be substituted, wherein:

R$_{a1}$, R$_{a3}$, R$_{a4}$, R$_{a5}$, R$_{a6}$, and R$_{a8}$ are each independently a hydrogen atom or lower alkyl which may be substituted;

R$_{a2}$, R$_{a2}$', R$_{a5}$', R$_{a5}$''', R$_{a7}$, R$_{a7}$', R$_{a12}$, and R$_{a12}$' are each independently a hydrogen atom or lower alkyl which may be substituted, provided, however, that R$_{a2}$ and R$_{a2}$'; R$_{a5}$' and R$_{a5}$'''; R$_{a7}$ and R$_{a7}$'; R$_{a12}$ and R$_{a12}$' each independently, together with the nitrogen atom which they bind to, may form a heterocyclic group which may be substituted;

R$_{a3}$', R$_{a4}$', R$_{a6}$', R$_{a8}$', R$_{a9}$, R$_{a10}$ and R$_{a11}$ are each independently a hydrogen atom or lower alkyl which may be substituted;

R$_1$' is a hydrogen atom or lower alkyl which may be substituted;

R$_2$ is O, S, SO, SO$_2$, NH, NR$_b$, or CR$_{c1}$R$_{c2}$ wherein R$_b$ is a lower alkyl which may be substituted, and R$_{c1}$ and R$_{c2}$, which may be the same or different, are a hydrogen atom or lower alkyl;

R$_3$ is a phenyl which may be substituted;

X$_1$ is CH, CX$_{1a}$ or N wherein X$_{1a}$ is a lower alkyl which may be substituted;

X$_2$ is CH, CX$_{2a}$, or N wherein:

X$_{2a}$ is a lower alkyl; or

X$_{2a}$ is a substituent selected from substituent group A$_1$, or lower alkyl which is substituted with one or more of the same or different substituents selected from substituent group A$_1$, wherein substituent group A$_1$ is halogen atom; cyano; hydroxy; lower alkylamino; di-lower alkylamino; lower alkoxy which may be substituted with one or more hydroxy groups; lower alkylthio; and lower alkylsulfonyl; or X$_{2a}$ is COOR$_{x1}$, CONR$_{x2}$R$_{x3}$, NHCOR$_{x1}$, NHCONR$_{x2}$R$_{x3}$, NHSO$_2$NR$_{x2}$R$_{x3}$, NR$_{x4}$R$_{x5}$, or CH$_2$NR$_{x4}$R$_{x5}$, wherein:

R$_{x1}$ is a hydrogen atom or lower alkyl which may be substituted;

R$_{x2}$ and R$_{x3}$, which may be the same or different, are each a hydrogen atom, lower alkyl which may be substituted, or cycloalkyl which may be substituted; or alternatively R$_{x2}$ and R$_{x3}$, together with the nitrogen atom to which they bond, form a 5- or 6-membered aliphatic heterocyclic group which contains at least one atom selected from N, O and S and which may be substituted; and R$_{x4}$ and R$_{x5}$, which may be the same or different, are a hydrogen atom, lower alkyl that may be substituted, or cycloalkyl that may be substituted; or $X_{2a}$ is a 5- to 6-membered aliphatic heterocyclic group which contains at least one atom selected from N, O and S and which may be substituted, wherein two hydrogen atoms that are bonded to the same carbon atom of the aliphatic heterocyclic group may be substituted with oxo and neighboring two carbon atoms constituting the aliphatic heterocyclic ring may form a double-bond; or a lower alkyl which is substituted with the aliphatic heterocyclic group; or $X_{2a}$ is a 5- to 6-membered aromatic heterocyclic group which contains at least one atom selected from N, O and S and which may be substituted; or a lower alkyl which is substituted with the aromatic heterocyclic group;

$X_3$ is CH, $CX_{3a}$, or N wherein $X_{3a}$ is a lower alkyl which may be substituted;

provided, however, that among $X_1$, $X_2$ and $X_3$, the number of nitrogen is 0 or 1;

W is the following residue:

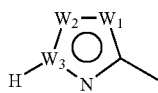

wherein:
$W_1$ is CH, N, NH, O, or S;
$W_2$ is CH, $CW_{2a}$, N, $NW_{2b}$, O or S, wherein $W_{2a}$ and $W_{2b}$ are each independently a hydrogen atom, halogen atom, cyano, lower alkyl having one to two carbon atoms, cycloalkyl having three to five carbon atoms, or lower alkyl having one to two carbon atoms which may be substituted with one or more halogen atoms;
$W_3$ is C or N; and
at least one of $W_1$, $W_2$, and $W_3$ is carbon atom; however, two of $W_1$, $W_2$, and $W_3$ are not simultaneously O and S, or a pharmaceutically acceptable salt or ester thereof.

2. The compound according to claim 1 or a pharmaceutically acceptable salt or ester thereof, wherein $R_1'$ is a hydrogen atom, and $X_3$ is CH.

3. The compound according to claim 2 or a pharmaceutically acceptable salt or ester thereof, wherein:
$R_1$ is a hydrogen atom, F, CN, $COOR_{a1}$, $CONR_{a2}R_{a2}'$, $NR_{a3}COR_{a3}'$, $CONR_{a4}OR_{a4}'$, $NR_{a5}CONR_{a5}'R_{a5}''$, $NR_{a6}COOR_{a6}'$, $SO_2NR_{a7}R_{a7}'$, $NR_{a8}SO_2R_{a8}'$, $COR_{a9}$, $SO_2R_{a10}$, $NO_2$, $OR_{a11}$, or $NR_{a12}R_{a12}'$, wherein:
$R_{a1}$, $R_{a3}$, $R_{a4}$, $R_{a5}$, $R_{a6}$, and $R_{a8}$ are each independently a hydrogen atom or lower alkyl;
$R_{a2}$, $R_{a2}'$, $R_{a5}'$, $R_{a5}''$, $R_{a7}$, $R_{a7}'$, $R_{a12}$, and $R_{a12}'$ are each independently a hydrogen atom or lower alkyl which may be substituted with one or more of the same or different substituents selected from substituent group $L_1$, wherein substituent group $L_1$ is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; provided, however, that $R_{a2}$ and $R_{a2}'$; $R_{a5}'$ and $R_{a5}''$; $R_{a7}$ and $R_{a7}'$; $R_{a12}$ and $R_{a12}'$ each independently, together with the nitrogen atom which they bind to, may form a 5-membered or 6-membered aromatic or aliphatic heterocyclic group which may be substituted with one or more of the same or different substituents selected from substituent group $L_2$, wherein substituent group $L_2$ is a halogen atom, hydroxy, amino, and hydroxymethyl;
$R_{a3}'$, $R_{a4}'$, $R_{a6}'$, $R_{a8}'$, $R_{a9}$, $R_{a10}$ and $R_{a11}$ are each independently a hydrogen atom or lower alkyl which may be substituted with one or more of the same or different substituents selected from substituent group $L_1$; or
$R_1$ is a lower alkyl which may be substituted with one or more of the same or different substituents selected from substituent group M, wherein substituent group M is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; or
$R_1$ is a heterocyclic group selected from the following, wherein $Y_1$ and $Y_2$ are the same and different, and each a hydrogen atom or lower alkyl which may be substituted:

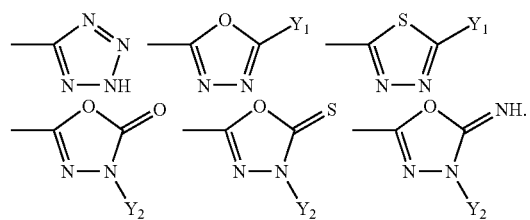

4. The compound according to claim 3 or a pharmaceutically acceptable salt or ester thereof, wherein W is selected from:

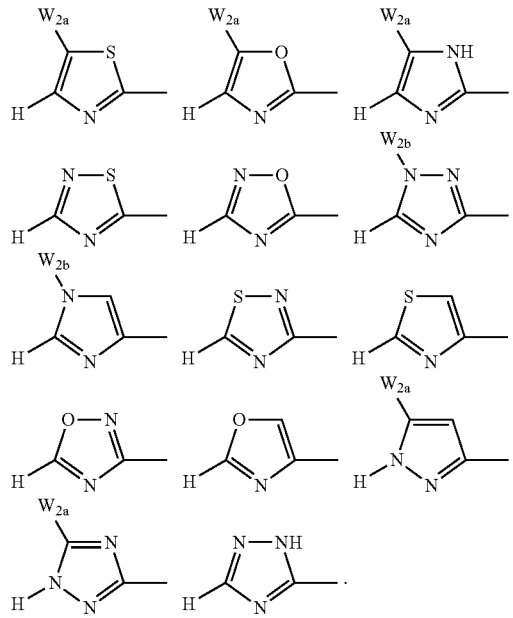

5. The compound according to claim 4 or a pharmaceutically acceptable salt or ester thereof, wherein $R_3$ is a phenyl of which $2^{nd}$ and $3^{rd}$ positions are substituted with the same or different two substituents selected from F, Cl, $CF_3$, and CN.

6. The compound according to claim 5 or a pharmaceutically acceptable salt or ester thereof, wherein substituent group $L_1$ is a halogen atom, hydroxy, amino, carbamoyl, lower alkylamino, di-lower alkylamino, and lower alkoxy;

and substituent group M is a hydroxy, carbamoyl, aminosulfonyl, lower alkylsulfonylamino, and carboxyl.

7. The compound according to claim 6 or a pharmaceutically acceptable salt or ester thereof, wherein both $X_1$ and $X_2$ are CH; or
$X_1$ is CH and $X_2$ is N; or
$X_1$ is N and $X_2$ is CH or $CX_{2a}$ wherein $X_{2a}$ is a lower alkyl or a halogen atom.

8. The compound according to claim 7 or a pharmaceutically acceptable salt or ester thereof, wherein $R_1$ is OH, COOH, or $CONR_{a2}R_{a2}'$ wherein $R_{a2}$ and $R_{a2}'$ are the same or different, and each a hydrogen atom or lower alkyl having one to three carbon atoms; or $R_1$ is selected from the following:

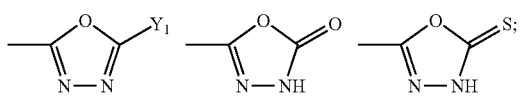

and $R_2$ is O, S, SO, or $SO_2$.

9. The compound according to claim 8 or a pharmaceutically acceptable salt or ester thereof, wherein:
W is selected from:

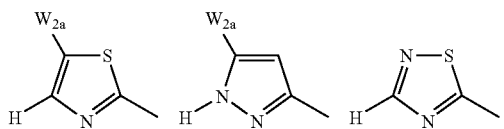

wherein $W_{2a}$ is a hydrogen atom, halogen atom, cyano, or methyl which may be substituted with one to three fluorine atoms.

10. The compound according to claim 9 or a pharmaceutically acceptable salt or ester thereof, wherein both of $X_1$ and $X_2$ are CH; or $X_1$ is CH and $X_2$ is N; and W is any one of the following:

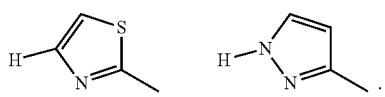

11. A compound which is:
(a) trans-4-(3-chloro-2-fluorophenoxy)-1-((6-(1,3-thiazol-2-ylamino)pyridin-2-yl)methyl)cyclohexanecarboxylic acid;
(b) trans-4-(2-fluoro-3-(trifluoromethyl)phenoxy)-1-((6-(1,3-thiazol-2-ylamino)pyridin-2-yl)methyl)cyclohexanecarboxylic acid;
(c) trans-4-(2,3-dichlorophenoxy)-1-((6-(1,3-thiazol-2-ylamino)pyridin-2-yl)methyl)cyclohexanecarboxylic acid;
(d) trans-4-(2-fluoro-3-(trifluoromethyl)phenoxy)-1-((6-(1H-pyrazol-3-ylamino)pyridin-2-yl)methyl)cyclohexanecarboxylic acid;
(e) trans-4-(3-chloro-2-fluorophenoxy)-1-((6-(1H-pyrazol-3-ylamino)pyrazin-2-yl)methyl)cyclohexanecarboxamide;
(f) 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazol-2(3H)-one;
(g) 5-(trans-4-(3-chloro-2-fluorophenoxy)-1-((6-(1H-pyrazol-3-ylamino)pyridin-2-yl)methyl)cyclohexyl)-1,3,4-oxadiazol-2(3H)-one;
(h) 5-(trans-4-(3-chloro-2-fluorophenoxy)-1-((6-(1H-pyrazol-3-ylamino)pyrazin-2-yl)methyl)cyclohexyl)-1,3,4-oxadiazol-2(3H)-one;
(i) 5-(trans-4-((2,3-dichlorophenyl)sulfonyl)-1-((6-(1H-pyrazol-3-ylamino)pyridin-2-yl)methyl)cyclohexyl)-1,3,4-oxadiazol-2(3H)-one;
(j) trans-1-((4-bromo-6-(1,3-thiazol-2-ylamino)pyridin-2-yl)methyl)-4-(3-chloro-2-fluorophenoxy)cyclohexanecarboxylic acid,
(k) 5-(trans-4-(3-chloro-2-fluorophenoxy)-1-((4-methyl-6-(1H-pyrazol-3-ylamino)pyrimidin-2-yl)methyl)cyclohexyl)-1,3,4-oxadiazol-2(3H)-one, or
(l) 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazole-2(3H)-thione,
or a pharmaceutically acceptable salt or ester thereof.

12. A compound which is:

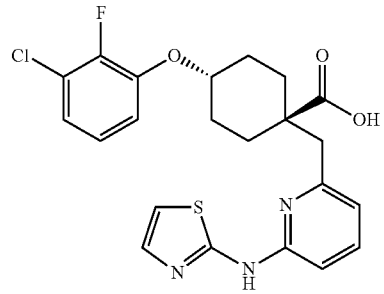

trans-4-(3-chloro-2-fluorophenoxy)-1-((6-(1,3-thiazol-2-ylamino)pyridin-2-yl)methyl)cyclohexanecarboxylic acid;
or a pharmaceutically acceptable salt or ester thereof.

13. A compound which is:

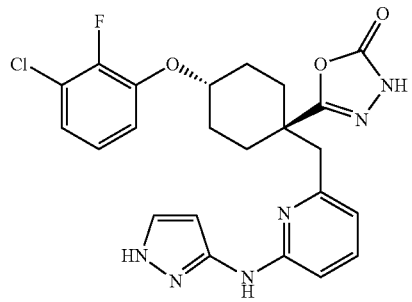

5-(trans-4-(3-chloro-2-fluorophenoxy)-1-((6-(1H-pyrazol-3-ylamino)pyridin-2-yl)methyl)cyclohexyl)-1,3,4-oxadiazol-2(3H)-one;
or a pharmaceutically acceptable salt or ester thereof.

14. A pharmaceutical composition comprising, together with pharmaceutically acceptable carrier or diluent, at least one compound according to claim 1 as active ingredient.

15. An Aurora A selective inhibitor comprising, together with a pharmaceutically acceptable carrier or diluent, at least one compound according to claim 1 as active ingredient.

16. An antitumor agent comprising, together with a pharmaceutically acceptable carrier or diluent, at least one compound according to claim 1 as active ingredient.

17. A combined preparation for simultaneous, separate, or sequential administration in the treatment of cancer, comprising two separate preparations:

a preparation comprising, together with a pharmaceutically acceptable carrier or diluent, a compound according to claim 1; and a preparation comprising, together with a pharmaceutically acceptable carrier or diluent, one antitumor agent selected from the group consisting of antitumor alkylating agents, antitumor antimetabolites, antitumor antibiotics, plant-derived antitumor agents, antitumor platinum-complex compounds, antitumor campthotecin derivatives, antitumor tyrosine kinase inhibitors, monoclonal antibodies, interferons, biological response modifiers, and other antitumor agents or a pharmaceutically acceptable salt thereof, wherein:

the antitumor alkylating agents are nitrogen mustard N-oxide, cyclophosphamide, ifosfamide, melphalan, busulfan, mitobronitol, carboquone, thiotepa, ranimustine, nimustine, temozolomide, and carmustine;

the antitumor antimetabolites are methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine, and pemetrexed disodium;

the antitumor antibiotics are actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, and valrubicin;

the plant-derived antitumor agents are vincristine, vinblastine, vindeshine, etoposide, sobuzoxane, docetaxel, paclitaxel, and vinorelbine;

the antitumor platinum-complex compounds are cisplatin, carboplatin, nedaplatin, and oxaliplatin;

the antitumor campthotecin derivatives are irinotecan, topotecan, and campthotecin;

the antitumor tyrosine kinase inhibitors are gefitinib, imatinib, sorafenib, sunitinib, dasatinib, and erlotinib;

the monoclonal antibodies are cetuximab, rituximab, bevacizumab, alemtuzumab, and trastuzumab;

the interferons are interferon α, interferon α-2a, interferon α-2b, interferon β, interferon γ-1a, and interferon γ-n1, the biological response modifiers are krestin, lentinan, sizofiran, picibanil, or ubenimex, and the other antitumor agents are mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

18. The combined preparation according to claim 17 wherein one of or both of the two separate preparations is/are oral preparation(s).

19. The combined preparation according to claim 17 which is further combined with at least one preparation comprising, together with a pharmaceutically acceptable carrier or diluent, an antitumor agent selected from the group consisting of antitumor alkylating agents, antitumor antimetabolites, antitumor antibiotics, plant-derived antitumor agents, antitumor platinum-complex compounds, antitumor campthotecin derivatives, antitumor tyrosine kinase inhibitors, monoclonal antibodies, interferons, biological response modifiers, and other antitumor agents, wherein the definition of each antitumor agent is the same as defined in claim 17, or a pharmaceutically acceptable salt thereof.

20. The combined preparation according to claim 17 wherein:

among the combined preparation, one is a preparation which comprises, together with a pharmaceutically acceptable carrier or diluent, (a) trans-4-(3-chloro-2-fluorophenoxy)-1-((6-(1,3-thiazol-2-ylamino)pyridin-2-yl)methyl)cyclohexanecarboxylic acid;

(b) trans-4-(2-fluoro-3-(trifluoromethyl)phenoxy)-1-((6-(1,3-thiazol-2-ylamino)pyridin-2-yl)methyl)cyclohexanecarboxylic acid;

(c) trans-4-(2,3-dichlorophenoxy)-1-((6-(1,3-thiazol-2-ylamino)pyridin-2-yl)methyl)cyclohexanecarboxylic acid;

(d) trans-4-(2-fluoro-3-(trifluoromethyl)phenoxy)-1-((6-(1H-pyrazol-3-ylamino)pyridin-2-yl)methyl)cyclohexanecarboxylic acid; or (e) trans-4-(3-chloro-2-fluorophenoxy)-1-((6-(1H-pyrazol-3-ylamino)pyrazin-2-yl)methyl)cyclohexanecarboxamide;

(f) 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazol-2(3H)-one;

(g) 5-(trans-4-(3-chloro-2-fluorophenoxy)-1-((6-(1H-pyrazol-3-ylamino)pyridin-2-yl)methyl)cyclohexyl)-1,3,4-oxadiazol-2(3H)-one;

(h) 5-(trans-4-(3-chloro-2-fluorophenoxy)-1-((6-(1H-pyrazol-3-ylamino)pyrazin-2-yl)methyl)cyclohexyl)-1,3,4-oxadiazol-2(3H)-one; or (i) 5-(trans-4-((2,3-dichlorophenyl)sulfonyl)-1-((6-(1H-pyrazol-3-ylamino)pyridin-2-yl)methyl)cyclohexyl)-1,3,4-oxadiazol-2(3H)-one;

(j) trans-1-((4-bromo-6-(1,3-thiazol-2-ylamino)pyridin-2-yl)methyl)-4-(3-chloro-2-fluorophenoxy)cyclohexanecarboxylic acid, (k) 5-(trans-4-(3-chloro-2-fluorophenoxy)-1-((4-methyl-6-(1H-pyrazol-3-ylamino)pyrimidin-2-yl)methyl)cyclohexyl)-1,3,4-oxadiazol-2(3H)-one, or (l) 5-(trans-4-(2-fluoro-3-(trifluoromethyl)phenoxy)-1-((6-(1H-pyrazol-3-ylamino)pyridin-2-yl)methyl)cyclohexyl)-1,3,4-oxadiazole-2(3H)-thione, or a pharmaceutically acceptable salt or ester thereof; and the other is a preparation which comprises, together with a pharmaceutically acceptable carrier or diluent, paclitaxel or docetaxel.

* * * * *